US012698509B2

(12) United States Patent
Reynolds et al.

(10) Patent No.: US 12,698,509 B2
(45) Date of Patent: Aug. 4, 2026

(54) COMPOSITIONS AND METHODS FOR CONTROLLING COLEOPTERAN INSECTS

(71) Applicant: Syngenta Crop Protection AG, Basel (CH)

(72) Inventors: Clarence Michael Reynolds, Durham, NC (US); Kevin V. Donohue, Durham, NC (US); Abdel Toure, Saint-Sauveur (FR)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/682,477

(22) PCT Filed: Aug. 11, 2022

(86) PCT No.: PCT/US2022/074792
§ 371 (c)(1),
(2) Date: Feb. 9, 2024

(87) PCT Pub. No.: WO2023/019190
PCT Pub. Date: Feb. 16, 2023

(65) Prior Publication Data
US 2025/0101452 A1     Mar. 27, 2025

Related U.S. Application Data

(60) Provisional application No. 63/232,340, filed on Aug. 12, 2021.

(51) Int. Cl.
*C12N 15/82*      (2006.01)
*A01N 37/46*     (2006.01)
*A01P 7/04*       (2006.01)
*C07K 14/245*    (2006.01)

(52) U.S. Cl.
CPC ......... *C12N 15/8286* (2013.01); *A01N 37/46* (2013.01); *A01P 7/04* (2021.08); *C07K 14/245* (2013.01)

(58) Field of Classification Search
CPC ....... C12N 15/8286; A01P 7/04; A01N 37/46; C07K 14/245
See application file for complete search history.

(56) References Cited

U.S. PATENT DOCUMENTS

2010/0210551 A1     8/2010   Bermudez et al.
2019/0185526 A1     6/2019   Donohue et al.

FOREIGN PATENT DOCUMENTS

WO       2019/211850 A1     7/2019

OTHER PUBLICATIONS

UniProt entry A0A7J4PLC7_9EURY: https://www.uniprot.org/uniprotkb/A0A7J4PLC7/entry (Year: 2021).*
International Search Report cited in Application No. PCT/US2022/074792 filed Aug. 11, 2022, mailed Dec. 16, 2022.

* cited by examiner

*Primary Examiner* — Anne Kubelik
*Assistant Examiner* — Victoria L Deleo
(74) *Attorney, Agent, or Firm* — Katherine Seguin

(57)     ABSTRACT

Novel pesticidal polypeptides that are active against Coleopteran pests are disclosed. Nucleic acid molecules encoding the novel insecticidal proteins are also provided. The nucleotide sequences encoding the pesticidal polypeptides can be used to transform prokaryotic and eukaryotic organisms to express the insecticidal proteins. Methods of making the insecticidal proteins and methods of using the insecticidal proteins, for example in transgenic plants to confer protection from insect damage are also disclosed.

13 Claims, No Drawings

Specification includes a Sequence Listing.

COMPOSITIONS AND METHODS FOR CONTROLLING COLEOPTERAN INSECTS

RELATED APPLICATION INFORMATION

This application is a 371 of International Application No. PCT/US2022/074792, filed Aug. 11, 2022, which claims priority to U.S. Application No. 63/232,340, filed Aug. 12, 2021, the contents of which are incorporated herein by reference herein.

STATEMENT REGARDING ELECTRONIC SUBMISSION OF A SEQUENCE LISTING

A Sequence Listing in xml format, submitted under 37 C.F.R. § 1.821, entitled "82452sequencelisting_NPE.xml", 256,965 bytes in size, generated on Feb. 5, 2024 and filed via EFS-Web is provided in lieu of a paper copy. This Sequence Listing is hereby incorporated by reference into the specification for its disclosures.

FIELD OF THE INVENTION

The present disclosure relates to novel pesticidal proteins having insecticidal activity, nucleic acid molecules that encode for and whose expression results in the pesticidal proteins, as well as compositions and methods for controlling agriculturally-relevant pests of crop plants.

BACKGROUND

Insects are a major cause of crop losses. Numerous commercially valuable plants, including common agricultural crops, are susceptible to attack by plant pests including insects and nematodes, causing substantial reductions in crop yield and quality. For example, plant pests are a major factor in the loss of the world's important agricultural crops. Insect pests are also a burden to vegetable and fruit growers, to producers of ornamental flowers, and they are a nuisance to home gardeners.

Species of corn rootworm are considered to be the most destructive corn pests. In the United States, the three important species are *Diabrotica virgifera virgifera*, the western corn rootworm, *D. longicornis barberi*, the northern corn rootworm and *D. undecimpunctata howardi*, the southern corn rootworm. Only western and northern corn rootworms are considered primary pests of corn in the US Corn Belt. Additionally, an important corn rootworm pest in the Southern US is the Mexican corn rootworm, *Diabrotica virgifera zeae*. Corn rootworm larvae cause substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections potentially leading to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or death. Good corn rootworm control can thus be reached but not without some inefficiencies. In some cases, application of these chemicals can affect other beneficial organisms. Additionally, the wide use of chemical pesticides can result in the development of resistant insect varieties. Lastly, the underground feeding preferences of corn rootworm larvae can make it difficult to apply rescue treatments of insecticides. Therefore, most insecticide applications are made prophylactically at the time of planting which results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have been applied to crop plants with satisfactory results against insect pests. The δ-endotoxins are proteins held within a crystalline matrix that are known to possess insecticidal activity when ingested by certain orders and species of plant pests, including insects, but are harmless to plants and other non-target organisms. Several native Cry proteins from *Bacillus thuringiensis*, or engineered Cry proteins, have been expressed in transgenic crop plants to control certain Lepidopteran and Coleopteran insect pests as an alternative to or complement to chemical pesticides. Transgenic corn hybrids that control corn rootworm have been available commercially in the US since 2003 and express toxins such as Cry3Bb1, Cry34Ab1/Cry35Ab1, modified Cry3A (mCry3A), or Cry3Ab (eCry3.1Ab).

Although the usage of transgenic plants expressing Cry proteins has been shown to be extremely effective, insect pests that now have resistance against the Cry proteins expressed in certain transgenic plants are known. Therefore, there remains a need to identify new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of insect control agents through products that minimize the burden on the environment, as through transgenic plants, are desirable.

SUMMARY

This disclosure provides polypeptides that are insecticidal against at least a coleopteran pest, e.g., against corn rootworm (WCR, *Diabrotica virgifera virgifera*) and uses of such polypeptides and related nucleic acids in compositions and methods, such as in plants or in methods of controlling a coleopteran pest.

Accordingly in some aspects, there is provided a polypeptide comprising an amino acid sequence that is at least 15% identical to SEQ ID NO:1. The invention also encompasses a polypeptide that is at least 48% identical to SEQ ID NO: 1 or at least 74% identical. Further aspects of the invention include the polypeptide that comprises any one of SEQ ID NOs: 1-7; the polypeptide that comprises any one of SEQ ID NOs: 1-3 or 5-6; the polypeptide that comprises any one of SEQ ID NOs: 8-10; the polypeptide that comprises SEQ ID NO: 11 or 12; and the polypeptide that comprises any one of SEQ ID NOs: 29-136. In some embodiments, the polypeptide is insecticidal against a coleopteran pest. In some embodiments, the polypeptide is insecticidal against a *Diabrotica* pest (e.g. *Diabrotica virgifera virgifera*).

A further aspect of the present invention is a nucleic acid sequence comprising a coding sequence that encodes the polypeptide of any of the above-mentioned embodiments. Other aspects of the invention are nucleic acids where the coding sequence comprises a nucleotide sequence that is at least 80% identical to or comprises any one of SEQ ID NOs: 13-28; nucleic acids where the coding sequence comprises a nucleotide sequence that is at least 80% identical to or comprises any one of SEQ ID NOs: 13-16; nucleic acids, where the coding sequence comprises any one of SEQ ID NOs: 17-23; nucleic acids where the coding sequence comprises any one of SEQ ID NOs: 24-26; and nucleic acids where the coding sequence comprises any one of SEQ ID NO: 27 or SEQ ID NO: 28. Another aspect of the invention is any of these nucleic acids where the coding sequence is codon optimized for expression in a plant and where the coding sequence is operably linked to a heterologous promoter, e.g., a plant-expressible heterologous promoter.

A still further aspect of the present invention are vectors comprising any of the described nucleic acid and transgenic host cells, comprising any of the described polypeptides or any of the described the nucleic acids. The present invention contemplates transgenic host cells where the transgenic host cell is a plant cell; where the plant cell is a monocot cell; and where the plant cell is a maize cell. An additional aspect of the present invention are transgenic host cells where the transgenic host cell is a bacterial cell. The present invention contemplates transgenic host cells where the bacterial cells is an *Agrobacterium, Bacillus,* or an *Escherichia coli* cell.

Additional aspects of the present invention are a composition comprising any of the described polypeptides and compositions of the described polypeptides further comprising an agriculturally acceptable carrier. A still further aspect of the present invention are plants comprising any of the described polypeptides or comprising any of the described nucleic acids. The present invention contemplates that these plants are monocots and these plants are maize plants. A further aspect of the presentation invention are seeds of any of the described plants and cells of any of the described plants.

The present invention also provides a method of producing a transgenic plant, the method comprising the steps of introducing into a plant cell any of the described nucleic acids, selecting a plant cell comprising the nucleic acid; and regenerating a plant from the selected plant cell. Also provided is a method for producing a transgenic plant with enhanced insecticidal properties, comprising the steps of sexually crossing a first parent plant with a second parent plant, where the first or second parent plant is any of the described plants and selecting a first generation progeny plant with enhanced insecticidal properties, wherein the selected progeny plant comprises the nucleic acid molecule. A further aspect of the present invention is a method for producing a transgenic plant with enhanced insecticidal properties, further comprising the steps of selfing the first generation progeny plant, thereby producing a plurality of second generation progeny plants; and selecting from the second generation progeny plants a plant with enhanced insecticidal properties, wherein the selected second generation progeny plants comprise the nucleic acid molecule.

The invention is also related to methods of controlling a coleopteran pest comprising delivering to the pest or an environment thereof any of the described polypeptides. In some embodiments, the coleopteran pest is Western corn rootworm (*D. virgifera virgifera*). Aspects of these methods are when the polypeptide is delivered by feeding and further aspects are when the feeding comprises the pest feeding on a plant part that comprises the described polypeptide. The present invention also contemplates the use of the sequence of any of SEQ ID NOs: 1 to 137 in a bioinformatic analysis to identify an insecticidal protein and the use of a polypeptide comprising any of the amino acid sequences of any one of SEQ ID NOs: 1-12 or 29-136 in an insect bioassay to identify an insecticidal protein (e.g. insecticidal against Western corn rootworm (*D. virgifera virgifera*)).

BRIEF DESCRIPTION OF THE SEQUENCES IN THE SEQUENCE LISTING

SEQ ID NO:1 is the amino acid sequence of ITD-46.

SEQ ID NO:2 is the amino acid sequence of *Pseudomonas* sp. OF001 (ITD-46 orthologue).

SEQ ID NO:3 is the amino acid sequence of a *Methanosarcinaceae archaeon* ITD-46 orthologue.

SEQ ID NO:4 is the amino acid sequence of *Burkholderia* sp. ABCPW14 (ITD-46 orthologue).

SEQ ID NO:5 is the amino acid sequence of a ITD-46 orthologue of an *Acidobacteria bacterium.*

SEQ ID NO:6 is the amino acid sequence of *Methanosarcina* sp. MTP4 (ITD-46 orthologue).

SEQ ID NO:7 is the amino acid sequence of a ITD-46 orthologue of *Streptomyces hainanensis.*

SEQ ID NO:8 is the amino acid sequence of ITD-46_Nterm_mod1.

SEQ ID NO:9 is the amino acid sequence of ITD-46_Nterm_mod2

SEQ ID NO: 10 is the amino acid sequence of ITD-46_Cterm_mod1.

SEQ ID NO:11 is the amino acid sequence of a Methanosarcinaceae-ITD-46 chimera.

SEQ ID NO:12 is the amino acid sequence of an ITD-46-Methanosarcinaceae chimera.

SEQ ID NO: 13 is a nucleotide sequence of *Pseudomonas* sp. OF001.

SEQ ID NO:14 is a nucleotide sequence of *Burkholderia* sp. ABCPW14 (ITD-46 orthologue).

SEQ ID NO:15 is a nucleotide sequence of *Methanosarcina* sp. MTP4 (ITD-46 orthologue).

SEQ ID NO:16 is a nucleotide sequence of a ITD-46 orthologue of *Streptomyces hainanensis.*

SEQ ID NO:17 is an *E. coli* codon optimized nucleotide sequence of ITD-46.

SEQ ID NO:18 is an *E. coli* codon optimized nucleotide sequence of *Pseudomonas* sp. OF001.

SEQ ID NO:19 is an *E. coli* codon optimized nucleotide sequence of a *Methanosarcinaceae archaeon* ITD-46 orthologue.

SEQ ID NO:20 is an *E. coli* codon optimized nucleotide sequence of *Burkholderia* sp. ABCPW14 (ITD-46 orthologue).

SEQ ID NO:21 is an *E. coli* codon optimized nucleotide sequence of an ITD-46 orthologue of an *Acidobacteria bacterium.*

SEQ ID NO:22 is an *E. coli* codon optimized nucleotide sequence of *Methanosarcina* sp. MTP4 (ITD-46 orthologue).

SEQ ID NO:23 is an *E. coli* codon optimized nucleotide sequence of an ITD-46 orthologue of *Streptomyces hainanensis.*

SEQ ID NO:24 is an *E. coli* codon optimized nucleotide sequence of ITD-46_Nterm_mod1.

SEQ ID NO:25 is an *E. coli* codon optimized nucleotide sequence of ITD-46_Nterm_mod2.

SEQ ID NO:26 is *E. coli* codon optimized nucleotide sequence of ITD-46_Cterm_mod1.

SEQ ID NO:27 is an *E. coli* codon optimized nucleotide sequence of a Methanosarcinaceae-ITD-46 chimera.

SEQ ID NO:28 is an *E. coli* codon optimized nucleotide sequence of an ITD-46-Methanosarcinaceae chimera.

SED ID NOs: 29-135 are amino acid sequences of the ITD-46 Alanine scanning variants.

SEQ ID NO: 136 is the amino acid sequence of a *Methanosarcina* sp. DH2 Nterm_fixed variant.

SEQ ID NO: 137 is an *E. coli* codon optimized nucleotide sequence of *Methanosarcina* sp. DH2 Nterm_fixed variant.

DETAILED DESCRIPTION

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments, any feature or combination of features set forth herein can be excluded or omitted. In addition, numerous variations and additions to the various embodiments suggested herein will be apparent to those skilled in the art in light of the instant disclosure, which do not depart from the instant disclosure. Hence, the following descriptions are intended to illustrate some particular embodiments of the disclosure, and not to exhaustively specify all permutations, combinations, and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties for the teachings relevant to the sentence and/or paragraph in which the reference is presented.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

For clarity, certain terms used in the specification are defined and presented as follows:

As used herein and in the appended claims, the singular forms "a," "an," and "the" include plural reference unless the context clearly dictates otherwise. Thus, for example, reference to "a plant" is a reference to one or more plants and includes equivalents thereof known to those skilled in the art, and so forth.

As used herein, the word "and/or" refers to and encompasses any and all possible combinations of one or more of the associated listed items, as well as the lack of combinations when interpreted in the alternative, "or."

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means+1° C., preferably +0.5° C. Where the term "about" is used in the context of this disclosure (e.g., in combinations with temperature or molecular weight values) the exact value (i.e., without "about") is preferred.

As used herein, phrases such as "between about X and Y", "between about X and about Y", "from X to Y" and "from about X to about Y" (and similar phrases) should be interpreted to include X and Y, unless the context indicates otherwise.

Units, prefixes and symbols may be denoted in their SI accepted form. Unless otherwise indicated, nucleic acids are written left to right in 5' to 3' orientation; amino acid sequences are written left to right in N-terminus to C-terminus orientation, respectively. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Activity" of the insecticidal proteins of the disclosure is meant that the insecticidal proteins function as orally active insect control agents, have a toxic effect (e.g., inhibiting the ability of the insect pest to survive, grow, and/or reproduce), and/or are able to disrupt or deter insect feeding, which may or may not cause death of the insect. When an insecticidal protein of the disclosure is delivered to the insect, the result is typically death of the insect, or the insect does not feed upon the source that makes the insecticidal protein available to the insect. "Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked, or situated such that the regulatory DNA sequence will affect the expression level of the coding or structural DNA sequence.

A "coding sequence" is a nucleic acid sequence that is transcribed into RNA such as mRNA, rRNA, tRNA, snRNA, sense RNA or antisense RNA which is then preferably translated in an organism to produce a protein.

As used herein, a "codon optimized" sequence means a nucleotide sequence wherein the codons are chosen to reflect the particular codon bias that a host cell or organism may have. This is typically done in such a way so as to preserve the amino acid sequence of the polypeptide encoded by the nucleotide sequence to be optimized. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, which is incorporated herein by reference. In embodiments, the polynucleotides of the disclosure are codon-optimized for expression in a plant cell (e.g., a dicot cell or a monocot cell) or bacterial cell.

To "control" insects means to inhibit, through a toxic effect, the ability of insect pests to survive, grow, feed, and/or reproduce, and/or to limit insect-related damage or loss in crop plants and/or to protect the yield potential of a crop when grown in the presence of insect pests. To "control" insects may or may not mean killing the insects, although it preferably means killing the insects. In some embodiments of the disclosure, "control" of the insect means killing the insects.

The terms "comprises", "comprising, "includes", "including", "having" and their conjugates mean including "but not limited to". These terms specify the presence of stated features, integers, steps, operations, elements, or components, but do not preclude the presence or addition of one or more other features, integers, steps, operations, elements, components, or groups thereof. The term "consisting of" means "including and limited to".

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed disclosure. Thus, the term "consisting essentially of" when used in a claim of this disclosure is not intended to be interpreted to be equivalent to "comprising."

In the context of the disclosure, "corresponding to" or "corresponds to" means that when the amino acid sequences of a reference sequence are aligned with a second amino acid sequence (e.g. variant or homologous sequences), different from the reference sequence, the amino acids that "correspond to" certain enumerated positions in the second amino acid sequence are those that align with these positions in the reference amino acid sequence but that are not necessarily in the exact numerical positions relative to the particular reference amino acid sequence of the disclosure.

To "deliver" or "delivering" a composition or an insecticidal protein means that the composition or insecticidal protein comes in contact with an insect, which facilitates the oral ingestion of the composition or insecticidal protein, resulting in a toxic effect and control of the insect. The composition or insecticidal protein may be delivered in many recognized ways, e.g., through a transgenic plant expressing the insecticidal protein, formulated protein composition(s), sprayable protein composition(s), a bait matrix, or any other art-recognized toxin delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

An "engineered" protein of the disclosure refers to a protein that has a sequence that is different at at least one amino acid position compared to at least one corresponding parent protein. An engineered protein can be a mutant protein that contains, e.g., one or more modifications such as deletions, additions, and/or substitutions of one or more amino acid positions relative to a parent protein. An engineered protein can be a chimeric protein and contain, e.g., one or more swapped or shuffled domains or fragments from at least two parent proteins.

"Effective insect-controlling amount" means that concentration of an insecticidal protein that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects. A transgenic plant with "enhanced insecticidal properties" is a plant that is expresses a protein or proteins at effective insect-controlling amounts, so that, in some embodiments, the plant is insecticidal to an increased range of insect species, relative to a plant of the same kind which is not transformed. This increased range of insect species includes insect plant pests, such as coleopteran insect pests, e.g., *Diabrotica virgifera virgifera* (Western corn rootworm).

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence of interest may be chimeric, meaning that at least one of its components is heterologous with respect to at least one of its other components. An expression cassette may also be one that comprises a native promoter driving its native gene; however, it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of this disclosure.

The term "expression" when used with reference to a polynucleotide, such as a gene, ORF or portion thereof, or a transgene in plants, refers to the process of converting genetic information encoded in a gene into RNA (e.g., mRNA, IRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to a plant, confers upon the plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to plants for the production of commercially valuable enzymes or metabolites in the plant.

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the disclosure, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

The terms "increase", "increasing", "increased", "enhance", "enhanced", "enhancing", and "enhancement" and similar terms, as used herein, describe an elevation in control of a plant pest, e.g., by contacting a plant with a polypeptide of the disclosure (such as, for example, by transgenic expression or by topical application methods). The increase in control can be in reference to the level of control of the plant pest in the absence of the polypeptide of the disclosure (e.g., a plant that is not transgenically expressing the polypeptide or is not topically treated with the polypeptide). Thus in embodiments, the terms "increase", "increasing", "increased", "enhance", "enhanced", "enhancing", and "enhancement" and similar terms can indicate an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more as compared to a suitable control (e.g., a plant, plant part, plant cell that is not contacted with the polypeptide of the disclosure).

The term "identity" or "identical" in the context of two nucleic acid or amino acid sequences, refers to the percentage of identical nucleotides or amino acids in a linear polynucleotide or amino acid sequence of a reference ("query") sequence (or its complementary strand) as compared to a test ("subject") sequence when the two sequences are globally aligned. Unless otherwise stated, sequence identity as used herein refers to the value obtained using the Needleman and Wunsch algorithm ((1970) J. Mol. Biol. 48:443-453) implemented in the EMBOSS Needle alignment tool using default matrix files EBLOSUM62 for protein with default parameters (Gap Open=10, Gap Extend=0.5, End Gap Penalty=False, End Gap Open=10, End Gap Extend=0.5) or DNAfull for nucleic acids with default parameters (Gap Open=10, Gap Extend=0.5, End Gap Penalty=False, End Gap Open=10, End Gap Extend=0.5); or any equivalent program thereof. EMBOSS Needle is available, e.g., from EMBL-EBI such as at the following website: ebi.ac.uk/Tools/psa/emboss_needle/and as described in the following publication: "The EMBL-EBI search and sequence analysis tools APIs in 2019." Madeira et al. Nucleic Acids Research, June 2019, 47 (W1): W636-W641. The term "equivalent program" as used herein refers to any sequence comparison program that, for any two sequences in question, generates an alignment having identical nucleotide or amino acid residue matches and an identical percent sequence identity when compared to the corresponding alignment generated by EMBOSS Needle. In some embodiments, substantially identical nucleic acid or amino acid sequences may perform substantially the same function.

"Insecticidal" as used herein is defined as a toxic biological activity capable of controlling an insect pest, optionally but preferably by killing them.

In some embodiments, the polynucleotides or polypeptides of the disclosure are "isolated". The term "isolated" polynucleotide or polypeptide is a polynucleotide or polypeptide that no longer exists in its natural environment. An isolated polynucleotide or polypeptide of the disclosure may exist in a purified form or may exist in a recombinant host such as in a transgenic bacteria or a transgenic plant. Therefore, for example, a claim to an "isolated" polynucleotide or polypeptide encompasses a nucleic acid molecule when the nucleic acid molecule is comprised within a transgenic plant genome.

The term "isolated", when used in the context of the nucleic acid molecules or polynucleotides of the present disclosure, refers to a polynucleotide that is identified within and isolated/separated from its chromosomal polynucleotide context within the respective source organism. An isolated nucleic acid or polynucleotide is not a nucleic acid as it occurs in its natural context, if it indeed has a naturally occurring counterpart. In contrast, non-isolated nucleic acids are nucleic acids such as DNA and RNA, which are found in the state they exist in nature. For example, a given polynucleotide (e.g., a gene) is found on the host cell chromosome in proximity to neighboring genes. The isolated nucleic acid molecule may be present in single-stranded or double-stranded form. Alternatively, it may contain both the sense and antisense strands (i.e., the nucleic acid molecule may be double-stranded). In some embodiments, the nucleic acid molecules of the present disclosure are isolated.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

A "native" or "wild type" nucleic acid, polynucleotide, nucleotide sequence, polypeptide or amino acid sequence refers to a naturally occurring or endogenous nucleic acid, polynucleotide, nucleotide sequence, polypeptide or amino acid sequence.

A "nucleic acid molecule" or "nucleic acid" is a segment of single-stranded, double-stranded or partially double-stranded DNA or RNA, or a hybrid thereof, that can be isolated or synthesized from any source. In the context of the present disclosure, the nucleic acid molecule is typically a segment of DNA. In some embodiments, the nucleic acid molecules of the disclosure are isolated nucleic acid molecules. In some embodiments, the nucleic acid molecules of the disclosure are comprised within a vector, a plant, a plant cell or a bacterial cell. The terms also include reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A nucleic acid molecule can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "nucleic acid," "nucleic acid molecule," and "polynucleotide" are used interchangeably herein.

"Operably linked" refers to the association of polynucleotides on a single nucleic acid molecule so that the function of one affects the function of the other. For example, a promoter is operably linked with a coding polynucleotide when it is capable of affecting the expression of that coding polynucleotide (i.e., that the coding polynucleotide is under the transcriptional control of the promoter). Coding polynucleotide in sense or antisense orientation can be operably linked to regulatory polynucleotides.

As used herein "pesticidal," insecticidal," and the like, refer to the ability of proteins of the disclosure to control a pest organism or an amount of one or more proteins of the disclosure that can control a pest organism.

The term "plant" includes reference to whole plants, plant organs, plant tissues (e.g., leaves, stems, roots, etc., seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the disclosure, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is maize.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes, and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like. Any tissue of a plant in planta or in culture is included in the term "plant tissue.".

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein "plant sample" or "biological sample" refers to either intact or non-intact (e.g. milled seed or plant tissue, chopped plant tissue, lyophilized tissue) plant tissue. It may also be an extract comprising intact or non-intact seed or plant tissue. The biological sample or extract may be selected from the group consisting of corn flour, corn meal, corn syrup, corn oil, corn starch, and cereals manufactured in whole or in part to contain corn by-products.

A "polynucleotide of interest" or "nucleic acid of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of a commercially valuable enzyme or metabolite, an altered reproductive capability, and the like.

A "portion" or a "fragment" of a polypeptide of the disclosure will be understood to mean an amino acid sequence or nucleic acid sequence of reduced length relative to a reference amino acid sequence or nucleic acid sequence of the disclosure. Such a portion or a fragment according to the disclosure may be, where appropriate, included in a larger polypeptide or nucleic acid of which it is a constituent (e.g., a tagged or fusion protein or an expression cassette). In embodiments, the "portion" or "fragment" substantially retains the activity, such as insecticidal activity (e.g., at least 40%, 50%, 60%, 70%, 80%, 85%, 90%, 95% or even 100% of the activity) of the full-length protein or nucleic acid, or has even greater activity, e.g., insecticidal activity, than the full-length protein).

The terms "protein," "peptide," and "polypeptide" are used interchangeably herein.

The term "promoter," as used herein, refers to a polynucleotide, usually upstream (5') of the translation start site of a coding sequence, which controls the expression of the coding sequence by providing the recognition for RNA polymerase and other factors required for proper transcription. For example, a promoter may contain a region containing basal promoter elements recognized by RNA polymerase, a region containing the 5' untranslated region (UTR) of a coding sequence, and optionally an intron.

As used herein, the term "recombinant" refers to a form of nucleic acid (e.g., DNA or RNA) or protein or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized, for example, a polynucleotide synthesize using an assembled nucleotide sequence, and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. Another example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule which may be incorporated into its genome. As a result of such genomic alteration, the recombinant plant is distinctly different from the related wild-type plant. A "recombinant" bacteria is a bacteria not found in nature that comprises a heterologous nucleic acid molecule. Such a bacteria may be created by transforming the bacteria with the nucleic acid molecule or by the conjugation-like transfer of a plasmid from one bacteria strain to another, whereby the plasmid comprises the nucleic acid molecule.

The terms "reduce," "reduced," "reducing," "reduction," "diminish," and "suppress" (and grammatical variations thereof) and similar terms, as used herein, refer to a decrease in the survival, growth and/or reproduction of a plant pest, e.g., by contacting a plant with a polypeptide of the disclosure (such as, for example, by transgenic expression or by topical application methods). This decrease in survival, growth and/or reproduction can be in reference to the level observed in the absence of the polypeptide of the disclosure (e.g., a plant that is not transgenically expressing the polypeptide or is not topically treated with the polypeptide). Thus, in embodiments, the terms "reduce," "reduced," "reducing," "reduction," "diminish," and "suppress" (and grammatical variations thereof) and similar terms mean a decrease of at least about 5%, 10%, 15%, 20%, 25%, 30%, 35%, 40%, 45%, 50%, 55%, 60%, 65%, 70%, 75%, 80%, 85%, 90%, 95% or more as compared with a plant that is not contacted with a polypeptide of the disclosure (e.g., a plant that is not transgenically expressing the polypeptide or is not topically treated with the polypeptide). In representative embodiments, the reduction results in no or essentially no (i.e., an insignificant amount, e.g., less than about 10%, less than about 5% or even less than about 1%) detectable survival, growth and/or reproduction of the plant pest.

"Regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, terminators, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones).

As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait).

"Synthetic" refers to a nucleotide sequence comprising bases or a structural feature(s) that is not present in the natural sequence. For example, an artificial sequence encoding a protein of the disclosure that resembles more closely the G+C content and the normal codon distribution of dicot or monocot plant genes is said to be synthetic.

As used herein, a protein of the disclosure that is "toxic" to an insect pest is meant that the protein functions as an orally active insect control agent to kill the insect pest, or the protein is able to disrupt or deter insect feeding, or causes growth inhibition to the insect pest, both of which may or may not cause death of the insect. When a toxic protein of the disclosure is delivered to an insect or an insect comes into oral contact with the toxic protein, the result is typically death of the insect, or the insect's growth is slowed, or the insect stops feeding upon the source that makes the toxic protein available to the insect.

"Transformation" is a process for introducing heterologous nucleic acid into a host cell or organism. In particular embodiments, "transformation" means the stable integration of a DNA molecule into the genome (nuclear or plastid) of an organism of interest. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof. Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

"Transformed" and "transgenic" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term "transgenic plant" includes reference to a plant into which a heterologous nucleic acid molecule has been introduced. Generally, the heterologous nucleic acid sequence is stably integrated within the genome such that the nucleic acid sequence is passed on to successive generations. The heterologous nucleic acid sequence may be integrated into the genome alone or as part of a recombinant expression cassette. "Transgenic" is used herein to include any cell, cell line, callus, tissue, plant part or plant, the genotype of which has been altered by the presence of a heterologous nucleic acid sequence, including those transgenics initially so altered as well as those created by sexual crosses or asexual propagation from the initial transgenic.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Example vectors include a plasmid, cosmid, phagemid, artificial chromosome, phage or viral vector.

Insecticidal Proteins, Polypeptides, Nucleic Acids

The present disclosure provides novel insecticidal proteins which have activity against Coleopterans, for example, *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm), and/or other Coleopteran insect pests such as Colorado Potato Beetle. The present disclosure also relates to nucleic acids whose expression results in insecticidal proteins of the disclosure, and to the making and using of the insecticidal proteins to control insect pests. In embodiments, the expression of the nucleic acids results in insecticidal proteins that can be used to control Coleopteran insects such as western, northern and/or southern corn rootworm, particularly when expressed in a transgenic plant such as a transgenic corn plant.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO:1. In some embodiments, the polypeptide comprises SEQ ID NO:1.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO:2. In some embodiments, the polypeptide comprises SEQ ID NO:2.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO:3. In some embodiments, the polypeptide comprises SEQ ID NO:3.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO:4. In some embodiments, the polypeptide comprises SEQ ID NO:4.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO:5. In some embodiments, the polypeptide comprises SEQ ID NO:5.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 6. In some embodiments, the polypeptide comprises SEQ ID NO: 6.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 7. In some embodiments, the polypeptide comprises SEQ ID NO: 7.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 8. In some embodiments, the polypeptide comprises SEQ ID NO: 8.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 9. In some embodiments, the polypeptide comprises SEQ ID NO: 9.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 10. In some embodiments, the polypeptide comprises SEQ ID NO: 10.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 11. In some embodiments, the polypeptide comprises SEQ ID NO: 11.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to SEQ ID NO: 12. In some embodiments, the polypeptide comprises SEQ ID NO: 12.

The present disclosure provides a polypeptide comprising an amino acid sequence that has at least 30% sequence identity (at least 35%, at least 40%, at least 45%, at least 50%, at least 55%, at least 60%, at least 65%, at least 70%, at least 75, at least 80%, at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% sequence identity) to any one of SEQ ID NOs: 29-136.

In another embodiment, the present disclosure provides a polypeptide comprising an amino acid sequence that comprises any one of SEQ ID NOs: 1-7. In another embodiment, the polypeptides comprise any one of SEQ ID NOs: 1-3 or 5-6. In another embodiment, the polypeptides comprise any one of SEQ ID Nos: 8-10. In another embodiment, the polypeptides comprise any one of SEQ ID NOs: 11 or 12. In another embodiment, the polypeptides comprise any one of SEQ ID Nos: 29-136.

Certain of the sequences disclosed herein are orthologues of each other and have a certain percent identity to each other. Those percent identities are disclosed in Table 1.

Dietary exposure is the major route by which humans can be exposed to insecticidal proteins expressed in transgenic plants. Acute oral mammalian toxicity and protein digestibility are the end points for EPA's human health risk assessment. Further scientific evidence of the safety of insecticidal proteins is that they have been shown to be rapidly degraded in vitro using simulated gastric fluids. For example, results of seven in vitro assays conducted with representative Cry1, Cry2, and Cry3 proteins establish that the proteins are rapidly degraded, typically within 30 seconds. These results support the broader conclusion that members of these groups of Cry proteins (that share significant amino acid sequence identity) are likely to be rapidly degraded following ingestion by humans. Similar tests are done for each transgenic protein expressed in plants. Another area of consideration is whether insecticidal proteins may induce an allergenic reaction. Demonstrated rapid in vitro degradation of the transgenic insecticidal protein should minimize the potential for such an occurrence. By comparison, food allergens generally persist in the in vitro gastrointestinal model, whereas common food proteins with no allergenic history degraded rapidly in simulated gastric fluid (Metcalfe et al. 1996).

A simulated gastric fluid (SGF) assay measures the in vitro digestibility of a test protein at tightly controlled conditions representative of the upper mammalian digestive tract. For example, bacterially produced test Cry protein (at a concentration of 0.5-5 mg/ml) was exposed to the enzyme pepsin (from porcine gastric mucosa, solubilized in 2 mg/ml NaCl, pH 1.2) at a ratio of 10 Units of pepsin activity/µg test protein over a time period of one hour at 37° C. Samples were removed at 1, 2, 5, 10, 30, and 60 minute timepoints and immediately quenched with the addition of pre-heated (95° C.-2 minutes) stop buffer (65% 0.5M Sodium Bicarbonate pH 11, 35% Tricine Loading Buffer) to immediately render pepsin inactive, and returned to heat for an additional 5 minutes. Once the assay was complete, time point samples and controls (test protein alone, pepsin alone) were examined by SDS-PAGE on a 10-20% Tris-Tricine gel (with peptides visible down to 1 kDa) to track the kinetics and level of digestion performed by pepsin. If the test protein or a significant polypeptide fragment of the text protein is visible at, for example, the 5 and/or 10 minute timepoints, then it is not digestible or not completely digestible by the SGF assay, and may be scored qualitatively as "no", or "not digestible". If the test protein and any significant polypeptide fragment is not visible at, for example, the 5 minute timepoint, then it is digestible by the SGF assay, and may be scored qualitatively as "yes" or "digestible".

The disclosed insecticidal proteins may therefore, in some embodiments, be modified to improve digestibility. For example, the disclosed insecticidal proteins may additionally comprise introduced protease cleavage sites and/or cysteine substitutions. The introduced protease cleavage site(s) and/or cysteine substitution(s) are not naturally occurring, and are introduced into the polypeptide sequence, as a substitution mutation or as an insertion or deletion mutation, or some combination thereof. The introduced protease cleavage site(s) may be introduced by the insertion of at least one leucine residue in a polypeptide sequence. In some embodiments, the polypeptides comprise cysteine substitution(s), e.g., substitution of cysteine with another amino acid such as alanine or leucine. The introduced mutation(s) may destabilize the polypeptide, so that a protease may gain access to a cleavage site which it previously did not have access to due to tight and/or stable folding of the protein, or to steric hindrance. The introduced protease cleavage site(s) may be an introduced mutation in the polypeptide sequence which is recognized by a protease, such as chymotrypsin, trypsin, or pepsin, as a site for proteolytic cleavage.

In some embodiments, the introduced protease cleavage site(s) may alter an existing protease cleavage site so that it is recognized by a different protease. Protease cleavage sites for chymotrypsin, trypsin, and pepsin are well-known in the art. Chymotrypsin preferentially cleaves peptide amide bonds where the carboxyl side of the amide bond (the P1 position) is a large hydrophobic amino acid (tyrosine, tryptophan, and phenylalanine). Trypsin cleaves peptide chains mainly at the carboxyl side of the amino acids lysine or arginine, except when either is followed by proline. Pepsin is most efficient in cleaving peptide bonds between hydrophobic and preferably aromatic amino acids such as phenylalanine, tryptophan, tyrosine, and leucine. These cleavage sites are the preferential cleavage sites and do not include all cleavage sites recognized by chymotrypsin, trypsin, or pepsin, and furthermore do not include all cleavage sites for all proteases.

It is well-known in the art that cysteines in proteins are frequently covalently bonded to other cysteine residues to form disulfide bonds. Disulfide bonds play an important role in the folding and stability of some proteins. The ITD-46 variant may have an altered or less stable tertiary structure compared to wild-type ITD-46. For example, the introduced mutation may "loosen" the three dimensional folding of the ITD-46 polypeptide, thereby making a protease cleavage site that was previously inaccessible (and therefore not cleaved) accessible to a protease. This results in the introduced mutation introducing a protease cleavage site that did not exist in the unaltered polypeptide. In preferred embodiments, the mutation does not alter or does not significantly alter the activity, or the insecticidal activity, of the polypeptide against coleopteran pests.

The disclosed insecticidal proteins have activity against coleopteran pests. In some embodiments, the insecticidal protein(s) has/have activity against one or more of the following non-limiting examples of a Coleopteran pest: *Diabrotica* spp. such as *D. barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (cucurbit beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata and/or D. viridula; Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and/or *E. cucumeris* (potato flea beetle); *Phyllotreta* spp. such as *P. cruciferae* (crucifer flea beetle) and/or *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); or any combination of the foregoing.

According to the foregoing embodiments, the disclosed proteins can optionally have insecticidal activity against a Western corn rootworm insect pest or colony that has resistance to another insecticidal agent, including another insecticidal protein (such as, e.g. a Bt protein). In embodiments, the engineered insecticidal protein has insecticidal activity against a Western corn rootworm colony that is resistant to an engineered Cry3 protein (e.g. eCry3.1Ab, including without limitation maize event 5307 or mCry3A, including without limitation maize event MIR604 or Cry3Bb1 including without limitation in maize event MON87411 or MON88017) and/or resistant to another Cry protein (e.g., a Cry34 or Cry35 protein including without limitation in maize event DAS-59122-7 or DP-004114-3) and/or resistant to any other insecticidal protein (e.g., present in a maize event) that is meant to control Western corn rootworm.

In some embodiments, the insecticidal proteins of the invention are active against Lepidopteran insects. A person skilled in the art will appreciate that a protein of the present invention may have a different range of insecticidal activity compared to other proteins of the invention.

In some embodiments, the insecticidal protein(s) has/have activity against one or more of the following non-limiting examples of a Lepidopteran pest: *Spodoptera* spp. such as *S.*

*frugiperda* (fall armyworm), *S. littoralis* (Egyptian cotton leafworm), *S. ornithogalli* (yellowstriped armyworm), *S. praefica* (western yellowstriped armyworm), *S. eridania* (southern armyworm), *S. litura* (Common cutworm/Oriental leafworm), *S. cosmioides* (black armyworm), *S. exempta* (African armyworm), *S. mauritia* (lawn armyworm) and/or *S. exigua* (beet armyworm); *Ostrinia* spp. such as *O. nubilalis* (European corn borer) and/or *O. furnacalis* (Asian corn borer); *Plutella* spp. such as *P. xylostella* (diamondback moth); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm/soybean podworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or *D. saccharalis* (sugarcane borer); *Trichoplusia* spp. such as *T. ni* (cabbage looper); *Sesamia* spp. such as *S. nonagroides* (Mediterranean corn borer), *S. inferens* (Pink stem borer) and/or *S. calamistis* (pink stem borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. such as *C. includens* (soybean looper); *Feltia* spp. such as *F. ducens* (dingy cutworm); *Chilo* spp. such as *C. suppressalis* (striped stem borer), *C. Agamemnon* (oriental corn borer), and *C. partellus* (spotted stalk borer), *Cnaphalocrocis* spp. such as *C. medinalis* (rice leaffolder), *Conogethes* spp. such as *C. punctiferalis* (Yellow peach moth), *Mythimna* spp. such as *M. separata* (Oriental armyworm), *Athetis* spp. such as *A. lepigone* (Two-spotted armyworm), *Busseola* spp. such as *B. fusca* (maize stalk borer), *Etiella* spp. such as *E. zinckenella* (pulse pod borer), *Leguminivora* spp. such as *L. glycinivorella* (soybean pod borer), *Matsumuraeses* spp. such as *M. phaseoli* (adzuki pod worm), *Omiodes* spp. such as *O. indicata* (Soybean leaffolder/Bean-leaf webworm), *Rachiplusia* spp. such as *R. nu* (sunflower Looper), or any combination of the foregoing.

The disclosed insecticidal proteins may also be active against Hemipteran, Dipteran, *Lygus* spp., and/or other piercing and sucking insects, for example of the order Orthoptera or Thysanoptera. Insects of the order Hemiptera include but are not limited to Chinavia *hilaris* (green stink bug); *Anasa tristis De Geer* (squash bug); *Blissus leucopterus* (chinch bug); *Corythuca gossypii Fabricius* (cotton lace bug); *Cyrtopeltis modesta* Distant (tomato bug); *Dysdercus suturellus* Hern ch-Schaffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis Linnaeus* (common meadow bug); *L.*

*rugulipennis* Poppius (European tarnished plant bug); *Lygocoris pabulinus Linnaeus* (common green capsid); *Nezara viridula Linnaeus* (southern green stink bug); *Oebalus pugnax Fabricius* (rice stink bug); *Oncopeltus fasciatus* Dallas (large milkweed bug); *Pseudatomoscelis seriatus* Reuter (cotton fleahopper), *Calocoris norvegicus* Gmelin (strawberry bug); Orthops *campestris Linnaeus; Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus Fabricius* (four-lined plant bug); *Nysius ericae* Schilling (false chinch bug); *Nysius raphanus* Howard (false chinch bug); *Nezara viridula Linnaeus* (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp. Insects in the order Diptera include but are not limited *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcorn maggot), *D. brassicae* (cabbage maggot) and *D. radicum* (cabbage root fly); *Psila* spp. such as *P. rosae* (carrot rust fly); *Tetanops* spp. such as *T. myopaeformis* (sugarbeet root maggot); and any combination of the foregoing. Insects in the order Orthoptera include but are not limited *Melanoplus* spp. such as *M. differentialis* (Differential grasshopper), *M. femurrubrum* (Redlegged grasshopper), *M. bivittatus* (Twostriped grasshopper); and any combination thereof. Insects in the order Thysanoptera include but are not limited *Frankliniella* spp. such as *F. occidentalis* (western flower *thrips*) and *F. fusca* (tobacco *thrips*); and *Thrips* spp. such as *T. tabaci* (onion *thrips*), *T. palmi* (melon *thrips*); and any combination of the foregoing.

The disclosed insecticidal protein(s) may also have insecticidal activity against any one or more of the following: Phyllophaga spp., *Rhopalosiphum maidis, Pratylenchus penetrans, Melanotus cribulosus, Cyclocephala lurida, Limonius californicus, Tetranychus urticae, Haplothrips aculeatus, Tetranychus truncates, Anomala corpulenta, Oedaleus infernalis, Frankliniella tenuicornis, Tetranychus cinnabarinus, Aiolopus thalassinus tamulus, Trachea tokionis, Laodelphax striatellus, Holotrichia oblita, Dichelops furcatus, Diloboderus abderu, Dalbulus maidis, Astylus variegathus, Scaptocoris castanea, Locusta migratoria manilensis, Agriotes lineatus, Peregrinus maidis, Oscinella frit, Frankliniella williamsi, Zyginidia manaliensis, Atherigona soccata, Nicentrites testaceipes, Myllocerus undecimpustulatus, Atherigona naquii, Amsecta albistriga, Plodia interpuctella, Melanotus caudex, Microtermes* spp., *Atherigona oryzae, Tanymecus dilaticollis, Delphacodes kuschelli, Lepidiota* stigma, *Phyllophaga hellery, Tribolium castaneum, Pelopidas mathias, Oxya chinensis* (Thunberg), *Stenocranus pacificus, Scutigerella immaculata, Chrysodeixis chalcites, Euproctis* sp. (Lymantriidae), Phyllotreata spp. (*undulata*), *Reptalus panzer, Cyrtacanthacris tartarica Linnaeus, Orgyia postica, Dactylispa lameyi, Patanga succincta Johanson, Tetranychus* spp., *Calomycterus* sp., *Adoretus compressus* Weber, and *Paratetranychus stickney.*

The disclosed insecticidal proteins may also be active against nematodes. The term "nematode" as used herein encompasses any organism that is now known or later identified that is classified in the animal kingdom, phylum Nematoda, including without limitation nematodes within class Adenophorea (including for example, orders Enoplida, Isolaimida, Mononchida, Dorylaimida, Trichocephalida, Mermithida, Muspiceida, Araeolaimida, Chromadorida, Desmoscolecida, Desmodorida and Monhysterida) and/or class Secernentea (including, for example, orders Rhabdita, Strongylida, Ascaridida, Spirurida, Camallanida, Diplogasterida, Tylenchida and Aphelenchida). Nematodes include but are not limited to parasitic nematodes such as root-knot nematodes, cyst nematodes and/or lesion nematodes. Exemplary genera of nematodes according to the present invention include but are not limited to, *Meloidogyne* (root-knot nematodes), *Heterodera* (cyst nematodes), *Globodera* (cyst nematodes), *Radopholus* (burrowing nematodes), *Rotylenchulus* (reniform nematodes), *Pratylenchus* (lesion nematodes), *Aphelenchoides* (foliar nematodes), *Helicotylenchus* (spiral nematodes), *Hoplolaimus* (lance nematodes), *Paratrichodorus* (stubby-root nematodes), *Longidorus, Nacobbus* (false root-knot nematodes), *Subanguina, Belonlaimus* (sting nematodes), *Criconemella, Criconemoides* (ring nematodes), *Ditylenchus, Dolichodorus, Hemicriconemoides, Hemicycliophora, Hirschmaniella, Hypsoperine, Macroposthonia, Melinius, Punctodera, Quinisulcius, Scutellonema, Xiphinema* (dagger nematodes), *Tylenchorhynchus* (stunt nematodes), *Tylenchulus, Bursaphelenchus* (round worms), and any combination thereof.

Exemplary plant parasitic nematodes according to the present disclosure include, but are not limited to, *Belonolaimus gracilis, Belonolaimus longicaudatus, Bursaphelenchus xylophilus* (pine wood nematode), *Criconemoides ornata, Ditylenchus* destructor (potato rot nematode), *Ditylenchus dipsaci* (stem and bulb nematode), *Globodera pallida* (potato cyst nematode), *Globodera rostochiensis* (golden nematode), *Heterodera glycines* (soybean cyst nematode), *Heterodera schachtii* (sugar beet cyst nematode); *Heterodera zeae* (corn cyst nematode), *Heterodera avenae* (cereal cyst nematode), *Heterodera carotae, Heterodera trifolii, Hoplolaimus columbus, Hoplolaimus galeatus, Hoplolaimus magnistylus, Longidorus breviannulatus, Meloidogyne arenaria, Meloidogyne chitwoodi, Meloidogyne hapla, Meloidogyne incognita, Meloidogyne javanica, Mesocriconema xenoplax, Nacobbus aberrans, Naccobus dorsalis, Paratrichodorus christiei, Paratrichodorus minor, Pratylenchus brachyurus, Pratylenchus crenatus, Pratylenchus hexincisus, Pratylenchus neglectus, Pratylenchus penetrans, Pratylenchus projectus, Pratylenchus scribneri, Pratylenchus tenuicaudatus, Pratylenchus thornei, Pratylenchus zeae, Punctodera chaccoensis, Quinisulcius acutus, Radopholus similis, Rotylenchulus reniformis, Tylenchorhynchus dubius, Tylenchulus semipenetrans* (citrus nematode), *Siphinema americanum, X. Mediterraneum*, and any combination of the foregoing.

The disclosure also encompasses antibodies that specifically bind to the insecticidal proteins of the disclosure. The antibody can optionally be a monoclonal antibody or a polyclonal antisera. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as described in Harlow and Lane (1988. Antibodies a laboratory manual. pp. 726. Cold Spring Harbor Laboratory) and as in Goding (Monoclonal Antibodies: Principles & practice. 1986. Academic Press, Inc., Orlando, FL). The present disclosure also encompasses an insecticidal protein that cross-reacts with an antibody, particularly a monoclonal antibody, raised against one or more of the chimeric insecticidal proteins of the present disclosure.

The antibodies according to the disclosure are useful, e.g., in immunoassays for determining the amount or presence of a chimeric insecticidal protein of the disclosure or an antigenically related polypeptide, e.g., in a biological sample. Such assays are also useful in quality-controlled production of compositions containing one or more of the chimeric insecticidal proteins of the disclosure or an antigenically related polypeptide. In addition, the antibodies can be used to assess the efficacy of recombinant production of one or more of the chimeric proteins of the disclosure or an antigenically related polypeptide, as well as for screening expression libraries for the presence of a nucleotide sequence encoding one or more of the chimeric proteins of the disclosure or an antigenically related polypeptide. Antibodies further find use as affinity ligands for purifying or isolating any one or more of the proteins of the disclosure or an antigenically related polypeptide.

In embodiments, the nucleic acid sequences which encode the polypeptides of the disclosure are provided. In some embodiments the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 13. In other embodiments, the coding sequence comprises SEQ ID NO:13.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 14. In other embodiments, the coding sequence comprises SEQ ID NO: 14.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 15. In other embodiments, the coding sequence comprises SEQ ID NO: 15.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 16. In other embodiments, the coding sequence comprises SEQ ID NO: 16.

In some embodiments the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 17. In other embodiments, the coding sequence comprises SEQ ID NO: 17.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 18. In other embodiments, the coding sequence comprises SEQ ID NO: 18.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 19. In other embodiments, the coding sequence comprises SEQ ID NO: 19.

In some embodiments the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 20. In other embodiments, the coding sequence comprises SEQ ID NO: 20.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 21. In other embodiments, the coding sequence comprises SEQ ID NO: 21.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 22. In other embodiments, the coding sequence comprises SEQ ID NO: 22.

In some embodiments the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 23. In other embodiments, the coding sequence comprises SEQ ID NO: 23.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 24. In other embodiments, the coding sequence comprises SEQ ID NO: 24.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 25. In other embodiments, the coding sequence comprises SEQ ID NO: 25.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 26. In other embodiments, the coding sequence comprises SEQ ID NO: 26.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 27. In other embodiments, the coding sequence comprises SEQ ID NO: 27.

In some embodiments, the coding sequence is at least 80% identical to (at least 81%, at least 82%, at least 83%, at least 84%, at least 85%, at least 86%, at least 87%, at least 88%, at least 89%, at least 90%, at least 91%, at least 92%, at least 93%, at least 94, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8, or at least 99.9% identical) to SEQ ID NO: 28. In other embodiments, the coding sequence comprises SEQ ID NO: 28.

In some embodiments, the coding sequence comprises any one of SEQ ID NOs: 13-28. In other embodiments, the coding sequence comprises any one of SEQ ID NOs: 13-16. In other embodiments, the coding sequence comprises SEQ ID NOs: 17-23. In other embodiments, the coding sequence comprises SEQ ID NOs: 24-26. In other embodiments, the coding sequence comprises SEQ ID NO: 27 or SEQ ID NO: 28.

Expression Cassettes and Vectors

In some aspects, the disclosure provides expression cassettes and vectors that encode the insecticidal proteins of the disclosure. In some embodiments, coding sequences comprising synthetic nucleotide sequences that are codon optimized for expression in a plant (for example, a transgenic monocot plant host or a transgenic dicot plant host, such as a corn or soy plant). In embodiments, the nucleotide coding sequence is partially or completely synthetic. In representative embodiments, for expression in transgenic plants, such as corn or soy, the nucleotide sequences of the disclosure are modified and/or optimized. For example, although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this disclosure can be changed to conform with plant preferences, while maintaining the amino acids encoded thereby. Furthermore, it is known in the art that high expression in plants, for example corn plants, can be achieved from coding sequences that have at least about 35% GC content, or at least about 45%, or at least about 50%, or at least about 60%. Microbial nucleotide sequences that have low GC contents may express poorly in plants. Although certain nucleotide sequences can be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, in some embodiments, the nucleotide sequence is modified to remove illegitimate splice sites that may cause message truncation. Such modifications to the nucleotide sequences can be made using well known techniques of site directed mutagenesis, PCR, and synthetic gene construction using the methods described, for example, in U.S. Pat. Nos. 5,625,136; 5,500,365 and 6,013,523.

In some embodiments, the disclosure provides synthetic coding sequences or polynucleotides made according to the procedure disclosed in U.S. Pat. No. 5,625,136. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989). It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

In representative embodiments, a polynucleotide of the disclosure is an isolated polynucleotide. In embodiments, a polynucleotide of the disclosure is a recombinant polynucleotide.

In some embodiments, a heterologous promoter is operably linked to a nucleic acid comprising, consisting essentially of or consisting of a coding sequence that encodes an engineered protein of the disclosure that is toxic to a coleopteran pest. Promoters can include, for example, constitutive, inducible, temporally regulated, developmentally regulated, chemically regulated, tissue-preferred and/or tissue-specific promoters. In particular aspects, a promoter useful with the disclosure is a promoter capable of initiating transcription of a nucleotide sequence in a plant cell, e.g., in a cell of a monocot (e.g., maize or rice) or dicot (e.g., soybean, cotton) plant.

In embodiments, the heterologous promoter is a plant-expressible promoter (e.g., monocot expressible or dicto expressible). For example, without limitation, the plant-expressible promoter can be selected from the group of promoters consisting of ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, *petunia* chalcone isomerase, bean glycine rich protein 1, potato patatin, lectin, CaMV 35S and S-E9 small subunit RuBP carboxylase promoter.

Although many promoters from dicotyledons have been shown to be operational in monocotyledons and vice versa, in embodiments, dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

The choice of promoter can vary depending on the temporal and spatial requirements for expression, and also depending on the host cell to be transformed. Thus, for example, expression of the nucleotide sequences of the disclosure can be in any plant and/or plant part, (e.g., in leaves, in stalks or stems, in ears, in inflorescences (e.g., spikes, panicles, cobs, etc.), in roots, seeds and/or seedlings, and the like). For example, where expression in a specific tissue or organ is desired, a tissue-specific or tissue-preferred promoter can be used (e.g., a root specific/preferred promoter). For example, where expression is not desired in a specific tissue or organ, a tissue-free promoter can be used. In embodiments, a "pollen-free" promoter is provided which results in low or no detectable gene expression in the pollen of the target plant species. In contrast, where expression in response to a stimulus is desired a promoter inducible by stimuli or chemicals can be used. Where continuous expression at a relatively constant level is desired throughout the cells of a plant a constitutive promoter can be chosen.

Promoters useful with the disclosure include, but are not limited to, those that drive expression of a nucleotide sequence constitutively, those that drive expression when induced, and those that drive expression in a tissue- or developmentally-specific manner. These various types of promoters are known in the art.

Suitable constitutive promoters include, for example, CaMV 35S promoter (Odell et al., Nature 313:810-812, 1985); *Arabidopsis* At6669 promoter (see PCT Publication No. WO04081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2 (6): 837-44, 1992); ubiquitin (Christensen et al., Plant Mol. Biol. 18:675-689, 1992); Rice cyclophilin (Bucholz et al., Plant Mol Biol. 25 (5): 837-43, 1994); Maize H3 histone (Lepetit et al., Mol. Gen. Genet. 231:276-285, 1992); Actin 2 (An et al., Plant J. 10 (1); 107-121, 1996), constitutive root tip CT2 promoter (see PCT application No. IL/2005/000627) and Synthetic Super MAS (Ni et al., The Plant Journal 7:661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Tissue-specific or tissue-preferential promoters useful for the expression of the polypeptides of the disclosure in plants, optionally maize, include those that direct expression in root, pith, leaf or pollen. Suitable tissue-specific promoters include, but not limited to, leaf-specific promoters (such as described, for example, by Yamamoto et al., Plant J. 12:255-

265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993), seed-preferred promoters (e.g., from seed specific genes; Simon, et al., Plant Mol. Biol. 5. 191, 1985; Scofield, et al., J. Biol. Chem. 262:12202, 1987; Baszczynski, et al., Plant Mol. Biol. 14:633, 1990), Brazil Nut albumin (Pearson et al., Plant Mol. Biol. 18:235-245, 1992), legumin (Ellis, et al. Plant Mol. Biol. 10:203-214, 1988), Glutelin (Takaiwa, et al., Mol. Gen. Genet. 208:15-22, 1986; Takaiwa, et al., FEBS Letts. 221:43-47, 1987), Zein (Matzke et al., Plant Mol Biol, 143).323-32 1990), napA (Stalberg, et al., Planta 199:515-519, 1996), Wheat SPA (Albanietal, Plant Cell, 9:171-184, 1997), sunflower oleosin (Cummins, et al., Plant Mol. Biol. 19:873-876, 1992)], endosperm specific promoters (e.g., wheat LMW and HMW, glutenin-1 (Mol Gen Genet 216: 81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116 (1): 53-62, 1998), Biz2 (EP99106056.7), Synthetic promoter (Vicente-Carbajosa et al., Plant J. 13:629-640, 1998), rice prolamin NRP33, rice-globulin Glb-1 (Wu et al., Plant Cell Physiology 39 (8) 885-889, 1998), rice alpha-globulin REB/OHP-1 (Nakase et al. Plant Mol. Biol. 33:513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters (e.g., rice OSH1; Sato et al., Proc. Nati. Acad. Sci. USA, 93:8117-8122), KNOX (Postma-Haarsma of al, Plant Mol. Biol. 39:257-71, 1999), rice oleosin (Wu et at, J. Biochem., 123:386, 1998)] flower-specific promoters, for example, AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, and promoters specific for plant reproductive tissues (e.g., OsMADS promoters; U.S. Patent Publication 2007/0006344).

Examples of promoters suitable for preferential expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the disclosure is the stem specific promoter described in U.S. Pat. No. 5,625,136, which naturally drives expression of a maize trpA gene.

In addition, promoters functional in plastids can be used. Non-limiting examples of such promoters include the bacteriophage T3 gene 9 5' UTR and other promoters disclosed in U.S. Pat. No. 7,579,516. Other promoters useful with the disclosure include but are not limited to the S-E9 small subunit RuBP carboxylase promoter and the Kunitz trypsin inhibitor gene promoter (Kti3).

In some embodiments, inducible promoters can be used. Thus, for example, chemical-regulated promoters can be used to modulate the expression of a gene in a plant through the application of an exogenous chemical regulator. Regulation of the expression of nucleotide sequences of the disclosure via promoters that are chemically regulated enables the polypeptides of the disclosure to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression. Examples of such technology for chemical induction of gene expression is detailed in published application EP 0 332 104 and U.S. Pat. No. 5,614,395.

Chemical inducible promoters are known in the art and include, but are not limited to, the maize In2-2 promoter, which is activated by benzene sulfonamide herbicide safeners, the maize GST promoter, which is activated by hydrophobic electrophilic compounds that are used as pre-emergent herbicides, the tobacco PR-1 a promoter, which is activated by salicylic acid (e.g., the PR1a system), steroid steroid-responsive promoters (see, e.g., the glucocorticoid-inducible promoter in Schena et al. (1991) Proc. Natl. Acad. Sci. USA 88, 10421-10425 and McNellis et al. (1998) Plant J. 14, 247-257), tetracycline-inducible and tetracycline-repressible promoters (see, e.g., Gatz et al. (1991) Mol. Gen. Genet. 227, 229-237, and U.S. Pat. Nos. 5,814,618 and 5,789,156), Lac repressor system promoters, copper-inducible system promoters, salicylate-inducible system promoters (e.g., the PR1a system), glucocorticoid-inducible promoters (Aoyama et al. (1997) Plant J. 11:605-612), and ecdysone-inducible system promoters.

Other non-limiting examples of inducible promoters include ABA- and turgor-inducible promoters, the auxin-binding protein gene promoter (Schwob et al. (1993) Plant J. 4:423-432), the UDP glucose flavonoid glycosyl-transferase promoter (Ralston et al. (1988) Genetics 119:185-197), the MPI proteinase inhibitor promoter (Cordero et al. (1994) Plant J. 6:141-150), and the glyceraldehyde-3-phosphate dehydrogenase promoter (Kohler et al. (1995) Plant Mol. Biol. 29:1293-1298; Martinez et al. (1989) J. Mol. Biol. 208:551-565; and Quigley et al. (1989) J. Mol. Evol. 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) Current Opinion Biotechnol. 7:168-172 and Gatz (1997) Annu. Rev. Plant Physiol. Plant Mol. Biol. 48:89-108. Other chemically inducible promoters useful for directing the expression of the nucleotide sequences of this disclosure in plants are disclosed in U.S. Pat. No. 5,614,395. Chemical induction of gene expression is also detailed in EP 0 332 104 (to Ciba-Geigy) and U.S. Pat. No. 5,614,395.

Another category of promoters useful in the disclosure are wound inducible promoters. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

In some embodiments, a recombinant vector is provided which comprises a polynucleotide, an assembled polynucleotide, a nucleic acid molecule, or an expression cassette of the disclosure. Certain vectors for use in transformation of plants and other organisms are known in the art. In other embodiments, non-limiting examples of a vector include a plasmid, cosmid, phagemid, artificial chromosome, phage or viral vector. In embodiments, the vector is plant vector, e.g., for use in transformation of plants. In embodiments, the vector is a bacterial vector, e.g., for use in transformation of bacteria. Suitable vectors for plants, bacteria and other organisms are known in the art.

Thus, some embodiments are directed to expression cassettes designed to express the polynucleotides and nucleic acid molecules of the disclosure. In some embodiments, an expression cassette comprises a nucleic acid molecule having at least a control sequence operatively linked to a nucleotide sequence of interest, e.g. a nucleotide sequence encoding an insecticidal protein of the disclosure. In this manner, for example, plant promoters operably linked to the nucleotide sequences to be expressed are provided in expression cassettes for expression in a plant, plant part or plant cell.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the disclosure, an expression cassette of this disclosure also can include other regulatory sequences. Regulatory sequences include, but are not limited to, enhancers, introns, translation leader sequences, termination signals, and polyadenylation signal sequences.

In some embodiments, an expression cassette can also include polynucleotides that encode other desired traits in addition to the disclosed proteins. Such expression cassettes comprising the stacked traits may be used to create plants, plant parts or plant cells having a desired phenotype with the stacked traits (i.e., molecular stacking). Such stacked combinations in plants can also be created by other methods including, but not limited to, cross breeding plants by any conventional methodology. If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this disclosure, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific nuclease or recombination system (e.g., FRT/Flp, Cre/Lox, TALE-endonucleases, zinc finger nucleases, CRISPR/Cas and related technologies). See U.S. Pat. Nos. 7,214,536, 8,921,332, 8,765,448, 5,527,695, 5,744,336, 5,910,415, 6,110,736, 6,175,058, 6,720,475, 6,455,315, 6,458,594 and US Patent Publication Nos. US2019093090, US2019264218, US2018327785, US2017240911, US2016208272, US2019062765.

The expression cassette also can include an additional coding sequence for one or more polypeptides or double stranded RNA molecules (dsRNA) of interest for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956.

Polynucleotides conferring resistance/tolerance to an herbicide that inhibits the growing point or meristem, such as an imidazalinone or a sulfonylurea can also be suitable in some embodiments. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the disclosure. See, e.g., U.S. Pat. Nos. 4,940,835 and 4,769,061, 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and/or coleopteran insect larvae. Examples of such Bt insecticidal proteins include the Cry proteins such as CryIAa, CryIAb, CryIAc, CryIB, CryIC, CryID, CryIEa, CryIFa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) Microbiol. Mol. Biol. Rev. 62:807-813).

In embodiments, an additional polypeptide is an insecticidal polypeptide derived from a non-Bt source, including without limitation, an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin.

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) Foundation for Biotechnical and Industrial Fermentation Research 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) Enzyme Microb. Technol. 14:566; Torronen et al. (1992) Bio/Technology 10:1461; and Xu et al. (1998) Appl. Microbiol. Biotechnol. 49:718).

In other embodiments, a polypeptide useful for the disclosure can be a polysaccharide degrading enzyme. Plants of this disclosure producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like. In one embodiment, the α-amylase is the synthetic α-amylase, Amy797E, described is U.S. Pat. No. 8,093,453, herein incorporated by reference in its entirety.

Further enzymes which may be used with the disclosure include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this disclosure can be cellobiohydrolase (CBH) enzymes (EC 3.2.1.91). In one embodiment, the cellobiohydrolase enzyme can be CBH1 or CBH2.

Other enzymes useful with the disclosure include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Double stranded RNA molecules useful with the disclosure include but are not limited to those that suppress target insect genes. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, hemolymph synthesis, hemolymph maintenance, neurotransmission, cell division, energy metabolism, respiration, and apoptosis.

Transgenic Cells, Plants, Plant Parts, Seed

In some aspects, the disclosure further provides transgenic cells, plants, plant parts, and seed comprising the insecticidal proteins or nucleic acids of the disclosure. In some embodiments, the disclosure provides a non-human host cell comprising a polynucleotide, a nucleic acid molecule, an expression cassette, a vector, or a polypeptide of the disclosure. The transgenic non-human host cell can include, but is not limited to, a plant cell (including a monocot cell and/or a dicot cell), a yeast cell, a bacterial cell or an insect cell. Accordingly, in some embodiments, a bacterial cell is provided which is selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc,* or *Alcaligenes.* Thus, for example, as biological insect control agents, the disclosed insecticidal proteins can be produced by expression of a polynucleotide encoding the same in a bacterial cell. For example, in some embodiments, a *Bacillus thuringiensis* cell comprising a polynucleotide encoding an insecticidal protein of the disclosure is provided.

In some embodiments, the transgenic plant cell is a dicot plant cell or a monocot plant cell. In additional embodiments, the dicot plant cell is a soybean cell, sunflower cell, tomato cell, cole crop cell, cotton cell, sugar beet cell or a tobacco cell. In further embodiments, the monocot cell is a barley cell, maize cell, oat cell, rice cell, sorghum cell, sugar cane cell or wheat cell. In some embodiments, the disclosure provides a plurality of dicot cells or monocot cells comprising a polynucleotide expressing a disclosed insecticidal proteins. In embodiments, the plurality of cells are juxtaposed to form an apoplast and are grown in natural sunlight. In embodiments, the transgenic plant cell cannot regenerate a whole plant.

In other embodiments of the disclosure, an insecticidal protein of the disclosure is expressed in a higher organism, for example, a plant. Such transgenic plants expressing effective amounts of the insecticidal protein to control plant pests such as insect pests. When an insect starts feeding on such a transgenic plant, it ingests the expressed insecticidal protein. This can deter the insect from further biting into the plant tissue or may even harm or kill the insect. In some embodiments, a disclosed polynucleotide is inserted into an expression cassette, which is then stably integrated in the genome of the plant. In other embodiments, the polynucleotide is included in a non-pathogenic self-replicating virus.

In some embodiments of the disclosure, a transgenic plant cell comprising a nucleic acid molecule or polypeptide of the disclosure is a cell of a plant part, a plant organ or a plant culture (each as described herein) including, but not limited to, a root, a leaf, a seed, a flower, a fruit, a pollen cell, organ or plant culture, and the like, or a callus cell or culture.

A transgenic plant or plant cell transformed in accordance with the disclosure may be a monocot or dicot plant or plant cell and includes, but is not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, papaya, mango, banana, and specialty plants, such as *Arabidopsis*, and woody plants such as coniferous and deciduous trees. Preferably, plants of the of the disclosure are crop plants such as maize, sorghum, wheat, sunflower, tomato, crucifers, peppers, potato, cotton, rice, soybean, sugar beet, sugarcane, tobacco, barley, oilseed rape, and the like.

Once a desired polynucleotide has been transformed into a particular plant species, it may be propagated in that species or moved into other varieties of the same species, particularly including commercial varieties, using any appropriate technique including traditional breeding techniques.

The disclosed insecticidal proteins can function in the plant part, plant cell, plant organ, seed, harvested product, processed product or extract, and the like, as an insect control agent. In other words, the insecticidal proteins can continue to perform the insecticidal function it had in the transgenic plant. The nucleic acid can function to express the insecticidal protein. As an alternative to encoding the insecticidal protein of the disclosure, the nucleic acid can function to identify a transgenic plant part, plant cell, plant organ, seed, harvested product, processed product or extract of the disclosure.

In embodiments, a transgenic plant, plant part, plant cell, plant organ, or seed of the disclosure is hemizygous for a polynucleotide or expression cassette of the disclosure. In embodiments, a transgenic plant, plant part, plant cell, plant organ, or seed of the disclosure is homozygous for a polynucleotide or expression cassette of the disclosure.

Additional embodiments of the disclosure include harvested products produced from the transgenic plants or parts thereof of the disclosure, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the disclosure, wherein said seed or other plant part comprises a nucleic acid molecule/polynucleotide/nucleotide sequence of this disclosure.

In other embodiments, the disclosure provides an extract from a transgenic seed or a transgenic plant of the disclosure, wherein the extract comprises a nucleic acid molecule, a polynucleotide, a nucleotide sequence or an insecticidal protein of the disclosure. Extracts from plants or plant parts can be made according to procedures well known in the art (See, de la Torre et al., Food, Agric. Environ. 2 (1): 84-89 (2004); Guidet, Nucleic Acids Res. 22 (9): 1772-1773 (1994); Lipton et al., Food Agric. Immun. 12:153-164 (2000)). Such extracts may be used, e.g., in methods to detect the presence of an insecticidal protein or a polynucleotide of the disclosure.

In embodiments, a transgenic plant, plant part, plant cell, plant organ, seed, harvested product, processed product or extract has increased insecticidal activity to one or more insect pests (e.g., a coleopteran pest, such as Western corn rootworm) as compared with a suitable control that does not comprise a nucleic acid encoding an insecticidal protein of the disclosure.

Plant Transformation

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are generally suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (e.g., Phosphomannose Isomerase), provide resistance to an antibiotic (e.g., kanamycin, hygromycin or methotrexate) or a herbicide (e.g., glyphosate or glufosinate). However, the choice of selectable marker is not critical to the disclosure.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) Nucleic Acids Res. 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199:612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14 (6): 745-50, 1996) or Frame et al. (Plant Physiol 129 (1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an Agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Soybean plant material can be suitably transformed, and fertile plants regenerated by many methods which are well known to one of skill in the art. For example, fertile morphologically normal transgenic soybean plants may be obtained by: 1) production of somatic embryogenic tissue from, e.g., immature cotyledon, hypocotyl or other suitable tissue; 2) transformation by particle bombardment or infection with *Agrobacterium*; and 3) regeneration of plants. In one example, as described in U.S. Pat. No. 5,024,944, cotyledon tissue is excised from immature embryos of soybean, preferably with the embryonic axis removed, and cultured on hormone-containing medium to form somatic embryogenic plant material.

This material is transformed using, for example, direct DNA methods, DNA coated microprojectile bombardment or infection with *Agrobacterium*, cultured on a suitable selection medium and regenerated, optionally also in the continued presence of selecting agent, into fertile transgenic soybean plants. Selection agents may be antibiotics such as kanamycin, hygromycin, or herbicides such as phosphinothricin or glyphosate or, alternatively, selection may be based upon expression of a visualizable marker gene such as GUS. Alternatively, target tissues for transformation comprise meristematic rather than somaclonal embryogenic tissue or, optionally, is flower or flower-forming tissue. Other examples of soybean transformations can be found, e.g. by physical DNA delivery method, such as particle bombardment (Finer and McMullen (1991) In Vitro Cell Dev. Biol. 27P: 175-182; McCabe et al. (1988) Bio/technology 6:923-926), whisker (Khalafalla et al. (2006) African J. of Biotechnology 5:1594-1599), aerosol bean injection (U.S. Pat. No. 7,001,754), or by *Agrobacterium*-mediated delivery methods (Hinchee et al. (1988) Bio/Technology 6:915-922; U.S. Pat. No. 7,002,058; U.S. Patent Application Publication No. 20040034889; U.S. Patent Application Publication No. 20080229447; Paz et al. (2006) Plant Cell Report 25:206-213).

Soybean transgenic plants can be generated with the heretofore described binary vectors containing selectable marker genes with different transformation methods. For example, a vector is used to transform immature seed targets as described (see e.g., U.S. Patent Application Publication No. 20080229447) to generate transgenic HPPD soybean plants directly using HPPD inhibitor, such as mesotrione, as selection agent. Optionally, other herbicide tolerance genes can be present in the polynucleotide alongside other sequences which provide additional means of selection/identification of transformed tissue including, for example, the known genes which provide resistance to kanamycin, hygromycin, phosphinothricin, butafenacil, or glyphosate. For example, different binary vectors containing PAT or EPSPS selectable marker genes are transformed into immature soybean seed target to generate pesticidal and herbicide tolerant plants using *Agrobacterium*-mediated transformation and glufosinate or glyphosate selection as described (see e.g., U.S. Patent Application Publication No. 20080229447).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792.

Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the disclosure can be directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305.

Methods of selecting for transformed, transgenic plants, plant cells or plant tissue culture are routine in the art and can be employed in the methods of the disclosure provided herein. For example, a recombinant vector of the disclosure also can include an expression cassette comprising a nucleotide sequence for a selectable marker, which can be used to select a transformed plant, plant part or plant cell.

Examples of selectable markers include, but are not limited to, a nucleotide sequence encoding neo or nptII, which confers resistance to kanamycin, G418, and the like (Potrykus et al. (1985) Mol. Gen. Genet. 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella* ozaenae that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this disclosure.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: Chromosome Structure and Function: Impact of New Concepts, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) Proc. Natl. Acad. Sci. USA 75:3737-3741); a nucleotide sequence encoding xylE that encodes a catechol dioxygenase (Zukowsky et al. (1983) Proc. Natl. Acad. Sci. USA 80:1101-1105); a nucleotide sequence encoding tyrosinase, an enzyme capable of oxidizing tyrosine to DOPA and dopaquinone, which in turn condenses to form melanin (Katz et al. (1983) J. Gen. Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding aequorin which may be employed in calcium-sensitive bioluminescence detection (Prasher et al. (1985) Biochem. Biophys. Res. Comm. 126:1259-1268); or a nucleotide sequence encoding green fluorescent protein (Niedz et al. (1995) Plant Cell Reports 14:403-406) or other fluorescent protein such as dsRed or mCherry. One of skill in the art is capable of choosing a suitable selectable marker for use in an expression cassette of this disclosure.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)).

Additionally, the genetic properties engineered into the transgenic seeds and plants, plant parts, or plant cells of the disclosure described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotide is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Once a desired polynucleotide has been transformed into a particular plant species, it may be propagated in that species or moved into other varieties of the same species, particularly including commercial varieties, using traditional breeding techniques.

Insecticidal Compositions

In some embodiments, an insecticidal composition is provided comprising an insecticidal protein of the disclosure in an agriculturally acceptable carrier. As used herein an "agriculturally-acceptable carrier" can include natural or synthetic, organic or inorganic material which is combined with the active protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing an insecticidal protein of the disclosure in planta is an agriculturally-acceptable carrier of the expressed insecticidal protein, the combination of plant and the protein is an insecticidal composition.

In further embodiments, the insecticidal composition comprises a bacterial cell or a transgenic bacterial cell of the disclosure, wherein the bacterial cell or transgenic bacterial cell produces an insecticidal protein of the disclosure. Such an insecticidal composition can be prepared by desiccation, lyophilization, homogenization, extraction, filtration, centrifugation, sedimentation, or concentration of a culture of *Bacillus thuringiensis* (Bt), including a transgenic Bt culture. In embodiments, a composition of the disclosure may comprise at least about 1%, at least about 5%, at least about 10%, at least about 20%, at least about 25%, at least about 30%, at least about 35%, at least about 40%, at least about 50%, at least about 60%, at least about 70%, at least about 80%, at least about 90%, at least about 95%, at least about 97%, or at least 99% by weight a polypeptide of the disclosure. In additional embodiments, the composition comprises from about 1% to about 99% by weight of the insecticidal protein of the disclosure.

Disclosed insecticidal proteins can be used in combination with other pest control agents to increase pest target spectrum and/or for the prevention or management of insect resistance. Furthermore, the use of the disclosed insecticidal proteins in combination with an insecticidal agent which has a different mode of action or target a different receptor in the insect gut has particular utility for the prevention and/or management of insect resistance.

Therefore, in some embodiments, a composition is provided that controls one or more plant pests (e.g., an insect pest such as a lepidopteran insect pest, a coleopteran insect pest, a hemipteran insect pest and/or a dipteran insect pest), wherein the composition comprises a first pest control agent, which is a disclosed insecticidal protein and at least a second pest control agent that is different from the first pest control agent. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first pest control agent, which is a disclosed insecticidal protein when the transgenic plant comprises the second pest control agent. In other embodiments, the formulation comprises the second pest control agent when the transgenic plant comprises the first pest control agent, which is an engineered insecticidal protein of the disclosure.

In some embodiments, the second pest control agent can be one or more of a chemical pesticide, such as an insecticide, a *Bacillus thuringiensis* (Bt) insecticidal protein, and/or a non-Bt pesticidal agent including without limitation a Xenorhabdus insecticidal protein, a *Photorhabdus* insecticidal protein, a *Brevibacillus laterosporus* insecticidal protein, a *Bacillus sphaericus* insecticidal protein, a protease inhibitor (both serine and cysteine types), a lectin, an alpha-amylase, a peroxidase, a cholesterol oxidase, or a double stranded RNA (dsRNA) molecule.

In other embodiments, the second pest control agent is one or more chemical pesticides, which is optionally a seed coating. Non-limiting examples of chemical pesticides include pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is one or more of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultapsodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from one or more of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from: Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8 Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9 Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30 Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa, Cry73Aa, or any combination of the foregoing. In some embodiments, the second pest control agent comprises the CrylAb protein in the Bt11 event (see U.S. Pat. No. 6,114,608), the Cry3A055 protein in the MIR604 event (see U.S. Pat. No. 8,884,102), the eCry3.1Ab protein in the 5307 event (see U.S. Pat. No. 10,428,393) and/or the mCry3A protein in the MZI098 event (see US Patent Application No. US20200190533). In some embodiments, the second pest control agent comprises the Bt11 event (see U.S. Pat. No. 6,114,608), the MIR604 event (see U.S. Pat. No. 8,884,102), the 5307 event (see U.S. Pat. No. 10,428,393) and/or the MZI098 event (see US Patent Application No. US20200190533).

In further embodiments, the second pest control agent is one or more Vip3 vegetative insecticidal proteins. Some structural features that identify a protein as being in the Vip3 class of proteins includes: 1) a size of about 80-88 kDa that is proteolytically processed by insects or trypsin to about a 62-66 kDa toxic core (Lee et al. 2003. Appl. Environ. Microbiol. 69:4648-4657); and 2) a highly conserved N-terminal secretion signal which is not naturally processed during secretion in B. thuringiensis. Non-limiting examples of members of the Vip3 class and their respective GenBank accession numbers, U.S. Patent or patent publication number are Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat.

No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (U.S. Patent Application Publication 20040128716), Vip3Ad1 (U.S. Patent Application Publication 20040128716), Vip3Ad2 (CAI43276), Vip3Ae1 (CAI43277), Vip3Af1 (U.S. Pat. No. 7,378,493), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), Vip3Ah1 (DQ832323), Vip3Ba1 (AAV70653), Vip3Ba2 (HM117635), Vip3Bb1 (U.S. Pat. No. 7,378,493), Vip3Bb2 (AB030520) and Vip3Bb3 (ADI48120). In embodiments, the Vip3 protein is Vip3Aa (U.S. Pat. No. 6,137,033), for example, as represented by corn event MIR162 (U.S. Pat. Nos. 8,232,456; 8,455,720; and 8,618,272). In some embodiments, the second pest control agent comprises the event MIR162 (U.S. Pat. Nos. 8,232,456; 8,455,720; and 8,618,272).

In embodiments, the second pest control agent may be derived from sources other than B. thuringiensis. For example, the second pest control agent can be an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a Bacillus cereus insecticidal protein, a Xenorhabdus spp. (such as X. nematophila or X. bovienii) insecticidal protein, a Photorhabdus spp. (such as P. luminescens or P. asymobiotica) insecticidal protein, a Brevibacillus spp. (such as B. laterosporous) insecticidal protein, a Lysinibacillus spp. (such as L. sphearicus) insecticidal protein, a Chromobacterium spp. (such as C. subtsugae or C. piscinae) insecticidal protein, a Yersinia spp. (such as Y. entomophaga) insecticidal protein, a Paenibacillus spp. (such as P. propylaea) insecticidal protein, a Clostridium spp. (such as C. bifermentans) insecticidal protein, a Pseudomonas spp. (such as P. fluorescens) and a lignin. In other embodiments, the second agent may be at least one insecticidal protein derived from an insecticidal toxin complex (Tc) from Photorhabdus, Xenorhabus, Serratia, or Yersinia. In other embodiments, the insecticidal protein may be an ADP-ribosyltransferase derived from an insecticidal bacteria, such as Photorhabdus ssp. In other embodiments, the insecticidal protein may be a VIP protein, such as VIP1 and/or VIP2 from B. cereus. In still other embodiments, the insecticidal protein may be a binary toxin derived from an insecticidal bacteria, such as ISP1A and ISP2A from B. laterosporous or BinA and BinB from L. sphaericus. In still other embodiments, the insecticidal protein may be engineered or may be a hybrid or chimera of any of the preceding insecticidal proteins.

Other example second pest controls agents include DIG-657 (US Patent Publication 2015366211); PtIP-96 (US Patent Publication 2017233440); PIP-72 (US Patent Publication US2016366891); PIP-83 (US Patent Publication 2016347799); PIP-50 (US Patent Publication 2017166921);

IPD73 (US Patent Publication 2019119334); IPD090 (US Patent Publication 2019136258); IPD80 (US Patent Publication 2019256563); IPD078, IPD084, IPD086, IPD087, IPD089 (US Patent Publication 2020055906); IPD093 (International Application Publication WO2018111551); IPD059 (International Application Publication WO2018232072); IPD113 (International Application Publication WO2019178042); IPD121 (International Application Publication WO2018208882); IPD110 (International Application Publication WO2019178038); IPD103 (International Application Publication WO2019125717); IPD092; IPD095; IPD097; IPD099; IPD100, IPD105; IPD106; IPD107; IPD111; IPD112 (International Application Publication WO2020055885); IPD102 (International Application Publication WO2020076958) CrylB.868 and CrylDa_7 (US Patent Publication 2020-032289); TIC107 (U.S. Pat. No. 8,049,071); Cry2Ab and CrylA.105 (U.S. Pat. No. 10,584, 391); CrylF, Cry34Ab1, Cry35Ab1 (U.S. Pat. No. 10,407, 688); TIC6757, TIC7472, TIC7473, TIC6757 (US Patent Publication 2017058294); TIC3668, TIC3669, TIC3670, TIC4076, TIC4078, TIC4260, TIC4346, TIC4826, TIC4861, TIC4862, TIC4863. TIC-3668 (US Patent Publication 2016319302); TIC7040, TIC7042, TIC7381, TIC7382, TIC7383, TIC7386, TIC7388, TIC7389 (US Patent Publication 2018291395); TIC7941 (US Patent Publication 2020229445) TIC836, TIC860, TIC867, TIC868, TIC869, and TIC1100 (International Application Publication WO2016061391), TIC2160 (International Application Publication WO2016061392), ET66, TIC400, TIC800, TIC834, TIC1415, AXMI-001, AXMI-002, AXMI-030, AXMI-035, AND AXMI-045 (US Patent Publication 20130117884), AXMI-52, AXMI-58, AXMI-88, AXMI-97, AXMI-102, AXMI-112, AXMI-117, AXMI-100 (US Patent Publication 201-0310543), AXMI-115, AXMI-113, AXMI-005 (US Patent Publication 20130104259), AXMI-134 (US Patent Publication 20130167264), AXMI-150 (US Patent Publication 20100160231), AXMI-184 (US Patent Publication 20100004176), AXMI-196, AXMI-204, AXMI-207, AXMI-209 (US Patent Publication 2011-0030096), AXMI-218, AXMI-220 (US Patent Publication 20140245491), AXMI-221z, AXMI-222z, AXMI-223z, AXMI-224z, AXMI-225z (US Patent Publication 20140196175), AXMI-238 (US Patent Publication 20140033363), AXMI-270 (US Patent Publication 20140223598), AXMI-345 (US Patent Publication 20140373195), AXMI-335 (International Application Publication WO2013134523), DIG-3 (US Patent Publication 20130219570), DIG-5 (US Patent Publication 20100317569), DIG-11 (US Patent Publication 20100319093), AflP-1A (US Patent Publication 20140033361), AflP-1B (US Patent Publication 20140033361), PIP-1APIP-1B (US Patent Publication 20140007292), PSEEN3174 (US Patent Publication 20140007292), AECFG-592740 (US Patent Publication 20140007292), Pput_1063 (US Patent Publication 20140007292), DIG-657 (International Application Publication WO2015195594), Pput_1064 (US Patent Publication 20140007292), GS-135 (US Patent Publication 20120233726), GS153 (US Patent Publication 20120192310), GS154 (US Patent Publication 20120192310), GS155 (US Patent Publication 20120192310), DIG-911 and DIG-180 (US Patent Publication No. 20150264940); and the like.

In some embodiments, the second pesticidal agent can be non-proteinaceous, for example, an interfering RNA molecule such as a dsRNA, which can be expressed transgenically or applied as part of a composition (e.g., using topical methods). An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the disclosed engineered proteins or may target a different pest. The targeted insect plant pest may feed by chewing, sucking, or piercing. Interfering RNAs are known in the art to be useful for insect control. In embodiments, the dsRNA useful for insect control is described in US Patent Publications 20190185526, 2018020028 or 20190177736. In embodiments, the dsRNA useful for insect control is described in U.S. Pat. Nos. 9,238,8223, 9,340,797, or 8,946, 510. In embodiments, the dsRNA useful for insect control is described in U.S. Patent Publications 20200172922, 20110054007, 20140275208, 20160230185, or 20160230186. In other embodiments, the interfering RNA may confer resistance against a non-insect plant pest, such as a nematode pest or a virus pest.

In still further embodiments, the first insect control agent, which is a disclosed insecticidal protein and the second pest control agent are co-expressed in a transgenic plant. This co-expression of more than one pesticidal principle in the same transgenic plant can be achieved by genetically engineering a plant to contain and express the nucleic acid sequences encoding the insect control agents. For example, the co-expression of more than one pesticidal agent in the same transgenic plant can be achieved by making a single recombinant vector comprising coding sequences of more than one pesticidal agent in a "molecular stack" and genetically engineering a plant to contain and express all the pesticidal agents in the transgenic plant. Such molecular stacks may be also be made by using mini-chromosomes as described, for example in U.S. Pat. No. 7,235,716. Alternatively, a plant, Parent 1, can be genetically engineered for the expression of the disclosed insecticidal proteins. A second plant, Parent 2, can be genetically engineered for the expression of a second pest control agent. By crossing Parent 1 with Parent 2, progeny plants are obtained which express both insect control agents from Parents 1 and 2.

In other embodiments, the disclosure provides a stacked transgenic plant resistant to plant pest infestation comprising a nucleic acid (e.g., DNA) sequence encoding a dsRNA for suppression of an essential gene in a target pest and a nucleic acid e.g., (DNA) sequence encoding a disclosed insecticidal protein exhibiting insecticidal activity against the target pest.

Transgenic plants or seed comprising and/or expressing a disclosed protein can also be treated with an insecticide or insecticidal seed coating as described in U.S. Pat. Nos. 5,849,320 and 5,876,739. In embodiments, where both the insecticide or insecticidal seed coating and the transgenic plant or seed of the disclosure are active against the same target insect, for example a coleopteran pest (e.g., Western corn rootworm), the combination is useful (i) in a method for further enhancing activity of the composition of the disclosure against the target insect, and/or (ii) in a method for preventing development of resistance to the composition of the disclosure by providing yet another mechanism of action against the target insect. Thus, in embodiments, a method is provided of enhancing control of a coleopteran insect population comprising providing a transgenic plant or seed of the disclosure and applying to the plant or the seed an insecticide or insecticidal seed coating to a transgenic plant or seed of the disclosure.

Even where the insecticide or insecticidal seed coating is active against a different insect, the insecticide or insecticidal seed coating is useful to expand the range of insect control, for example by adding an insecticide or insecticidal seed coating that has activity against coleopteran insects to a transgenic seed of the disclosure, which, in some embodiments, has activity against lepidopteran insects, the coated transgenic seed produced controls both lepidopteran and coleopteran insect pests.

Methods of Making and Using the Insecticidal Proteins, Nucleic Acids, and Transgenic Plants In addition to providing compositions, the disclosure also provides methods of producing and using an engineered insecticidal protein of the disclosure. In some embodiments, the method of producing comprises culturing a transgenic non-human host cell that comprises a polynucleotide, expression cassette or vector that expresses a described insecticidal protein under conditions in which the host cell produces the insecticidal protein that is toxic to the coleopteran pest. In some embodiments, the transgenic non-human host cell is a plant cell. In some other embodiments, the plant cell is a maize cell. In other embodiments, the conditions under which the plant cell are grown include natural sunlight. In other embodiments, the transgenic non-human host cell is a bacterial cell. In still other embodiments, the transgenic non-human host cell is a yeast cell.

In some embodiments, the methods of the disclosure provide control of at least one coleopteran pest, including without limitation, one or more of the following: *Diabrotica barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata and D. viridula*; and any combination thereof. Other nonlimiting examples of Coleopteran insect pests include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp.

such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing. In embodiments, the engineered insecticidal protein has insecticidal activity against a Western corn rootworm colony that is resistant to an engineered Cry3 protein (e.g. a eCry3.1Ab, including without limitation maize event 5307).

Also encompassed are methods of producing an insect-resistant (e.g., a coleopteran insect-resistant) transgenic plant. In representative embodiments, the method comprises: introducing into a plant a polynucleotide, expression cassette or vector comprising a nucleotide sequence that encodes a disclosed insecticidal protein (including toxin fragments and modified forms that are substantially identical to the polypeptides specifically disclosed herein), wherein the nucleotide sequence is expressed in the plant to produce the disclosed insecticidal protein, thereby conferring to the plant resistance to the insect pest, and producing an insect-resistant transgenic plant (e.g., as compared with a suitable control plant, such as a plant that does not comprise the disclosed polynucleotide, expression cassette or vector and/or or does not express a disclosed insecticidal polypeptide).

In some embodiments, a pest-resistant transgenic plant is resistant to an insect pest selected from the group consisting of *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm).

In embodiments, the method of introducing the disclosed polynucleotide, expression cassette or vector into the plant comprises first transforming a plant cell with the polynucleotide, expression cassette or vector and regenerating a transgenic plant therefrom, where the transgenic plant comprises the polynucleotide, expression cassette or vector and expresses the disclosed chimeric insecticidal protein of the disclosure.

Alternatively, or additionally, the introducing step can comprise crossing a first plant comprising the polynucleotide, expression cassette or vector with a second plant (e.g., a different plant from the first plant, for example, a plant that does not comprise the polynucleotide, expression cassette or vector) and, optionally, producing a progeny plant that comprises the polynucleotide, expression cassette or vector and expresses a disclosed insecticidal protein, thereby resulting in increased resistance to at least one insect pest. Thus, a transgenic plant encompasses a plant that is the direct result of a transformation event and the progeny thereof (of any generation) that comprise the polynucleotide, expression cassette or vector and optionally expresses the insecticidal protein resulting in increased resistance to at least one insect pest. Once a desired nucleic acid molecule has been transformed into a particular plant species, it may be propagated in that species or moved into other varieties of the same species, particularly including commercial varieties, using traditional breeding techniques.

The disclosure further provides a method of identifying a transgenic plant of the disclosure, the method comprising detecting the presence of a polynucleotide, expression cassette, vector or insecticidal protein of the disclosure in a plant (or a plant cell, plant part, and the like derived therefrom), and thereby identifying the plant as a transgenic plant of the disclosure based on the presence of the polynucleotide, expression cassette, vector or insecticidal protein of the disclosure.

Embodiments further provide a method of producing a transgenic plant with increased resistance to at least one insect pest (e.g., a least one lepidopteran pest), the method comprising: planting a seed comprising a polynucleotide, expression cassette or vector of the disclosure, and growing a transgenic plant from the seed, where the transgenic plant comprises the polynucleotide, expression cassette or vector and produces the insecticidal protein.

In embodiments, transgenic plants produced by the methods of the disclosure comprise a polynucleotide, expression cassette or vector of the disclosure. In embodiments, a transgenic plant produced by the methods of the disclosure comprise an insecticidal protein of the disclosure and, optionally have increased resistance to at least one insect pest.

The methods of producing a transgenic plant described herein optionally comprise a further step of harvesting a seed from the transgenic plant, where the seed comprises the polynucleotide, expression cassette or vector and produces the insecticidal protein. Optionally, the seed produces a further transgenic plant that comprises the polynucleotide, expression cassette or vector and produces the insecticidal protein, and thereby has increased resistance to at least one insect pest.

The disclosure further provides plant parts, plant cells, plant organs, plant cultures, seed, plant extracts, harvested products and processed products of the transgenic plants produced by the methods of the disclosure.

As a further aspect, the disclosure also provides a method of producing seed, the method comprising: providing a transgenic plant that comprises a disclosed polynucleotide, expression cassette or vector, and harvesting a seed from the transgenic plant, wherein the seed comprises the polynucleotide, expression cassette, vector and produces the insecticidal protein. Optionally, the seed produces a further transgenic plant that comprises the polynucleotide, expression cassette or vector and produces the insecticidal protein, and thereby has increased resistance to at least one insect pest. In representative embodiments, the step of providing the transgenic plant comprises planting a seed that produces the transgenic plant.

Further provided is a method of producing a hybrid plant seed, the method comprising: crossing a first inbred plant, which is a transgenic plant comprising a polynucleotide, expression cassette or vector of the disclosure, and optionally expressing an insecticidal protein of the disclosure with a different inbred plant (e.g., an inbred plant that does not comprise a polynucleotide, expression cassette or vector of the disclosure) and allowing hybrid seed to form. Optionally, the method further comprises harvesting a hybrid seed. In embodiments, the hybrid seed comprises the polynucleotide, expression cassette or vector of the disclosure, and in embodiments may further comprise an insecticidal protein of the disclosure and have increased resistance to an insect pest. In embodiments, the hybrid seed produces a transgenic plant that comprises the polynucleotide, expression cassette or vector of the disclosure, expresses the insecticidal protein of the disclosure, and has increased resistance to at least one insect pest.

In further embodiments, a method of controlling a coleopteran pest is provided, the method comprising delivering to the insects an effective amount of a disclosed insecticidal protein. To be effective, the insecticidal protein is first orally ingested by the insect. However, the insecticidal protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the disclosed insecticidal proteins of the disclosure. In some particular embodiments, the disclosed insecticidal protein is delivered orally to an insect, wherein the insect ingests one or more parts of a transgenic plant.

In other embodiments, the disclosed insecticidal protein is delivered orally to an insect, wherein the insect ingests one or more parts of a plant covered or partially covered with a composition comprising the insecticidal proteins. Delivering the compositions of the disclosure to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

In some embodiments, the disclosed nucleotide and polypeptide sequences can be used in a bioinformatic analysis to identify additional insecticidal toxins, both the nucleotide sequences and the proteins encoded by the nucleic acids. In embodiments, this identification of additional toxins can be based on percent identity (e.g., using a BLAST or similar algorithm). In other embodiments, the identification of additional toxins could be accomplished using conserved protein domains or epitopes (e.g., Hmmer, psi-BLAST, or hhsuite). In some embodiments, the bioinformatic assay comprises running a sequence identity comparison and selecting one or more candidate insecticidal toxins that has a sequence identity above a certain threshold (e.g., at least 30%, at least 40%, at least 50%, at least 60%, at least 70%, at least 80%, at least 90%, or more identical) relative to a disclosed nucleotide or polypeptide sequence of the disclosure. In some embodiments, the bioinformatic assay comprises running a domain or epitope conservation analysis and selecting one or more candidate insecticidal toxins that has at least one conserved domain or epitope relative to a disclosed nucleotide or polypeptide sequence of the disclosure.

In embodiments, determination of insecticidal activity of disclosed insecticidal proteins can be accomplished through an insect bioassay. Insect bioassay methods are well known in the art and can be "in vitro" or "in planta". In in vitro bioassays, the disclosed proteins are delivered to the desired insect species following production in recombinant bacterial strains (e.g., *E. coli*, *Bacillus thurinigiensis* Cry-). Clarified lysates containing the disclosed engineered proteins produced in these recombinant bacterial strains can be fed orally to the insects. Alternatively, purified engineered proteins can be prepared and fed orally to the insects. In some embodiments, the clarified lysate or purified protein is overlaid on artificial diet prior to infestation with the insects. In other embodiments, the clarified lysate or purified protein is mixed into or incorporated into the artificial diet prior infestation with insects. In in planta bioassays, transgenic plants expressing the disclosed proteins are utilized to deliver the toxin to the desired insect species. In embodiments, sampled tissue is fed orally to the insects. Nonlimiting examples of sampled tissue include leaf, root, pollen, silk, and stem. In some embodiments the plant tissue is mixed into or incorporated into artificial diet prior to infestation with the insects. In embodiments, the evaluated Sons Inc., (1988), Reiter, et al., Methods in *Arabidopsis* Research, World Scientific Press (1992), and Schultz et al., Plant Molecular Biology Manual, Kluwer Academic Publishers (1998).

Example 1: Identification of Proteins with Insecticidal Activity Against Western Corn Rootworm An insecticidal protein, ITD-46, assembled from sequence of an unknown organism was identified from a protein database based on homology to known insecticidal proteins. Other related insecticidal proteins were identified from *Pseudomonas* sp. (OF001), *Methanosarcinaceae archaeon*, *Burkholderia* sp. (ABCPW14), *Acidobacteria bacterium*, *Methanosarcina* sp. (MTP4), and *Streptomyces hainanensis*. The identified proteins are orthologues and share percent identity with each other, ranging from about 15-75% identity (Table 1, percent identity calculated using EMBOSS Needle). *E. coli*-optimized versions of the genes were synthesized, and the genes cloned into a pET29a vector. The resulting constructs were transformed into *E. coli* BL21* (DE3) and protein expression carried out in Luria-Bertani broth with IPTG inductions at 18° C. overnight. The soluble fraction of lysates was prepared from these cultures by use of a French pressure cell followed by centrifugation of whole lysates at 20,000×g for thirty minutes. The supernatant (soluble fraction) was then tested for bioactivity to Western Corn Rootworm (WCR; *Diabrotica virgifera*).

TABLE 1

| | | Percent Identity of Identified Bacterial Orthologues (Polypeptide) | | | | | |
|---|---|---|---|---|---|---|---|
| | 1. ITD-46 | 2. *Pseudomonas* sp. OF001 | 3. *M. archaeon* | 4. *Burkholderia* sp. ABCPW14 | 5. Acidobacteria bacterium | 6. *Methanosarcina* sp. MTP4 | 7. *Streptomyces hainanensis* |
| 1 | X | 49.9 | 74.2 | 29.8 | 48.4 | 75.1 | 15.4 |
| 2 | X | X | 49.1 | 26.4 | 45.5 | 48.1 | 16.7 |
| 3 | X | X | X | 29.6 | 47.5 | 94.0 | 15.4 |
| 4 | X | X | X | X | 26.2 | 29.9 | 15.8 |
| 5 | X | X | X | X | X | 48.1 | 16.9 |
| 6 | X | X | X | X | X | X | 14.6 |
| 7 | X | X | X | X | X | X | X | insects are L1 instars or neonates. In other embodiments, the evaluated insects are of later larval stages, namely L2, L3, L4, or L5 instars.

EXAMPLES

Embodiments of the invention can be better understood by reference to the following detailed examples. The foregoing and following description of embodiments of the invention and the various embodiments are not intended to limit the claims but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims. Art recognized recombinant DNA and molecular cloning techniques may be found in, for example, J. Sambrook, et al., Molecular Cloning: A Laboratory Manual, 4th Ed., Cold Spring Harbor, NY: Cold Spring Harbor Laboratory Press (2012); by T. J. Silhavy, M. L. Berman, and L. W. Enquist, Experiments with Gene Fusions, Cold Spring Harbor Laboratory, Cold Spring Harbor, NY (1984) and by Ausubel, F. M. et al., Current Protocols in Molecular Biology, New York, John Wiley and Bioactivity assays were performed using a diet-incorporation method. Briefly, *E. coli* BL21* (DE3) lysates were mixed with an equal volume of heated artificial insect diet (Bioserv, Inc., Frenchtown, NJ) in 1.5 mL centrifuge tubes and then applied to small petri-dishes. After the diet-sample mixture cooled and solidified, 12 WCR larvae were added to each plate. The plates were sealed and maintained at ambient laboratory conditions with regard to temperature, lighting, and relative humidity. Lysates from *E. coli* BL21* (DE3) cultures harboring the empty pET29a vector were used as negative controls. Mortality was assessed on day 4 and day 6. For this and all subsequent tables, a "−" means no mortality, a "+" means 1-24% mortality, a "++" means 25-49% mortality, a "+++" means 50-74% mortality, and a "++++" means 75-100% mortality. For this and all subsequent tables showing insecticidal activity on CRW, the abbreviations for the "Remarks" column are as follows: s=small larvae, sm=small/medium larvae, m=medium larvae, mb=medium/big larvae, b=big larvae, vb=very big larvae. For this and all subsequent tables showing the insecticidal activity of identified proteins or variants thereof, the "SEQ ID NO." refers to the amino acid sequence of the protein. As shown in Table 2, lysate from the culture expressing the identified protein from ITD-46, displayed strong bioactivity against WCR. As shown in Table 3, varying the pH of the culture (A=acidic) and (B=basic) did not have an appreciable impact on the bioactivity of ITD-46. The pH 7.0 control was 50 mM potassium phosphate, pH 7.0 and 50 mM sodium chloride. ITD-46 was also tested against a number of other Lepidopterans including Brazilian fall armyworm, black cutworm, corn earworm, and soybean looper. There was little to no insecticidal effect on these other pests, indicating the insecticidal impact on CRW was specific, a desirable effect.

As shown in Tables 4, 5, 6 and 7, lysates from the culture expressing the identified protein from *Pseudomonas* sp. (OF001), *Acidobacteria bacterium, Methanosarcinaceae archaeon, Burkholderia* sp. (ABCPW14), and *Streptomyces hainanensis* likewise displayed bioactivity against WCR. Confirmation bioassays using additional lysates expressing these proteins were performed and yielded similar results.

TABLE 2

Insecticidal activity of ITD-46 against Western Corn Rootworm (WCR)

| Treatment | SEQ ID NO. | Day 4 | | | Day 6 | | |
|---|---|---|---|---|---|---|---|
| | | n | Mortality | Remarks | n | Mortality | Remarks |
| BL21*/pET29a-empty | | 12 | + | b | 12 | + | b |
| BL21*/ITD-46 | 1 | 12 | ++++ | m/mb | 12 | ++++ | |

TABLE 3

Insecticidal activity of ITD-46 with varied pH against WCR

| Treatment | SEQ ID NO. | Day 4 | | | Day 6 | | |
|---|---|---|---|---|---|---|---|
| | | n | Mortality | Remarks | n | Mortality | Remarks |
| BL21*/pET29a-emp | | 12 | – | b | 12 | + | b |
| pH 7 control | | 12 | – | b | 12 | + | b |
| BL21*/ITD-46 pH (A) | 1 | 12 | ++++ | | 12 | ++++ | |
| BL21*/ITD-46 pH (B) | 1 | 12 | ++++ | sm | 12 | ++++ | |

TABLE 4

Insecticidal activity of ITD-46 at various lysate dilutions against WCR

| Treatment | SEQ ID NO. | Day 4 | | | Day 6 | | |
|---|---|---|---|---|---|---|---|
| | | n | Mortality | Remarks | n | Mortality | Remarks |
| BL21*/pET29a-emp 1:4 | | 12 | – | b | 12 | – | b |
| BL21*/ITD-46 1:4 | 1 | 12 | ++++ | m | 12 | ++++ | 1b |
| BL21*/ITD-46 1:8 | 1 | 12 | ++++ | mb/m | 12 | ++++ | 1m |
| BL21*/ITD-46 1:16 | 1 | 12 | +++ | mb/m | 12 | ++++ | b |
| BL21*/ITD-46 1:32 | 1 | 12 | ++ | mb/b | 12 | ++++ | b |
| BL21*/ITD-46 1:64 | 1 | 12 | + | b | 12 | ++++ | b |

TABLE 5

Insecticidal activity of ITD-46 and various orthologues against WCR

| Treatment | SEQ ID NO. | Day 4 | | | Day 6 | | |
|---|---|---|---|---|---|---|---|
| | | n | Mortality | Remarks | n | Mortality | Remarks |
| BL21*/pET29a-emp | | 12 | – | b | 12 | – | b |
| BL/21*/ITD-46 | 1 | 12 | ++++ | m | 12 | ++++ | |
| BL21*/Acidobacteria | 5 | 12 | + | mb/m | 12 | ++ | mb/b |
| BL21*/ABCPW14 | 4 | 12 | + | b | 12 | +++ | 2m, 2mb, 2b |
| BL21*/OF001 | 2 | 12 | +++ | m/mb | 12 | ++++ | 1m |

TABLE 5-continued

| | SEQ ID NO. | Day 4 | | | Day 6 | | |
|---|---|---|---|---|---|---|---|
| Treatment | | n | Mortality | Remarks | n | Mortality | Remarks |
| BL21*/MTP4 | 6 | 12 | – | b | 12 | – | b |
| BL21*/*M. archaeon* | 3 | 12 | ++ | b | 12 | ++++ | Mb/b |

_Insecticidal activity of ITD-46 and various orthologues against WCR_

TABLE 6

_Insecticidal activity of Pseudomonas sp. OF001 at various dilutions against WCR_

| | SEQ ID NO. | Day 3 | | | Day 6 | | |
|---|---|---|---|---|---|---|---|
| Treatment | | n | Mortality | Remarks | n | Mortality | Remarks |
| BL21*/pET29a-emp | | 12 | – | b | 12 | – | b |
| BL21*/OF001 1:4 | 2 | 11 | ++ | m/mb | 11 | ++++ | |
| BL21*/OF001 1:16 | 2 | 12 | ++ | mb/m | 12 | ++++ | 1m, 2mb |

TABLE 7

_Insecticidal activity of Streptomyces hainanensis orthologue against WCR_

| | SEQ ID NO. | Day 3 | | | Day 6 | | |
|---|---|---|---|---|---|---|---|
| Treatment | | n | Mortality | Remarks | n | Mortality | Remarks |
| BL21*/pET29a-emp | | 12 | – | b | 12 | + | b |
| BL21*/*S. hainanensis* | 12 | 12 | – | b | 12 | +++ | mb/b |

Example 2: Variants of ITD-46 Possess Insecticidal Activity Against WCR

Mutations were introduced into the c-terminus domain of ITD-46 (ITD-46_Cterm_mod1, SEQ ID NO: 10 and ITD-46_Nterm_mod1, SEQ ID NO:8 and ITD-46_Nterm_mod2, SEQ ID NO: 9)) and the insecticidal activity of bacterial lysates comprising the mutant variants were assayed. Chimeras of ITD-46 and the Methanosarcinaceae orthologue were produced (SEQ ID NO: 11 and SEQ ID: 12) and the insecticidal activity of bacterial lysates comprising the chimeras were assayed. Insecticidal activity was determined using diet-incorporation assays essentially as described in Example 1, using 12 WCR larvae per experimental assay. Results are shown in Table 8 and 9. SEQ ID NOs correspond to the amino acid sequence of the variant. Most variants tested displayed activity at day 3 and more activity by day 6. Notably, the N-term ITD-46-C-term-Methanosarcinaceae chimera did not have insecticidal activity, but the N-term-Methanosarcinaceae-C-term-ITD-46 chimera did.

TABLE 8

_Insecticidal activity of ITD-46 point mutants against WCR_

| | SEQ ID NO. | Day 3 | | | Day 6 | | |
|---|---|---|---|---|---|---|---|
| Treatment | | n | Mortality | Remarks | n | Mortality | Remarks |
| BL21*/pET29a-emp | | 12 | – | b | 12 | – | b |
| BL21*/ITD-46_Cterm_mod1 | 10 | 12 | + | b | 12 | ++++ | 1mb |
| BL21*/ITD-46_Nterm_mod1 | 8 | 12 | ++ | m/mb | 12 | ++++ | |
| BL21*/ITD-46_Nterm_mod2 | 9 | 12 | +++ | m/mb | 12 | ++++ | |

TABLE 9

Insecticidal activity of ITD-46 and *Methanosarcinaceae* chimeras against WCR

| Treatment | SEQ ID NO. | Day 3 | | | Day 6 | | |
|---|---|---|---|---|---|---|---|
| | | n | Mortality | Remarks | n | Mortality | Remarks |
| BL21*/pET29a-emp | | 12 | – | b | 12 | – | b |
| BL21*/ITD-46 - Methano. | 12 | 12 | – | b | 12 | – | b |
| B21*/Methano- ITD-46 | 11 | 12 | ++ | mb/b | 12 | ++++ | m/mb |

Example 3: Purified ITD-46 Protein is Insecticidal Against WCR

ITD-46 protein was purified to further characterize its insecticidal properties. A pET-6His-SUMO construct was produced for ITD-46 for protein production. Two liters of *E. coli* BL21* (DE3) cells harboring pET-6His-SUMO-ITD-46 were grown at 37° C. in LB media. IPTG (1 mM) was added to the cultures when the O.D. reached 0.8-1.0 and then the cultures were moved to 18° C. for 18 hours. The cell pellet was harvested and re-suspended in 20 mM Tris, pH 8.5 with 10% glycerol. The cells were lysed using a French pressure cell; the lysate was then spun at 100k×g in an ultracentrifuge.

Following centrifugation, the supernatants for SUMO-tagged ITD-46 were collected and protein for both samples purified using standard techniques for a His-tagged protein. SUMO protease was used to cleave the tag and liberate tag-free proteins.

The supernatant fraction for ITD-46 was collected and then filtered before loading onto a HiPrepQ anion-exchange column that was pre-equilibrated in 20 mM Tris, pH 8.5 with 10% glycerol. The HiPrepQ column bound Nitroso_haloCRW effectively; the protein was eluted from the column using a linear NaCl gradient. The high-salt buffer consisted of 20 mM Tris, pH 8.5, 0.5 M NaCl with 10% glycerol.

The purest fractions collected for the proteins were pooled and then concentrated to approximately 2 mL. The proteins were loaded onto a Sephadex 200 gel filtration column that had been pre-equilibrated in 1×PBS. Fractions from the Sephadex 200 column were analyzed for purity by SDS-PAGE. The purest fractions were pooled and then concentrated prior to storage at –80° C. The pure proteins were then tested against 12 WCR larvae over a range of concentrations in the diet-incorporation method essentially as described in Example 1. As shown in Table 10, the protein displays concentration dependent bioactivity to WCR over the range of concentrations tested.

TABLE 10

Dose Response for purified ITD-46 protein against WCR

| Treatment | SEQ ID NO. | Day 4 | | | Day 6 | | |
|---|---|---|---|---|---|---|---|
| | | n | Mortality | Remarks | n | Mortality | Remarks |
| 1X PBS | | 12 | + | b | 12 | + | b |
| ITD-46 200 µg/ml | 1 | 12 | +++ | M | 12 | ++++ | |
| ITD-46 100 µg/ml | 1 | 12 | +++ | mb/b | 12 | ++++ | 3mb |
| ITD-46 50 µg/ml | 1 | 12 | – | mb/b | 12 | ++ | 2mb, 5b |
| ITD-46 25 µg/ml | 1 | 12 | + | mb/b | 12 | + | 4mb, 6b |
| ITD-46 12.5 µg/ml | 1 | 12 | – | 2mb, 10b | 12 | + | b |

Example 4: Purified OF001 Protein is Insecticidal Against WCR

Purified *Pseudomonas* sp. OF001 protein was produced essentially as described in Example 3 for ITD-46. The protein was tested essentially as described in Example 3 for ITD-46. As shown in Table 11, by Day 6 the protein displays concentration dependent bioactivity to WCR over the range of concentrations tested.

TABLE 11

Dose Response for purified *Pseudomonas* sp. OF001 protein against WCR

| Treatment | SEQ ID NO. | Day 3 | | | Day 6 | | |
|---|---|---|---|---|---|---|---|
| | | n | Mortality | Remarks | n | Mortality | Remarks |
| 1X PBS | | 12 | – | b | 12 | + | b |
| OF001 200 µg/ml | 2 | 12 | – | M | 12 | ++++ | sm/m |
| OF001 100 µg/ml | 2 | 12 | – | mb/b | 12 | ++++ | m/mb |

TABLE 11-continued

Dose Response for purified *Pseudomonas* sp. OF001 protein against WCR

|  | SEQ ID | Day 3 | | | Day 6 | | |
|---|---|---|---|---|---|---|---|
| Treatment | NO. | n | Mortality | Remarks | n | Mortality | Remarks |
| OF001 50 µg/ml | 2 | 12 | – | mb/b | 12 | ++ | mb/b |
| OF001 25 µg/ml | 2 | 12 | – | mb/b | 12 | + | mb/b |
| OF001 12.5 µg/ml | 2 | 12 | – | 2mb, 10b | 12 | + | b |

Example 5: Maize Transformation

Transformation of immature maize embryos is performed essentially as described in Negrotto et al. (*Plant Cell Reports* (2000) 19:798-803). Briefly, *Agrobacterium* strain LBA4404 (pSB1) comprising an expression vector expressing the disclosed insecticidal proteins in Example 1 is grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* cells are suspended in LS-inf media supplemented with 100 µM As. Bacteria are pre-induced in this medium for approximately 30-60 minutes.

Immature embryos from an inbred maize line are excised from 8-12 day old ears into liquid LS-inf+100 µM As. Embryos are rinsed once with fresh infection medium. *Agrobacterium* solution is then added, and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/l) and silver nitrate (1.6 mg/l) and cultured in the dark at approximately 28° C. for 10 days.

Immature embryos, producing embryogenic callus are transferred to LSD1M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the selectable marker gene and the disclosed insecticidal genes by PCR. Positive plants from the PCR assay are transferred to a greenhouse for further evaluation.

Example 6: Expression Activity of ITD-46 and Orthologue Proteins in Maize Plants The presence of the disclosed proteins in Example 1 are detected by ELISA (ng/mg total soluble protein (TSP)) in leaf and root tissue samples from each event. It is believed that the expression of disclosed proteins in maize events will provide protection from western corn rootworm in a whole plant bioassay.

Example 7: Alanine Scanning Site-Directed Mutagenesis of ITD-46

Mutations were introduced into the C-terminus of ITD-46 using Alanine scanning site-directed mutagenesis at residues which may be associated with receptor binding. Approximately 100 variants were created and the insecticidal activity of bacterial lysates comprising the mutant variants were assayed. Insecticidal activity was determined using diet-incorporation assays essentially as described in Example 1, using 12 WCR larvae per experimental assay. Results are shown in Table 12. SEQ ID NOS correspond to the amino acid sequence of the variant. Most variants tested displayed activity at day 4 and more activity by day 6. As shown in Table 12, the majority of the variants were still active against WCR.

TABLE 12

Insecticidal activity of ITD-46 Alanine scanning variants against WCR

| Treatment | SEQ ID NO | Day 4 | | | Day 6 | | |
|---|---|---|---|---|---|---|---|
|  |  | n | Mortality | Remarks | Dead | Mortality | Remarks |
| BL21*/pET29a-empty |  | 12 | + | b | 12 | + | b |
| BL21*/ITD-46 Q246A | 29 | 12 | ++++ | m | 12 | ++++ |  |
| BL21*/ITD-46 Y247A | 30 | 12 | + | mb/b | 12 | ++ | mb/b |
| BL21*/ITD-46 F248A | 31 | 12 | ++ | mb/b | 12 | ++++ | mb/b |
| BL21*/ITD-46 D249A | 32 | 12 | – | mb/b | 12 | +++ | mb/b |
| BL21*/ITD-46 P250A | 33 | 12 | ++++ | m | 12 | ++++ |  |
| BL21*/ITD-46 V251A | 34 | 12 | +++ | m/mb | 12 | ++++ |  |
| BL21*/ITD-46 K252A | 35 | 12 | ++++ | m | 12 | ++++ |  |
| BL21*/ITD-46 Y253A | 36 | 12 | ++++ |  | 12 | ++++ |  |
| BL21*/ITD-46 P254A | 37 | 12 | ++ | m/mb | 12 | ++++ | b |
| BL21*/ITD-46 T255A | 38 | 12 | ++++ | m | 12 | ++++ |  |
| BL21*/ITD-46 P256A | 39 | 12 | ++++ |  | 12 | ++++ |  |
| BL21*/ITD-46 A257G | 40 | 12 | ++++ |  | 12 | ++++ |  |
| BL21*/ITD-46 E258A | 41 | 12 | ++++ |  | 12 | ++++ |  |
| BL21*/ITD-46 V259A | 42 | 12 | ++++ | m | 12 | ++++ |  |

TABLE 12-continued

Insecticidal activity of ITD-46 Alanine scanning variants against WCR

| | | | Day 4 | | | Day 6 | |
|---|---|---|---|---|---|---|---|
| Treatment | SEQ ID NO | n | Mortality | Remarks | Dead | Mortality | Remarks |
| BL21*/ITD-46 Y260A | 43 | 12 | ++++ | mb | 12 | ++++ | |
| BL21*/ITD-46 L261A | 44 | 12 | ++ | m/mb | 12 | +++ | b |
| BL21*/ITD-46 S262A | 45 | 12 | ++++ | | 12 | ++++ | |
| BL21*/ITD-46 R263A | 46 | 12 | – | b | 12 | + | b |
| BL21*/ITD-46 E264A | 47 | 12 | ++ | mb/b | 12 | ++++ | b |
| BL21*/ITD-46 I265A | 48 | 12 | – | b | 12 | + | b |
| BL21*/ITD-46 Y266A | 49 | 12 | ++++ | | 12 | ++++ | |
| BL21*/ITD-46 S267A | 50 | 12 | +++ | sm | 12 | ++++ | sm |
| BL21*/ITD-46 D268A | 51 | 12 | ++ | sm | 12 | ++++ | |
| BL21*/ITD-46 A269G | 52 | 12 | ++ | sm | 12 | ++++ | |
| BL21*/ITD-46 V270A | 53 | 12 | ++ | sm | 12 | ++++ | sm |
| BL21*/ITD-46 G271A | 54 | 12 | +++ | sm | 12 | ++++ | sm |
| BL21*/ITD-46 T272A | 55 | 12 | ++ | sm | 12 | ++++ | sm |
| BL21*/ITD-46 A273G | 56 | 12 | ++++ | sm | 12 | ++++ | sm |
| BL21*/ITD-46 D274A | 57 | 12 | ++ | sm | 12 | +++ | sm |
| BL21*/ITD-46 N275A | 58 | 12 | ++ | sm | 12 | +++ | sm |
| BL21*/ITD-46 S276A | 59 | 12 | +++ | sm | 12 | ++++ | |
| BL21*/ITD-46 G277A | 60 | 12 | +++ | sm | 12 | ++++ | |
| BL21*/ITD-46 A278G | 61 | 12 | ++++ | | 12 | ++++ | |
| BL21*/ITD-46 I279A | 62 | 12 | ++ | sm | 12 | ++++ | sm |
| BL21*/ITD-46 K280A | 63 | 12 | ++++ | sm | 12 | ++++ | |
| BL21*/ITD-46 L281A | 64 | 12 | +++ | m/mb | 12 | ++++ | |
| BL21*/ITD-46 P282A | 65 | 12 | +++ | m/mb | 12 | ++++ | |
| BL21*/ITD-46 S283A | 66 | 12 | +++ | m/mb | 12 | ++++ | |
| BL21*/ITD-46 A284G | 67 | 12 | ++++ | s/sm | 12 | ++++ | |
| BL21*/ITD-46 P285A | 68 | 12 | ++ | sm/m | 12 | ++++ | |
| BL21*/ITD-46 K286A | 69 | 12 | +++ | m | 12 | ++++ | |
| BL21*/ITD-46 Q287A | 70 | 12 | ++++ | m | 12 | ++++ | |
| BL21*/ITD-46 P288A | 71 | 12 | ++++ | sm/m | 12 | ++++ | |
| BL21*/ITD-46 I289A | 72 | 12 | ++ | m/mb | 12 | ++++ | |
| BL21*/ITD-46 S290A | 73 | 12 | +++ | m/mb | 12 | ++++ | |
| BL21*/ITD-46 K291A | 74 | 12 | +++ | sm/m | 12 | ++++ | |
| BL21*/ITD-46 V292A | 75 | 12 | +++ | m/mb | 12 | ++++ | sm/m |
| BL21*/ITD-46 E293A | 76 | 12 | – | b | 12 | ++++ | |
| BL21*/ITD-46 V294A | 77 | 12 | + | b | 12 | ++++ | |
| BL21*/ITD-46 W295A | 78 | 12 | + | b | 12 | ++++ | sm/m |
| BL21*/ITD-46 A296G | 79 | 12 | ++++ | m | 12 | ++++ | |
| BL21*/ITD-46 W297A | 80 | 12 | ++++ | m/mb | 12 | ++++ | |
| BL21*/ITD-46 D298A | 81 | 12 | – | b | 12 | + | b |
| BL21*/ITD-46 R299A | 82 | 12 | – | b | 12 | ++++ | |
| BL21*/ITD-46 I300A | 83 | 12 | – | b | 12 | ++++ | |
| BL21*/ITD-46 D301A | 84 | 12 | – | b | 12 | ++++ | |
| BL21*/ITD-46 A302G | 85 | 12 | ++++ | m | 12 | ++++ | |
| BL21*/ITD-46 C303A | 86 | 12 | ++++ | m | 12 | ++++ | |
| BL21*/ITD-46 R304A | 87 | 12 | ++++ | | 12 | ++++ | |
| BL21*/ITD-46 V305A | 88 | 12 | ++++ | | 12 | ++++ | |
| BL21*/ITD-46 T306A | 89 | 12 | ++++ | m/mb | 12 | ++++ | |
| BL21*/ITD-46 Y307A | 90 | 12 | + | b | 12 | ++ | b |
| BL21*/ITD-46 P308A | 91 | 12 | ++++ | m | 12 | ++++ | |
| BL21*/ITD-46 N309A | 92 | 12 | ++++ | | 12 | ++++ | |
| BL21*/ITD-46 G310A | 93 | 12 | ++++ | sm | 12 | ++++ | |
| BL21*/ITD-46 G311A | 94 | 12 | ++++ | m/mb | 12 | ++++ | |
| BL21*/ITD-46 G312A | 95 | 12 | ++ | b | 12 | +++ | mb/b |
| BL21*/ITD-46 P313A | 96 | 12 | ++ | mb/b | 12 | ++++ | b |
| BL21*/ITD-46 G314A | 97 | 12 | ++++ | m | 12 | ++++ | |
| BL21*/ITD-46 G315A | 98 | 12 | ++++ | m | 12 | ++++ | mb |
| BL21*/ITD-46 V316A | 99 | 12 | ++++ | m | 12 | ++++ | |
| BL21*/ITD-46 T317A | 100 | 12 | ++++ | m | 12 | ++++ | |
| BL21*/ITD-46 Q318A | 101 | 12 | +++ | mb/b | 12 | ++++ | m |
| BL21*/ITD-46 T319A | 102 | 12 | + | b | 12 | ++ | b |
| BL21*/ITD-46 A320G | 103 | 12 | ++++ | s | 12 | ++++ | |
| BL21*/ITD-46 R321A | 104 | 12 | ++++ | sm/m | 12 | ++++ | |
| BL21*/ITD-46 M322A | 105 | 12 | +++ | sm/m | 12 | ++++ | mb/b |
| BL21*/ITD-46 G323A | 106 | 12 | + | m/mb | 12 | +++ | mb/b |
| BL21*/ITD-46 D324A | 107 | 12 | +++ | m/mb | 12 | ++++ | |
| BL21*/ITD-46 K325A | 108 | 12 | ++++ | sm | 12 | ++++ | |
| BL21*/ITD-46 S326A | 109 | 12 | ++++ | sm | 12 | ++++ | |
| BL21*/ITD-46 G327A | 110 | 12 | ++++ | | 12 | ++++ | |
| BL21*/ITD-46 G328A | 111 | 12 | + | mb/b | 12 | ++++ | mb/b |
| BL21*/ITD-46 S329A | 112 | 12 | ++++ | | 12 | ++++ | |
| BL21*/ITD-46 S330A | 113 | 12 | ++++ | | 12 | ++++ | |
| BL21*/ITD-46 N331A | 114 | 12 | ++++ | | 12 | ++++ | |
| BL21*/ITD-46 P332A | 115 | 12 | ++++ | | 12 | ++++ | |
| BL21*/ITD-46 P333A | 116 | 12 | ++++ | | 12 | ++++ | |

TABLE 12-continued

Insecticidal activity of ITD-46 Alanine scanning variants against WCR

| Treatment | SEQ ID NO | n | Day 4 | | Day 6 | | |
|---|---|---|---|---|---|---|---|
| | | | Mortality | Remarks | Dead | Mortality | Remarks |
| BL21*/ITD-46 H334A | 117 | 12 | ++++ | | 12 | ++++ | |
| BL21*/ITD-46 G335A | 118 | 12 | ++++ | | 12 | ++++ | |
| BL21*/ITD-46 G336A | 119 | 12 | ++++ | | 12 | ++++ | |
| BL21*/ITD-46 V337A | 120 | 12 | ++++ | m | 12 | ++++ | |
| BL21*/ITD-46 F338A | 121 | 12 | ++++ | m/mb | 12 | ++++ | |
| BL21*/ITD-46 N339A | 122 | 12 | ++++ | | 12 | ++++ | |
| BL21*/ITD-46 L340A | 123 | 12 | ++++ | b | 12 | ++++ | m |
| BL21*/ITD-46 S341A | 124 | 12 | ++++ | | 12 | ++++ | |
| BL21*/ITD-46 G342A | 125 | 12 | ++++ | m | 12 | ++++ | |
| BL21*/ITD-46 E343A | 126 | 12 | ++++ | m | 12 | ++++ | |
| BL21*/ITD-46 N344A | 127 | 12 | ++++ | | 12 | ++++ | |
| BL21*/ITD-46 P345A | 128 | 12 | ++++ | | 12 | ++++ | |
| BL21*/ITD-46 I346A | 129 | 12 | ++++ | | 12 | ++++ | mb |
| BL21*/ITD-46 V347A | 130 | 12 | ++++ | mb/b | 12 | ++++ | |
| BL21*/ITD-46 K348A | 131 | 12 | ++++ | | 12 | ++++ | |
| BL21*/ITD-46 V349A | 132 | 12 | ++++ | | 12 | ++++ | |
| BL21*/ITD-46 T350A | 133 | 12 | ++++ | | 12 | ++++ | |
| BL21*/ITD-46 A351G | 134 | 12 | ++++ | | 12 | ++++ | |
| BL21*/ITD-46 R352A | 135 | 12 | ++++ | | 12 | ++++ | |
| BL21*/ITD-46 WT | 1 | 12 | +++ | m/mb | 12 | ++++ | b |

Example 8: Identification of an ITD-46 Orthologue from *Methanosarcina* sp. DH2

A protein orthologue was identified from *Methanosarcina* sp. DH2 sharing 88.7% identity to ITD-46. A chimera was created replacing the N-terminal portion of the sequence with that of ITD-46 and the insecticidal activity of the bacterial lysate comprising this chimera was assayed. Insecticidal activity was determined using diet-incorporation assays essentially as described in Example 1, using 12 WCR larvae per experimental assay. Results are shown in Table 13. SEQ ID NOs correspond to the amino acid sequence of the chimera. The chimera displayed activity by day 3 and more activity by day 6.

TABLE 13

Insecticidal activity of *Methanosarcina* sp. DH2/ITD-46 chimera against WCR

| Treatment | SEQ ID NO | Day 3 | | | Day 6 | | |
|---|---|---|---|---|---|---|---|
| | | n | Mortality | Remarks | n | Mortality | Remarks |
| BL21*/pET29a-empty | | 12 | – | b | 12 | + | b |
| BL21*/*Methanosarcina* sp. DH2_fixed_Nterm | 136 | 12 | ++ | mb/b | 12 | ++++ | |

---

What is claimed is:

1. A nucleic acid comprising a coding sequence that encodes a polypeptide comprising an amino acid sequence having at least 97% identity to the amino acid sequence set forth in SEQ ID NO: 1, wherein in the coding sequence is operably linked to a heterologous promoter.

2. The nucleic acid of claim 1, wherein the coding sequence comprises a nucleotide sequence comprising SEQ ID NO: 17.

3. The nucleic acid of claim 1, wherein the coding sequence is codon optimized for expression in a plant.

4. A vector comprising the nucleic acid of claim 1.

5. A transgenic host cell comprising a nucleic acid comprising a coding sequence that encodes a polypeptide comprising an amino acid sequence having at least 97% identity to the amino acid sequence set forth in SEQ ID NO: 1.

6. The transgenic host cell of claim 5, wherein the transgenic host cell is a plant cell.

7. The transgenic host cell of claim 6, wherein the plant cell is a maize cell.

8. The transgenic host cell of claim 5, wherein the transgenic host cell is a bacterial cell.

9. A plant comprising a nucleic acid sequence comprising a coding sequence that encodes a polypeptide comprising an amino acid sequence having at least 97% identity to the amino acid sequence set forth in SEQ ID NO: 1.

10. A seed of the plant of claim 9, wherein the seed comprises the nucleic acid comprising the coding sequence that encodes the polypeptide comprising the amino acid sequence having at least 97% identity to the amino acid sequence set forth in SEQ ID NO:1.

11. A method of producing a transgenic plant, the method comprising:

a) Introducing into a plant cell a nucleic acid comprising a coding sequence that encodes a polypeptide comprising an amino acid sequence having at least 97% identity to the amino acid sequence set forth in SEQ ID NO: 1;

b) Selecting a plant cell comprising the nucleic acid; and c) Regenerating a plant from the selected plant cell.

12. A method for producing a transgenic plant with enhanced insecticidal properties, comprising the steps of:

a) sexually crossing a first parent plant with a second parent plant, wherein the first or second parent plant is the plant of claim 9; and b) selecting a first generation progeny plant with enhanced insecticidal properties, wherein the selected progeny plant comprises the nucleic acid molecule.

13. The method of claim 12, further comprising the steps of:

a) selfing the first generation progeny plant, thereby producing a plurality of second generation progeny plants; and b) selecting from the second generation progeny plants a plant with enhanced insecticidal properties, wherein the selected second generation progeny plant comprises the nucleic acid molecule.

* * * * *

```
                            SEQUENCE LISTING

Sequence total quantity: 137
SEQ ID NO: 1          moltype = AA  length = 489
FEATURE               Location/Qualifiers
REGION                1..489
                      note = Sequence identified from Mgnify database - no source
                      organism canbe assigned
source                1..489
                      mol_type = protein
                      organism = unidentified
SEQUENCE: 1
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 2          moltype = AA  length = 496
FEATURE               Location/Qualifiers
REGION                1..496
```

-continued

```
                          note = Sequence identified from Genbank and designated in
                          Genbank asPseudomonas sp. OF001
source                    1..496
                          mol_type = protein
                          organism = unidentified
SEQUENCE: 2
MNDRIYIEHT FTGEAIAELR PQELVLRAEI SRAAGLTAGL EYEFDYNNAA RVVVSVVLGE    60
IPYAGQLLSA LVDIFWPDEK QDVWGEIADR VEALIDKKIS AEVMQDVRDA LTGLHNVSDD   120
YAYAAKNFPK DKAYVSEKFN VANGHFLHDL PRFQSSGYEV LLLPLFAQFA NLHLALLRDG   180
AAFGRDWGWS DELVADTRKK LTESIDSYSD YVTKTFEAGY ESVKKTAPED KRRMEPFNTV   240
NRYLREMTIT VKDFQAQWKY FDISRYPEPV KVYLDREVYS DAVGTCYDSP FYIPSRPTGR   300
IRNVTVWGWD RIDAVKVDYP EGGGPDGVTS TGRMGNAGGG SDQRPHGGSF DLSSNPIVGV   360
QVMSGDIVNA MSFQFADGAD TGMMGGNYRG GQKSTFSYAA QILSSIRVMG VSRFYGSADC   420
AVFGFKFDER ATKSQDLYAR LYRTSPRDIT PEELIEQFNV EPEHAQTIRE AAEREQWGEQ   480
RARYWARKQE RLNRAD                                                   496

SEQ ID NO: 3               moltype = AA   length = 487
FEATURE                    Location/Qualifiers
REGION                     1..487
                          note = Sequence identified from Genbank and designated in
                          Genbank asMethanosarcinaceae archaeon
source                    1..487
                          mol_type = protein
                          organism = unidentified
SEQUENCE: 3
MSDNQVMARV RVTEDGLEHV VYSAQVDYEF DYNNAAKVVI SASLGKIPVV GFALSALVGI    60
FWPASHVDVW AEVKEKVEAL VDRKISDLVY QQVQEDLKGL QNNMNEYLWA ARTSKVKTYI   120
SEKYNIVLGD FLQQLPHFQS KGYELPLLPL FAQFANMHLS LLRDGILHGA DWGWTEEIQQ   180
HTREQIVDAV SSYIKYAEKV YSDGLEDTRK KAPSNKHYTE PFNTVNRYVR EMTLTVLDFK   240
DMWQYFDPVK YPTPVKVYLS REIYSDAVGT ADDSGGIKIP SPPGQPISAV EVWGWDRIDA   300
CRVTYPEGGG PGGVTRTERM GNENGGSSNP PHGGVFDLSG SGPIVKVTAR STDILNAWWF   360
TFKDGSSSNK LGGNYPGGAD YVFTYPGEVL SSIKIMGVSY YYRSADCAVF GPKFEKEAAL   420
PDPTVLLMMY AASPSAIEPE ELAAYVGLQD SEEASEKIRA WIKDYHWDDI RERRWASIQE   480
SIEARKI                                                             487

SEQ ID NO: 4               moltype = AA   length = 504
FEATURE                    Location/Qualifiers
REGION                     1..504
                          note = Sequence identified from Genbank and designated in
                          Genbank asBurkholderia sp. ABCPW14
source                    1..504
                          mol_type = protein
                          organism = unidentified
SEQUENCE: 4
MQSLLRQDKQ ETVPSINNDD IYNIIRGVVL TGLGAIPYAG TLVSIVVDTF WPSAGPSAWD    60
QVKAQVNRMV DDKISEQEYQ LVSEFLTGLG NNLKSYLAAR QEASALEVAR IFSACHQIFI   120
NEAAQFQTSG RERLLLPLFV HFATLHLAML RDAILNRASL GWSDKEIAMY TKIATSAIRD   180
YKQYVSKVYS AIQADADSRA EAAASSDWSG TEKFRISNEC RRNYQLSVLD FSELFDYFDP   240
VKYPNKVDVE IRRVIYSDPV GSTYENQLNT DPPPCQIEMN VSSRSAKMAP PLGFDIYSGG   300
KWYGPGYTGG VVGYVSHYES GQGPNGTTID DHRRLNHQDD PMFKIDCTTE KGPVCRVLVP   360
RQDAVFSIQF FYKNGSSSPM AGGCLNNYPP NLEIAYDHHI LVDIAYQWYS RHTGCLGCIV   420
LGFQLENMGK NPDPLFSVRQ RYIYSLWEPK LPDLADFVRM QTGVYQQLNE ERLLEDVQSQ   480
LASWSNARRA FWENCRNALS KTTQ                                          504

SEQ ID NO: 5               moltype = AA   length = 453
FEATURE                    Location/Qualifiers
REGION                     1..453
                          note = Sequence identified from Genbank and designated in
                          Genbank asAcidobacteria bacterium
source                    1..453
                          mol_type = protein
                          organism = unidentified
SEQUENCE: 5
MQPSMGSQAT GAAMVTSSGF DWNNAAEQGI AGILGLVPEV GPLLSALVYI FWPQSKEDIW    60
GEIEAQVEAL IQKDLSQLVQ TEVSASLQGL NNVLNDYLLA LKDGTGDPTY ISEKWNIANG   120
DFLQQLPTFQ MSGYQVLLLP LFAQFSNMHL SLLRDGVLGG AKWGWTPAIL KQTQITLTST   180
IAAYAAYAQT TYQTGLTNVQ SSTPGNNQQA QPFRAVNQYV RQMTLTVLDF MNMWQYFDVS   240
KYPNGVSVYL NREIYSDPQG TCDDSGPIVL PSPPTAPISQ ISVWAWDRID AVQLTYPAGG   300
GPGGVTTTAR MGDQGGGSNS PPHGGVFQVA ANPVVTAGGL SGDIVNAMNF TFANGSSSGQ   360
LGGNYPGGGP FSYSYPNEIL SSIHINGISN YYGSADCVVY GFKFRQSNQL SADTERLLYV   420
TAPVVPSGTP EHSTVDQAAR NSYWKHLATK AKH                                453

SEQ ID NO: 6               moltype = AA   length = 487
FEATURE                    Location/Qualifiers
REGION                     1..487
                          note = Sequence identified from Genbank and designated in
                          Genbank asMethanosarcina sp. MTP4
source                    1..487
                          mol_type = protein
```

```
                         organism = unidentified
SEQUENCE: 6
MSNNQVMARV RVTEDGLEHV VYSTQVDYEF DYNNAAKVVI SASLGKIPVV GFALSALVGI     60
FWPASHVDVW AEVKEKVEAL VDRKISDLVY QQVQEDLKGL QNNMNEYLWA ARTSKVKTYI    120
SEKYNIVLGD FLQQLPHFQS KGYELPLLPL FAQFANMHLS LLRDGILHGA DWGWTEEIQQ    180
HTREQIVDTV SSYIKYSEKV YNDGLQDTQK KAPGNKHYTE PFNTVNKYVR EMTLTVLDFK    240
DMWQYFDPVK YPTPVKVYLS REIYSDAVGT ADDSGGIKLP SPPGQPISAV EVWGWDRIDA    300
CQVTYPEGGG PAGVTRTERM GNESGGSSNP PHGGVFDLSG TGPIVKVTAR STDILNAWWF    360
TFKDGSSSNK LGGNYPGGAD YVFAYPGEVL SSIKIMGISD FYRSADCAVF GPKFEKESTL    420
TDPAVLLRMY VASPSAIEPE ELAAYVGLQH SEEASEKIRA WIKDYHWDDI RERHWANIQE    480
SVEARKV                                                             487

SEQ ID NO: 7             moltype = AA  length = 700
FEATURE                  Location/Qualifiers
source                   1..700
                         mol_type = protein
                         organism = Streptomyces hainanensis
SEQUENCE: 7
MSLYTAETIP ATFLNAPEGG FRAQDLPKEE EDLLKTELMM VISQMALGPL GGLVGLVLNE     60
LWPNPQTDLK QVFQGILDKM MVVIERMVDE KIKTAVSNLY HKLMENELAG LYKVVDYYHT    120
VARTDPGNAP AAFISAHEQI LHDMPAFQDA DYGYLVLPFF AQVANLHIML LREGINYADE    180
LGLSDAHREE LIKMLKDVAS EDGAYTSYMK KTFDAHAFST GGSDECYLTL DYQRENYVRG    240
AEYGRYFWPA LADCNNAPEK LYREATVYLR CGSVLHMEDA AKPLVAPNYL YEHKREPALV    300
SYKADMHAPV SSDNGSSLLG LHLHYSDGHS TWYYADDMDE PAYTVNDSSE SGYSGVTLYL    360
DVQGGERDEL RGFAGWQLGD AKLSTYLHSA SAVHVEFKAK DWSVCDVRYA GRCNPLRNVY    420
ESGVIVGVHP TDEYITPDKQ FTVPSGALCR VHVAEGDGTL DLARYALSEA VPVVLRKHNG    480
SDSQLWQFQE AGENAFRLVN AYNGQALALR EGQVLTTSVL QEATSWALEV AEDHTQRLTA    540
TIGPGHHLAA DGNALTTTTP AAATGGQAGN ARWVVVVDPT RSLAKLRSTL PNLTTSLVNV    600
DGRSDLHMTL TNPTSGSTVE NWTLQFILPA EAGTALTTTS PVNVTAVEEE RGIHVTLIPT    660
GDQRDLHPGR AFSFVLATTN PAPAALPPAA VRLNDTAISG                          700

SEQ ID NO: 8             moltype = AA  length = 499
FEATURE                  Location/Qualifiers
REGION                   1..499
                         note = Synthetic polypeptide
source                   1..499
                         mol_type = protein
                         organism = synthetic construct
SEQUENCE: 8
MIVTENQVVL ETLVRKDAPE YTLYSAQADY ELDYNNAARV VISTALGEIP GVGFALSALV     60
EIFWPDSQED VWSEIKDQVE ALIDEKISDL VYQQVQEDLE GLKNNLDEYL WAVSSWQKNP    120
VSSQNSQTQT YISEKYNVAL GDFLQQLPHF QSKGYELLLL PLFAQFANMH LTLLRDGALY    180
GTSWGWTEEI QQHTRQQIVD TIGSYIEYTE TIYNQGLQDT KNMWQYFDP VKYPTPAEVY    240
IREMTLDVLD FKNMWQYFDP VKYPTPAEVY LSREIYSDAV GTADNSGAIK LPSAPKQPIS    300
KVEVWAWDRI DACRVTYPNG GGPGGVTQTA RMGDKSGGSS NPPHGGVFNL SGENPIVKVT    360
ARTGDIQNAW WFTFKDGSVS NELGGNYSGG SDHVFTYPDE ILSSIKIMGI SNYYGSADCA    420
VFGFKFDRES TLPAQAVLQK MYVSSPSALK PEELAGYVGF KNSEEAIEKI RIWIKDYNWD    480
EIRERRWANI RESVIARRT                                                 499

SEQ ID NO: 9             moltype = AA  length = 500
FEATURE                  Location/Qualifiers
REGION                   1..500
                         note = Synthetic polypeptide
source                   1..500
                         mol_type = protein
                         organism = synthetic construct
SEQUENCE: 9
MIVTENQVVL ETLVRKDAPE YTLYSAQADY ELDYNNAARV VISTALGEIP GVGFALSALV     60
EIFWPDSQED VWSEIKDQVE ALIDEKISDL VYQQVQEDLE GLKNNLDEYL WAVSSWQKNP    120
AAPFQNSQTQ TYISEKYNVA LGDFLQQLPH FQSKGYELLL LPLFAQFANM HLTLLRDGAL    180
YGTSWGWTEE IQQHTRQQIV DTIGSYIEYT ETIYNQGLQD TQKNAPSNKH YTEPFNTVNR    240
YIREMTLDVL DFKNMWQYFD PVKYPTPAEV YLSREIYSDA VGTADNSGAI KLPSAPKQPI    300
SKVEVWAWDR IDACRVTYPN GGGPGGVTQT ARMGDKSGGS SNPPHGGVFN LSGENPIVKV    360
TARTGDIQNA WWFTFKDGSV SNELGGNYSG GSDHVFTYPD EILSSIKIMG ISNYYGSADC    420
AVFGFKFDRE STLPAQAVLQ KMYVSSPSAL KPEELAGYVG FKNSEEAIEK IRIWIKDYNW    480
DEIRERRWAN IRESVIARRT                                                500

SEQ ID NO: 10            moltype = AA  length = 662
FEATURE                  Location/Qualifiers
REGION                   1..662
                         note = Synthetic polypeptide
source                   1..662
                         mol_type = protein
                         organism = synthetic construct
SEQUENCE: 10
MIVTENQVVL ETLVRKDAPE YTLYSAQADY ELDYNNAARV VISTALGEIP GVGFALSALV     60
EIFWPDSQED VWSEIKDQVE ALIDEKISDL VYQQVQEDLE GLKNNLDEYL WAVQNSQTQT    120
YISEKYNVAL GDFLQQLPHF QSKGYELLLL PLFAQFANMH LTLLRDGALY GTSWGWTEEI    180
QQHTRQQIVD TIGSYIEYTE TIYNQGLQDT QKNAPSNKHY TEPFNTVNRY IREMTLDVLD    240
```

```
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRTL TKSTNLGSGT SVVKGPGFTG GDILRRTSPG QISTLRVNIT APLSQRYRVR  540
IRYASTTNLQ FHTSIDGRPI NQGNFSATMS SGSNLQSGSF RTVGFTTPFN FSNGSSVFTL  600
SAHVFNSGNE VYIDRIEFVP AEVTFEAEYD LERAQKAVNE LFTSSNQIGL KTDVTDYHID  660
QV                                                                  662

SEQ ID NO: 11          moltype = AA  length = 487
FEATURE                Location/Qualifiers
REGION                 1..487
                       note = Synthetic polypeptide
source                 1..487
                       mol_type = protein
                       organism = synthetic construct
SEQUENCE: 11
MSDNQVMARV RVTEDGLEHV VYSAQVDYEF DYNNAAKVVI SASLGKIPVV GFALSALVGI  60
FWPASHVDVW AEVKEKVEAL VDRKISDLVY QQVQEDLKGL QNNMNEYLWA ARTSKVKTYI  120
SEKYNIVLGD FLQQLPHFQS KGYELPLLPL FAQFANMHLS LLRDGILHGA DWGWTEEIQQ  180
HTREQIVDAV SSYIKYAEKV YSDGLEDTRK KAPSNKHYTE PFNTVNRYVR EMTLTVLDFK  240
DMWQYFDPVK YPTPAEVYLS REIYSDAVGT ADNSGAIKLP SAPKQPISKV EVWAWDRIDA  300
CRVTYPNGGG PGGVTQTARM GDKSGGSSNP PHGGVFNLSG ENPIVKVTAR TGDIQNAWWF  360
TFKDGSVSNE LGGNYSGGSD HVFTYPDEIL SSIKIMGISN YYGSADCAVF GFKFDRESTL  420
PAQAVLQKMY VSSPSALKPE ELAGYVGFKN SEEAIEKIRI WIKDYNWDEI RERRWANIRE  480
SVIARRT                                                            487

SEQ ID NO: 12          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 12
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPVKVY LSREIYSDAV GTADDSGGIK IPSPPGQPIS AVEVWGWDRI  300
DACRVTYPEG GGPGGVTRTE RMGNENGGSS NPPHGGVFDL SGSGPIVKVT ARSTDILNAW  360
WFTFKDGSSS NKLGGNYPGG ADYVFTYPGE VLSSIKIMGV SYYYRSADCA VFGFKFEKEA  420
ALPDPTVLLM MYAASPSAIE PEELAAYVGL QDSEEASEKI RAWIKDYHWD DIRERRWASI  480
QESIEARKI                                                          489

SEQ ID NO: 13          moltype = DNA  length = 1491
FEATURE                Location/Qualifiers
misc_feature           1..1491
                       note = Sequence identified from Genbank and designated in
                        Genbank asPseudomonas sp. OF001
source                 1..1491
                       mol_type = genomic DNA
                       organism = unidentified
SEQUENCE: 13
atgaatgatc gtatctatat agaacatact ttcaccggcg aagccattgc cgaactcaga  60
ccacaagagc tggttctgcg cgccgaaatt tccagggccg cggggctgac cgccggactg  120
gaatacgagt ttgactacaa caacgcggct cgtgtcgtgg tgtccgtggt gcttggggag  180
atcccctatg ccggccaact gctgagcgcc ctggtagaca tcttctggcc cgatgagaag  240
caggatgtgt ggggcgaaat tgccgaccgc gtggaagccc tgatcgacaa gaagatctcc  300
gccgaggtca tgcaggatgt gcgagacgcc ctcaccggac tgcacaacgt ctcggacgac  360
tacgcctatg cggccaagaa cttcccgaag gacaaggcct acgtctccga gaagttcaac  420
gtcgccaacg gacacttcct gcatgacctg ccgcgcttcc agtcgagtgg ctacgaggtg  480
ctgttgctgc ccctgttcgc ccagttcgcg aacctccacc tcgccctgct gcgcgacggc  540
gccgcattcg gccgtgactg gggttggagc gacgagctcg tcgccgatac ccgcaagaag  600
ctcaccgaaa gcatcgacag ctacagcgac tatgtcacca agacattcga agccggttat  660
gaaagcgtga agaagacggc gccggaagat aaggccgca tggagccgtt caacacggtg  720
aatcgctacc tgcgtgaaat gaccatcacg gtcaaggact tccaggcgca gtggaaatac  780
ttcgacatct ctcgttatcc ggagccggtc aaggtctatc tggatcgcga ggtgtactcc  840
gatgccgtgg gcacttgcta cgactccccg ttctatatcc cgagccgcac gacaggccgg  900
atcaggaatg taacggtatg gggttgggac cgaatcgatg ccgtcaaggt cgattatccg  960
gaaggcggtg gccgatggg agtgaccagc accgggcgca tgggcaacgc cggaggcgga  1020
agcgaccaac gcccgcatgg tggcagcttc gacctcagca gcaatccaat cgtcggcgtc  1080
caggtgatga gtgggatat cgtcaatgcc atgtcgttcc agttcgcaga tggcgcggac  1140
acgggcatga tggggggcaa ctaccggggc gggcagaagt ccacctcag ctacgccgca  1200
cagatcctgt ccagcatcag ggtcatgggc gtcagccggt tctacggcag cgccgactgc  1260
gccgttttcg ggttcaagtt cgacgagcgc gctaccaagt cccaggatct ctacgctcgc  1320
ctgtatagaa ccagcccccg cgacatcacg ccggaagagc tgatcgaaca gttcaacgtc  1380
gaacccgagc atgcacagac cattcgcgag gctgccgagc gagagcagtg gggcgagcag  1440
cgtgcacgct actgggcgcg gaagcaggaa cggctgaaca gagccgactg a           1491
```

-continued

```
SEQ ID NO: 14            moltype = DNA  length = 1515
FEATURE                  Location/Qualifiers
misc_feature             1..1515
                         note = Sequence identified from Genbank and designated in
                          Genbank asBurkholderia sp. ABCPW14
source                   1..1515
                         mol_type = genomic DNA
                         organism = unidentified
SEQUENCE: 14
gtgcagagtt tgcttcgcca agataaacaa gagaccgtgc ctagcataaa caatgacgat   60
atttataaca tcattcgcgg ggtagtgcta accgggcttg gagcgatacc gtacgctggc  120
actctcgtaa gtatcgttgt agacaccttc tggcccagtg caggcccgtc cgcatgggac  180
caggttaagg cgcaagtcaa taggatggta gacgacaaga tttctgagca agaataccag  240
ctagtaagcg aattcctcac gggggttgggt aacaatctga aatcctatct agccgctaga  300
caagaggctt ccgcactaga agtggcgcgc attttttctg cctgccatca aatttttata  360
aacgaggcag cacaatttca aacaagcggt agggaacgcc tgttgcttcc acttttcgta  420
catttcgcta cgcttcattt agcgatgcta cgtgacgcaa ttttgaatcg cgccagtctg  480
gggtggagcg ataaagaaat cgcaatgtat acgaagattg caacaagtgc aatccgagac  540
tataaacaat atgtatcaaa ggtgtattct gccattcagg cagatgctga tagtcgcgct  600
gaggctgcgg cttcttcgga ttggagtggc actgagaaat tcagaatttc gaacgaatgc  660
aggagaaact atcaactatc agttttggac tttagcgaac tgttcgatta ctttgatcct  720
gttaagtatc cgaacaaggt ggacgttgag atccgtcggg tgatctatag cgatccagtc  780
ggttcaacgt atgaaaacca gctcaacaca gatccgccgc catgtcaaat cgaaatgaat  840
gtgagcagtc gatcggcaaa gatggctccg cctcttggtt ttgatatcta ttcaggggggg  900
aaatggtatg gaccgggata cacgggcgga gtggttgatt atgttagtca ttatgaatcg  960
gggcagggggc cgaatggtac tacaatagac gatcataggc ggctcaatca tcaagatgat 1020
ccgatgttta aaatcgactg cacaacagaa aaaggtccag tgtgtagggt attagtgccc 1080
agacaggacg cagtttttttc gattcaattt ttctataaaa atggcagttc gtcacccatg 1140
gcgggcggggt gcctaaataa ctatccacca aacctggaac tcgcatacga ccaccacata 1200
cttgttgata tcgcctacca atggtatagc cgacataccg ggtgtctcgg gtgtatagtt 1260
ttgggatttc agctagagaa catggggaaa aatcccgatc cattattttc agtgcgtcag 1320
cgctacatct attctctttg ggaaccaaaa ttgccagacc ttgccgattt cgtcagaatg 1380
caaactggtg tttatcaaca attgaacgag gagcggttac tcgaggacgt ccagtcacaa 1440
ttggcgagtt ggtcaaatgc gcgccgggct ttttgggaaa actgcaggaa cgcactgtcc 1500
aaaactactc aatag                                                   1515

SEQ ID NO: 15            moltype = DNA  length = 1446
FEATURE                  Location/Qualifiers
misc_feature             1..1446
                         note = Sequence identified from Genbank and designated in
                          Genbank asMethanosarcina sp. MTP4
source                   1..1446
                         mol_type = genomic DNA
                         organism = unidentified
SEQUENCE: 15
atggcaagag ttcgggttac ggaggacggg cttgaacatg tagtgtattc cactcaggtt   60
gactatgagt tcgattataa taatgcggca aaagtggtca tatccgcatc tctcggtaaa  120
attccggtag tgggtttttgc tttaagtgcc cttgtcggga tcttctggcc ggcatcgcat  180
gtggatgtgt gggcggaagt taaggagaaa gtggaagcac tcgtggaccg gaaaatcagt  240
gacctggttt accagcaggt ccaggaagac ctcaagggct tgcagaacaa catgaatgaa  300
tacttatggg ctgccaggac ctcgaaggtt aaaacgtaca tatccgagaa atacaacatc  360
gtactgggggg attttctcca gcagctcccg catttccagt cgaagggtta cgagcttcct  420
ttgcttccgc tttttgcgca atttgcaaac atgcacctga gcctccttcg ggacggtatt  480
ttacacgggg ctgactgggg gtggacagag gaaatacaac agcatacccg cgagcagatt  540
gtagacacgg tcagctctta cataaaatat tctgagaagg tttacaacga tggtttgcag  600
gatacgcaga aaaaggctcc cggcaataag cattataccg aaccgtttaa cacggtaaat  660
aaatacgtcc gggaaatgac actcaccgtt ctggatttca aggacatgtg gcagtatttt  720
gatcctgtga agtaccccac acctgtaaag gtgtaccttt ccaggagag ttactctgat  780
gcggtgggaa cggctgatga cagcggtgga attaaactcc cctctccgcc aggacaaccg  840
atctcagcgg ttgaagtctg gggctgggac cggattgatg cctgccaggt tacttatccg  900
gaaggcgggg ggcctgccggg ggttacccgg acagagcgca tgggcaacga gagtggtggg  960
agttcaaatc cacctcatgg aggggtttttc gacctttccg gaacagggcc gatcgtgaaa 1020
gttacagccc ggtccaccga cattctaaat gcctggtggt ttacctttaa agacggttct 1080
tccagcaaca aactcggagg aaactatccc ggcggggctg attacgtctt tgcctatccc 1140
ggcgaggttc tttcaagcat taaaattatg ggaataagcg acttttacag gagtgcagac 1200
tgcgctgttt ttggcttcaa attcgagaaa gaatcaaccc tgacggaccc ggctgttttttg 1260
ctcaggatgt atgttgcctc tccctctgca attgaacgg aagaactggc agcctatgtc 1320
ggactgcag actccgaaga agccagtgaa aagatccgac cctggataaa ggactaccac 1380
tgggacgata tccgcgaacg ccactgggcc aatattcagg aaagtgttga agcaagaaaa 1440
gtttga                                                             1446

SEQ ID NO: 16            moltype = DNA  length = 2103
FEATURE                  Location/Qualifiers
source                   1..2103
                         mol_type = genomic DNA
                         organism = Streptomyces hainanensis
SEQUENCE: 16
gtgtccctgt acaccgctga gacgattccg gccacgttcc tgaacgcgcc ggaaggtggc   60
```

-continued

```
ttcagggcgc aggacctgcc caaggaggaa gaggacctcc tgaagaccga gctcatgatg  120
gtgatctccc agatggctct tggtccgctg ggtgggctcg tggggctcgt gttgaacgag  180
ttgtggccca atccgcagac agatctgaag caggttttcc aggggatctt ggacaagatg  240
atggtggtca ttgagaggat ggtcgacgag aagatcaaga cggctgtctc gaatctctat  300
cacaagctga tggagaatga gttggctggc ttgtacaagg ttgttgacta ctatcacacc  360
gtcgcgcgca ccgatccggg aaatgcgcca gccgctttta tctccgctca cgagcagatt  420
cttcacgaca tgccggcttt tcaggacgcc gactatggct atctcgtgtt gccgttcttc  480
gctcaggtgg ccaacctgca catcatgctg cttcgcgagg gcatcaacta cgccgacgaa  540
cttggcctga gcgatgcgca tcgggaagag ctcatcaaga tgctcaagga tgtggcgtcg  600
gaggacgggg cctacacctc ctacatgaag aagaccttcg acgcccacgc cttcagtaca  660
ggtgggtcgg acgagtgcta cctgacgctg gactatcagc gtgagaacta cgtccggggc  720
gccgagtatg ggcggtattt ctggcccgcg ctcgccgatt gcaataatgc gccggagaaa  780
ctgtaccgtg aagccaccgt gtatcttcgc tgcgggtccg tgctccacat ggaggatgcg  840
gcgaagccgc tggtggcccc gaattatctc tacgagcaca agcgcgaacc ggcactcgtt  900
tcatacaagg cggacatgca tgcccctgtc tcttccgaca acggttcctc cttgctgggg  960
ttgcacttgc attactccga cggacattcc acttggtatt acgcagatga catggacgag  1020
cccgcttaca ccgtgaatga ttcgtcagag tctggatact ccggtgtcac gctctacctc  1080
gacgtgcagg ggggtgaaag ggacgagctc aggggtttcg ccggatggca actcggcgac  1140
gcgaaactct ccacgtatct gcatagcgca tcggctgttc acgtcgagtt caaagccaag  1200
gactggtccg tgtgcgacgt gagatacgca gggcgatgca atccgctgag gaacgtctac  1260
gaatcgggcg tcatcgtggg cgttcacccg actgatgagt acatcacgcc cgacaagcag  1320
ttcaccgtgc cgtcgggagc gttgtgccgg gtgcacgtcg ccgagggtga ctggacgctg  1380
gacctggcgc gttacgcgtt gtcggaggcg gtaccggtcg ttttgcgcaa gcacaacggg  1440
tccgactccc agctgtggca gttccaggag gccggtgaga acgcgttccg gctcgtgaac  1500
gcctacaacg gccaggccct cgccctccgt gagggggcagg tgctcaccac ctccgtcctc  1560
caggagcgag ccagctgggc cctggaggtc gccgaggatc acacccagcg cctcaccgcc  1620
acgatcggcc ccggccacca cctgcgcggc gacgggaacg ccctcaccac cacgacgccg  1680
gcggcggcga ccggagggca ggcgggaaac gcccggtggg tcgtggtcgt cgatcccacc  1740
cgcagcctgg ccaagctgcg ctccacgctg ccgaacctca ccacgagcct ggtcaacgtc  1800
gacggccgca gcgacctcca catgacgctg accaaccca cctccggtag cacggtggaa  1860
aactggaccc tccagttcat cctgcccgcc gaagccggca ccgccctgac caccacctcc  1920
cccgtcaacg tcaccgcggt cgaggaggaa cgcggcatcc acgtcaccct gatccccacc  1980
ggcgaccagc gcgacctcca ccccggcagg gccttctcct tcgtcctcgc caccaccaac  2040
cccgcaccgg ccgcactacc accagccgcg gtacgcctca acgacaccgc catcagcgga  2100
tag                                                                2103
```

```
SEQ ID NO: 17            moltype = DNA  length = 1470
FEATURE                  Location/Qualifiers
misc_feature             1..1470
                         note = Synthetic polynucleotide
source                   1..1470
                         mol_type = other DNA
                         organism = synthetic construct
SEQUENCE: 17
atgatcgtta ccgaaaacca ggttgttctg gaaaccctgg ttcgtaaaga cgcgccggaa  60
tacaccctgt actctgcgca ggcggactac gaactggact acaacaacgc ggcgcgtgtt  120
gttatctcta ccgcgctggg tgaaatcccg ggtgttggtt tcgcgctgtc tgcgctggtt  180
gaaatcttct ggccggactc tcaggaagac gtttggtctg aaatcaaaga ccaggttgaa  240
gcgctgatcg acgaaaaaat ctctgacctg gtttaccagc aggttcagga agaccctgga  300
ggtctgaaaa caacctgga cgaataccctg tgggcggttc agaactctca gacccagacc  360
tacatctctg aaaaatacaa cgttgcgctg ggtgacttcc tgcagcagct gccgcacttc  420
cagtctaaag gttacgaact gctgctgctg ccgctgttcg cgcagttcgc gaacatgcac  480
ctgaccctgc tgcgtgacgg tgcgctgtac ggtacctctt ggggttggac cgaagaaatc  540
cagcagcaca cccgtcagca gatcgttgac accatcggtt cttacatcga atacaccgaa  600
accatctaca accagggtct gcaggacacc cagaaaaacg cgcgtgtctaa caaacactac  660
accgaaccgt tcaacaccgt taaccgttac atccgtgaaa tgaccctgga cgttctggac  720
ttcaaaaaca tgtggcagta cttcgacccg gttaaataccc cgaccccgc ggaagtttac  780
ctgtctcgta aaatctactc tgacgcggtt ggtaccgcgg acaactctgg tgcgatcaaa  840
ctgccgtctg cgccgaaaca gccgatctct aaagttgaag tttgggcgtg ggaccgtatc  900
gacgcgtgcc gtgttaccta cccgaacggt ggtggtccgg gtgtgttac ccagaccgcg  960
cgtatgggtg acaaatctgg tggttcttct aacccgccgc acgtggtgt tttcaacctg  1020
tctggtgaaa acccgatcgt taaagttacc gcgcgtaccg gtgacatcca gaacgcgtgg  1080
tggttcacct tcaaagacgg ttctgtttct aacgaactgg gtggtaacta ctctggtggt  1140
tctgaccacg ttttcaccta cccggacgaa atcctgtctt ctatcaaaat catgggtatc  1200
tctaactact acggttctgc ggactgcgcg gtttcggtt caaattcga ccgtgaatct  1260
accctgccgg cgcaggcggt tctgcagaaa atgtacgttt cttctccgtc tgcgctgaaa  1320
ccggaagaac tggcgggtta cgttggtttc aaaaactctg aagaagcgat cgaaaaaatc  1380
cgtatctgga tcaaagacta caactgggac gaaatccgtg aacgtcgttg ggcgaacatc  1440
cgtgaatctg ttatcgcgcg tcgtacctaa                                    1470
```

```
SEQ ID NO: 18            moltype = DNA  length = 1491
FEATURE                  Location/Qualifiers
misc_feature             1..1491
                         note = Synthetic polynucleotide
source                   1..1491
                         mol_type = other DNA
                         organism = synthetic construct
SEQUENCE: 18
atgaacgacc gcatttatat cgagcacact tttaccggtg aagcgatcgc ggaactgcgt  60
```

```
cctcaggaac tggtgctgcg tgctgaaatt agccgtgcag cgggtctgac tgcaggtctg  120
gaatacgagt tcgactataa taacgcagcc cgtgttgtag tttccgtcgt tctgggcgag  180
attccatacg cgggtcagct cctgtccgca ctggtggaca ttttctggcc ggatgaaaag  240
caggatgtat ggggcgaaat tgcagatcgt gttgaagcgc tgattgacaa gaaaatcagc  300
gcggaagtca tgcaggacgt gcgcgacgct ctgacgggtc tgcacaacgt gtccgacgat  360
tatgcttatg cggctaaaaa ctttccaaaa gataaagctt atgtatctga aaaatttaac  420
gtcgccaacg gccacttcct gcatgacctg ccgcgttttc aaagctccgg ctacgaagtt  480
ctgctcctgc cgctgtttgc gcagtttgcg aacctgcacc tggctctcct gcgcgatggc  540
gcggcttttg gccgtgactg gggttggtcc gatgaactgg tagcggatac ccgtaaaaag  600
ctgactgaat ccattgactc ttacagcgac tacgttacca aaaccttcga agctggctat  660
gaatccgtga aaaagactgc gccggaagac aaacgccgta tggaaccgtt caacacggtc  720
aaccgttacc tgcgtgaaat gactattacc gtgaaggact ttcaggcgca gtggaaatac  780
ttcgatatct ctcgttaccc ggaaccggtt aaagtctacc tggaccgtga agtgtattct  840
gacgccgtcg gtacctgcta cgactctccg ttctacatcc cgagccgtcc tacgggccgc  900
atccgtaacg ttaccgtttg gggttgggat cgtatcgacg cggtgaaggt tgactacccg  960
gaaggtggcg gtccggatgg tgttacctcc actggccgta tgggcaatgc cggtggcggt  1020
agcgaccaac gtccgcatgg cggtagcttc gacctgtctt ccaacccaat cgttggtgtg  1080
caggtaatgt ctggtgatat cgttaacgca atgagcttcc agttcgccga tggcgcagat  1140
accggcatga tgggcggtaa ctaccgcggc ggtcagaaaa gcaccttcag ctatgccgcg  1200
cagatcctca gctctatccg tgtgatgggg gttagccgct tttatggcag cgcagattgc  1260
gccgtatttg gtttcaaatt tgacgagcgc gcaactaaaa gccaggacct gtacgcgcgc  1320
ctgtatcgta cgtccccgcg tgacatcacc ccggaggaac tgatcgaaca atttaacgtc  1380
gagccggaac acgctcagac cattcgtgaa gcggcagaac gtgaacagtg gggtgaacag  1440
cgtgctcgct attgggctcg taaacaagaa cgtctgaacc gcgcggatta a  1491
```

```
SEQ ID NO: 19          moltype = DNA  length = 1464
FEATURE                Location/Qualifiers
misc_feature           1..1464
                       note = Synthetic polynucleotide
source                 1..1464
                       mol_type = other DNA
                       organism = synthetic construct
SEQUENCE: 19
atgtccgata accaggtcat ggctcgtgtt cgcgttaccg aagacggcct ggaacacgtt  60
gtctatagcg ctcaggtgga ctacgagttc gactacaata acgccgcgaa ggtcgttatt  120
tctgcatccc tgggtaaaat cccggtcgtt ggttttgctc tctctgctct ggtgggtatc  180
ttctggccgg catccatgt agacgtgtgg gcggaggtta agaaaaagt ggaagcgctg  240
gtggatcgta aaatttctga tctggtttac caacaggtcc aagaagatct caaaggtctc  300
cagaataaca tgaacgaata tctgtgggct gcacgtacca gcaaagtgaa aacctacatc  360
tccgaaaaat acaacatcgt tctgggcgat ttcctgcagc aactgccaca cttccaaagc  420
aaaggctacg aactgccgct cctgccgctg tttgcgcagt ttgcgaacat gcatctgtct  480
ctcctgcgtg acggtatcct gcatggtgca gactggggct ggaccgaaga gattcaacag  540
cacacccgtg aacagatcgt tgacgcggta tcctcttata tcaaatatgc agaaaaagta  600
tactctgacg gcctggaaga tacccgcaaa aaggccccgt ctaacaaaca ttacacggaa  660
ccgtttaaca ccgttaaccg ttatgttcgt gagatgaccc tgaccgtact ggatttcaaa  720
gatatgtggc agtacttcga cccagttaaa tacccgactc cagttaaagt ttatctgtcc  780
cgtgagattt attctgatgc agttggtacc gctgatgact ctggtggcat caaaatcccg  840
tccccaccgg gtcagccgat ctctgcggtg gaggtttggg gttgggatcg tattgacgcg  900
tgccgtgtta cttacccgga aggtggcggt ccgggtggcg ttactcgtac cgaacgtatg  960
ggtaacgaaa acgcggttc tagcaaccct ccgcacggcg gtgttttcga cctgagcggt  1020
agcggcccga ttgtgaaagt gaccgcccgc tctacggaca ttctgaatgc atggtggttt  1080
accttcaaag acggcagctc cagcaacaaa ctcggtggca attatccggg cggtgccgac  1140
tacgtgttca cctacccagg tgaagtcctg tctagcatta agatcatggg cgtctcttac  1200
tattaccgct ccgcggattg cgcggttttt ggtttcaaat tcgaaaaaga agcggctctg  1260
cctgacccga ctgtgctcct gatgatgtac gcggcctccc cgtctgccat cgaaccggag  1320
gaactggcag cttacgttgg cctgcaggat agcgaggaag cttccgagaa aattcgtgct  1380
tggatcaaag attaccactg ggacgatatc cgtgaacgcc gttgggctag cattcaggaa  1440
tccatcgaag ctcgcaaaat ctaa  1464
```

```
SEQ ID NO: 20          moltype = DNA  length = 1515
FEATURE                Location/Qualifiers
misc_feature           1..1515
                       note = Synthetic polynucleotide
source                 1..1515
                       mol_type = other DNA
                       organism = synthetic construct
SEQUENCE: 20
atgcaaagcc tcctgcgtca ggacaaacag gaaacggttc cgtctatcaa taacgatgac  60
atctacaaca tcattcgtgg tgtagtgctg accggcctgg gtgctatccc gtatgcaggc  120
accctggtaa gcattgtagt ggacactttc tggccgtctg ccggcccatc cgcatgggat  180
caggtaaaag cgcaggtgaa ccgtatggtc gatgacaaaa tcagcgaaca ggaataccag  240
ctggtatctg aatttctgac cggtctgggt aacaatctga aaagctacct cgcggcacgc  300
caggaagctt ccgcactgga gtggctcgt atcttctctg cttgtcacca gatcttcatc  360
aacgaagcag cccaattcca aacctccggt cgtgaacgtc tgtcctgcc gctgttcgtt  420
cactttgcaa ccctgcacct ggcgatgctg cgtgacgcga ttctgaaccg tgcgtctctg  480
ggttggtctg acaagaaat tgctatgtac accaaaatcg cgacctctgc cattcgcgac  540
tacaagcaat acgtctctaa agtgtatagc gcgattcagg ctgatgcaga ttcccgtgcg  600
gaagcggcag cctcctctga ctggtccggc accgagaaat ttcgcatttc taacgaatgt  660
cgccgtaact atcaactgag cgtgctggac ttctctgaac tgttcgacta tttcgacccg  720
```

```
gttaaatatc cgaacaaagt cgatgttgag atccgccgtg tgatttattc cgatccagtg   780
ggctctacct acgagaacca gctcaacact gacccgccac cgtgccagat cgagatgaac   840
gttagctctc gttctgcaaa aatggctcct ccgctgggct tcgacatcta cagcggcggt   900
aaatggtacg gcccgggtta caccggtggc gtagttggct atgtttccca ttacgaaagc   960
ggtcagggtc cgaacggtac gaccatcgat gaccaccgtc gcctgaacca ccaggacgat  1020
ccgatgttta aaatcgactg caccacggag aaaggtcctg tttgccgcgt actggtgccg  1080
cgccaagacg cggtttctc tatccagttt ttctataaaa atggtagctc tagcccgatg  1140
gctggcggtt gcctgaataa ctaccctccg aacctggaaa ttgcgtatga ccatcacatt  1200
ctggtggaca tcgcttatca atggtacagc cgccacactg gctgcctggg ttgtatcgtt  1260
ctgggttttc agctggaaaa catgggcaaa aacccggacc cgctgttcag cgttcgccag  1320
cgttatatct actccctctg ggaaccgaaa ctgccggacc tggctgactt cgttcgcatg  1380
cagaccggcg tataccaaca gctgaacgag gaacgcctcc tggaagatgt tcagagccag  1440
ctggcttcct ggagcaacgc tcgccgtgcg ttctgggaga actgtcgcaa tgccctgagc  1500
aaaactaccc agtaa                                                   1515
```

```
SEQ ID NO: 21              moltype = DNA  length = 1362
FEATURE                    Location/Qualifiers
misc_feature               1..1362
                           note = Synthetic polynucleotide
source                     1..1362
                           mol_type = other DNA
                           organism = synthetic construct
SEQUENCE: 21
atgcagccgt ccatgggcag ccaggccacc ggtgcagcga tggtgacgtc ttccggcttc   60
gattggaata acgccgcgga acaaggtatt gcgggtattc tgggtctggt gccggaagtt  120
ggcccgctcc tgtctgctct ggtttacatc ttctggcctc agagcaagga ggacatctgg  180
ggtgaaattg aagcgcaggt tgaagcactg attcagaaag acctgagcca gctggtacaa  240
accgaggtaa gcgcgtccct gcaaggtctg aacaatgttc tgaatgacta cctcctggct  300
ctgaaagatg gcaccggtga tccgacctat atctctgaga aatggaacat cgcaaacggc  360
gattttctgc aacagctgcc gacttttcag atgagcggtt atcaagtgct gctcctgccg  420
ctgttcgccc agttctctaa catgcatctg tctctcctgc gtgacggcgt gctgggcggt  480
gcaaaatggg gttggactcc ggctatcctg aagcagactc agatcaccct gacctctact  540
atcgcggctt atgctgcgta cgcgcaaacg acctaccaga ccggtctcac caatgtgcag  600
tctagcacgc caggtaataa ccaacaggct caaccgttcc gtgctgttaa tcagtacgta  660
cgtcagatga ccctcactgt actggatttc atgaacatgt ggcaatactt cgatgtatcc  720
aagtatccga atggtgtttc cgtctacctg aaccgtgaaa tctattctga tccacagggc  780
acttgcgatg acagcggccc tatcgttctg ccttctccac cgaccgcacc aatctctcaa  840
atctctgtgt gggcgtggga ccgtattgac gctgtccagc tgacctaccc tgctggcggt  900
ggcccaggcg gtgtaactac cactgcgcgt atgggcgact agggcggtgg tccaacagc   960
cctccgcacg gtggcgtttt ccaggtcgca gctaacccag ttgtaaccgc gggtggcctg  1020
agcggtgata tcgttaatgc gatgaacttt accttcgcta acggttcttc ctctggccag  1080
ctgggcggta actacccggg cggtggcccg ttcagctact cttatccgaa cgaaatcctg  1140
tcttccatcc atattaacgg catctccaac tattacggtt ctgctgactg cgtggtttat  1200
ggtttcaaat tccgtcagtc taaccagctg agcgcggaca ccgagcgtct cctgtacgtg  1260
acggcgccgg ttgtaccaag cggtactcct gaacactcca ccgtcgatca ggccgcgcgt  1320
aactcctact ggaaacacct ggctaccaaa gcgaaacatt aa                     1362
```

```
SEQ ID NO: 22              moltype = DNA  length = 1464
FEATURE                    Location/Qualifiers
misc_feature               1..1464
                           note = Synthetic polynucleotide
source                     1..1464
                           mol_type = other DNA
                           organism = synthetic construct
SEQUENCE: 22
atgagcaaca atcaagtaat ggctcgcgtt cgtgttaccg aagacggtct ggaacacgtg   60
gtttattcca ctcaagttga ctacgagttt gactataata acgctgcgaa agtggttatc  120
agcgcgtctc tcggtaaaat cccggtggtt ggtttcgcac tgtccgcgct ggttggtatc  180
ttttggccgg catctcatgt tgatgtgtgg gctgaagtta aagaaaaagt agaagcgctg  240
gtagatcgta aaatctccga tctggtttac caacaggtac aggaagacct gaaaggtctg  300
cagaataaca tgaatgaata cctgtgggcc gcgcgtacgt ctaaggttaa gacttatatc  360
tccgaaaaat ataatattgt tctgtggcgat tttctgcaac agctgcctca ctttcagagc  420
aagggttacg aactgccgct cctgccgctc ttcgcccagt cgctaacat gcatctgtct  480
ctcctggccg aggtattct gcacggtgca gattgggtt gaccgagga atccaacag  540
cacacgcgcg aacagattgt tgataccgtg tcctcttaca ttaagtattc cgaaaaagtg  600
tataacgatg gtctgcagga tacccagaag aaagccccgg gcaacaagca ctataccgaa  660
ccgttcaaca cggtcaacaa atatgtacgt gagatgaccc tgactgttct cgattttaaa  720
gacatgtggc agtatttcga cccggttaaa tatccgacgc cggttaaagt atacctgtcc  780
cgcgagatct attccgacgc tgttggtact gcagatgact ctggcggtat taaactgccg  840
agccctccgg gtcagccgat ttccgccgta gaggtatggg gttgggaccg catcgatgca  900
tgccaggtta cctacccaga aggtggcggt ccgcgcgggtg tgactcgcac cgaacgtatg  960
ggcaacgaat ccgcgggttc ttccaaccct ccgcacggcg gtgtgttcga tctgtctggc  1020
actggtccga tcgttaaggt caccgcacgt tccactgaca ttctgaacgc gtggtggttc  1080
acgtttaaag atggttctag ctccaacaag ctgggtggca actatcctgg cggtgccgac  1140
tacgttttcg cgtatccggg cgaagttctg tcctctatca aaatcatggg catctcccgat  1200
ttctaccgtt ctgctgattg cgcagtcttc ggtttttaaat tcgagaaaga atccactctg  1260
accgaccccg cagttctcct gcgcatgtat gttgcatctc catctgcgat tgaaccggaa  1320
gagctggctg cgtacgttgg cctgcagcat tctgaagagg cgtccgagaa aatccgtgct  1380
tggatcaagg actatcactg ggatgacatt cgtgaacgtc actgggcgaa catccaggaa  1440
```

```
tccgttgaag cacgcaaagt ataa                                              1464

SEQ ID NO: 23          moltype = DNA   length = 2103
FEATURE                Location/Qualifiers
misc_feature           1..2103
                       note = Synthetic polynucleotide
source                 1..2103
                       mol_type = other DNA
                       organism = synthetic construct
SEQUENCE: 23
atgtctctgt acaccgcgga aactattccg gcgaccttcc tgaacgcacc ggaaggtggc   60
ttccgtgctc aggacctgcc taaagaagag gaagacctcc tgaaaaccga actgatgatg   120
gttatctctc agatggcgct gggcccgctg ggtggcctgg ttggcctggt gctgaacgaa   180
ctgtggccga acccgcagac cgatctgaaa caggtatttc agggcattct ggacaagatg   240
atggtagtta tcgaacgtat ggtagacgag aagatcaaaa cggcggtatc caacctgtat   300
cacaaactga tggaaaacga actggctggt ctgtataaag tggtagatta ctatcatacc   360
gtggctcgta ccgatcctgg taacgctcct gccgcattta tcagcgcaca cgagcagatc   420
ctgcacgata tgccggcatt ccaggatgcg gactatggtt atctggttct gccgttttc   480
gcacaggttg cgaacctcca tatcatgctc ctgcgtgaag gcatcaacta cgcggacgaa   540
ctgggtctca gcgatgctca ccgtgaggaa ctgattaaaa tgctgaaaga cgttgcatcc   600
gaggacggtg cctataccctc ttacatgaag aaaactttcg acgcgcacgc gttctctacc   660
ggcggtagcg atgagtgcta cctgacgctg gattatcagc gtgagaatta tgttcgtggt   720
gcagaatatg gccgttactt ttggcctgcg ctggcggact gcaataacgc accggaaaaa   780
ctgtatcgcg aagccaccgt atatctccgt tgcggttccg tgctgcacat ggaagatgct   840
gcgaagccgc tggttgcgcc gaactatctc tatgaacaca agcgcgagcc ggcgctggtg   900
agctataagg cagacatgca cgcaccggta tctagcgaca aggttctag cctcctgggc   960
ctgcatctgc actattccga tggccacagc acctggtatt acgccgacga tatggatgaa   1020
ccggcatata ctgtgaacga ctcttccgaa tccggttact ctggtgttac tctgtacctg   1080
gatgtacagg gcggtgagcg tgacgaactg cgtggtttg caggctggca gctgggcgac   1140
gcaaaactct ccacttacct ccactccgca tccgctgtgc acgtagaatt caaagctaaa   1200
gactggtccg tatgcgacgt tcgttatgcg ggtcgttgca acccgctgcg taacgtatac   1260
gaatccggcg taatcgttgg tgtgcatcct accgatgaat acatcacccc ggacaaacag   1320
ttcaccgtac cgtccggtgc tctctgccgt gtgcacgttg cggaaggcga tggtaccctg   1380
gatctggctc gttacgccct gtccgaagca gtcccagtag tcctgcgtaa gcacaacggc   1440
agcgacagcc agctctggca gttccaggag gcaggcgaga atgcgttccg tctggtaaat   1500
gcgtacaacg gtcaagcgct ggcactgcgc gagggccagg tgctgacgac ctccgtcctg   1560
caggaagcga cctcttgggc gctggaagtt cgagaagatc acacccagcg tctgacggcc   1620
acgatcggcc cgggccatca cctggccgcg gacggtaacg ctctgactac cacgaccca   1680
gctgcagcca ctggtggcca ggcgggcaat gcgcgttggg ttgtagtggt cgacccgact   1740
cgttctctgg ccaaactccg tagcactctg ccgaacctga cgaccagcct ggtgaacgta   1800
gacggtcgtt ctgacctgca catgactctg accaacccga cctctggctc tacggttgaa   1860
aattggaccc tgcaattcat cctgccggcc gaggcggta ccgcgctgac taccacgagc   1920
ccggttaacg ttaccgcggt ggaagaggaa cgtggtattc acgttactct gattccgacc   1980
ggtgaccagc gtgatctgca cccgggtcgt gcgtttagct ttgtgctggc aaccactaac   2040
ccggcgccgg ctgcgctgcc accggccgct gttcgtctga acgacaccgc catttccggc   2100
taa                                                                     2103

SEQ ID NO: 24          moltype = DNA   length = 1500
FEATURE                Location/Qualifiers
misc_feature           1..1500
                       note = Synthetic polynucleotide
source                 1..1500
                       mol_type = other DNA
                       organism = synthetic construct
SEQUENCE: 24
atgatcgtta ccgaaaacca ggttgttctg gaaaccctgg ttcgtaaaga cgcgccggaa   60
tacacccctgt actctgcgca ggcggactac gaactggact acaacaacgc ggcgcgtgtt   120
gttatctcta ccgcgctggg tgaaatcccg ggtgttggtt cgcgctgtc tgcgctggtt   180
gaaatcttct ggccggactc tcaggaagac gtttggtctg aaatcaaaga ccaggttgaa   240
gcgctgatcg acgaaaaaat ctctgacctg gtttaccagc aggttcagga agacctggaa   300
ggtctgaaaa acaacctgga cgaataccgtg tgggcggttt cttcctggca gaaaaacccg   360
gtatcttccc agaactctca gacccagacc tacatctctg aaaaatacaa cgttgcgctg   420
ggtgacttct gcagcagct gccgcacttc cagtctaaag gttacgaact gctgctgctg   480
ccgctgttcg cgcagttcgc gaacatgcac ctgaccctg acggtgcgtac ggtgcgtac   540
ggtacctctt ggggttggac cgaagaaatc cagcagcaca cccgtcagca gatcgttgac   600
accatcggtt cttacatcga atacaccgaa accatctaca accagggtct gcaggacacc   660
cagaaaaacg cgccgtctaa caaacactac accgaaccgt tcaacaccgt taaccgttac   720
atccgtgaaa tgacccctgga cgttctggac ttcaaaaaca tgtggcagta cttcgacccg   780
gttaaatacc cgaccccggc ggaagtttac ctgtctcgtg aaatctactc tgacgcggtt   840
ggtaccgcgg acaactctgg tgcgatcaaa ctgccgtctg cgccgaaaca gccgatctct   900
aaagttgaag tttgggcgtg ggaccgtatc gacgcgtgcc gtgttaccta cccgaacggt   960
ggtggtccgc gtggtgttac ccagaccgcg cgtatgggtc acaaatctgg tggttcttct   1020
aacccgcgcg acgtggtgtt tttcaacctg tctggtgaaa acccgatcgt taaagttacc   1080
gcgcgtaacg gtgacatcca gaacgcgtgg tggttcacctc tcaaagacgg ttctgtttct   1140
aacgaactgg tgggtaaccta ctctggtggt tctgaccacg ttttcaccta cccggacgaa   1200
atccgtctt ctatcaaaat catgggtatc tctaactact acggttctgc ggactgcgcg   1260
gttttcggtt tcaaattcga ccgtgaatct accctgccgg cgcaggcggt tctgcagaaa   1320
atgtacgttt cttctccgtc tgcgctgaaa ccggaagaac tggcgggtta cgttggtttc   1380
aaaaactctg aagaagcgat cgaaaaaatc cgtatctgga tcaaagacta caactgggac   1440
```

```
gaaatccgtg aacgtcgttg ggcgaacatc cgtgaatctg ttatcgcgcg tcgtacctaa  1500

SEQ ID NO: 25          moltype = DNA   length = 1503
FEATURE                Location/Qualifiers
misc_feature           1..1503
                       note = Synthetic polynucleotide
source                 1..1503
                       mol_type = other DNA
                       organism = synthetic construct
SEQUENCE: 25
atgatcgtta ccgaaaacca ggttgttctg gaaaccctgg ttcgtaaaga cgcgccggaa   60
tacaccctgt actctgcgca ggcggactac gaactggact acaacaacgc ggcgcgtgtt  120
gttatctcta ccgcgctggg tgaaatcccg ggtgttggtt tcgcgctgtc tgcgctggtt  180
gaaatcttct ggccggactc tcaggaagac gtttggtctg aaatcaaaga ccaggttgaa  240
gcgctgatcg acgaaaaaat ctctgacctg gtttaccagc aggttcagga agacctggaa  300
ggtctgaaaa acaacctgga cgaatacctg tgggcggttt cctcttggca gaaaaacccg  360
gccgcgccgt tccagaactc tcagacccag acctacatct ctgaaaaata caacgttgcg  420
ctgggtgact tcctgcagca gctgccgcac ttccagtcta aaggttacga actgctgctg  480
ctgccgctgt tcgcgcagtt cgcgaacatg cacctgaccc tgctgcgtga cggtgcgctg  540
tacggtacct cttggggttg gaccgaagaa atccagcagc acacccgtca gcagatcgtt  600
gacaccatcg gttcttacat cgaatacacc gaaaccatcg acaaccaggg tctgcaggac  660
acccagaaaa acgcgccgtc taacaaacac tacaccgaac cgttcaacac cgttaaccgt  720
tacatccgtg aaatgaccct ggacgttctg gacttcaaaa acatgtggca gtacttcgac  780
ccggttaaat acccgacccc ggcggaagtt tacctgtctc gtgaaatcta ctctgacgcg  840
gttggtaccg cggacaactc tggtgcgatc aaactgccgt ctgcgccgaa acagccgatc  900
tctaaagttg aagtttgggc gtgggaccgt atcgacgcgt gccgtgttac ctacccgaac  960
ggtggtggtc cgggtggtgt tacccagacc gcgcgtatgg gtgacaaatc tggtggttct 1020
tctaacccgc cgcacggtgg tgttttcaac ctgtctggtg aaaacccgat cgttaaagtt 1080
accgcgcgta ccggtgacat ccagaacgcg tggtggttca ccttcaaaga cggttctgtt 1140
tctaacgaac tgggtggtaa ctactctggt ggttctgacc acgttttcac ctacccggac 1200
gaaatcctgt cttctatcaa aatcatgggt atctctaact actacggttc tgcggactgc 1260
gcggttttcg gtttcaaatt cgaccgtgaa tctaccctgc cggcgcaggc ggttctgcag 1320
aaaatgtacg tttcttctcc gtctgcgctg aaaccggaag aactggcggg ttacgttggt 1380
ttcaaaaact ctgaagaagc gatcgaaaaa atccgtatct ggatcaaaga ctacaactgg 1440
gacgaaatcc gtgaacgtcg ttgggcgaac atccgtgaat ctgttatcgc gcgtcgtacc 1500
taa                                                                 1503

SEQ ID NO: 26          moltype = DNA   length = 1989
FEATURE                Location/Qualifiers
misc_feature           1..1989
                       note = Synthetic polynucleotide
source                 1..1989
                       mol_type = other DNA
                       organism = synthetic construct
SEQUENCE: 26
atgatcgtta ccgaaaacca ggttgttctg gaaaccctgg ttcgtaaaga cgcgccggaa   60
tacaccctgt actctgcgca ggcggactac gaactggact acaacaacgc ggcgcgtgtt  120
gttatctcta ccgcgctggg tgaaatcccg ggtgttggtt tcgcgctgtc tgcgctggtt  180
gaaatcttct ggccggactc tcaggaagac gtttggtctg aaatcaaaga ccaggttgaa  240
gcgctgatcg acgaaaaaat ctctgacctg gtttaccagc aggttcagga agacctggaa  300
ggtctgaaaa acaacctgga cgaatacctg tgggcggttt agaactctca gacccagac  360
tacatctctg aaaaatacaa cgttgcgctg ggtgacttcc tgcagcagct gccgcacttc  420
cagtctaaag gttacgaact gctgctgctg ccgctgttcg cgcagttcgc gaacatgcac  480
ctgaccctgc tgcgtgacgg tgcgctgtac ggtacctctt ggggttggac cgaagaaatc  540
cagcagcaca cccgtcagca gatcgttgac accatcggtt cttacatcga atacaccgt   600
accatctaca accagggtct gcaggacacc cagaaaaacg cgccgtctaa caaacactac  660
accgaaccgt tcaacaccgt taaccgttac atccgtgaaa tgaccctgga cgttctggac  720
ttcaaaaaca tgtggcagta cttcgacccg gttaaatacc cgaccccggc ggaagtttac  780
ctgtctcgtg aaatctactc tgacgcggtt ggtaccgcgg acaactctgg tgcgatcaaa  840
ctgccgtctg cgccgaaaca gccgatctct aaagttgaag tttgggcgtg ggaccgtatc  900
gacgcgtgcc gtgttaccta cccgaacggt ggtggtccgg gtggtgttac ccagaccgcg  960
cgtatgggtg acaaatctgg tggttcttct aacccgccgc acggtggtgt tttcaacctg 1020
tctggtgaaa acccgatcgt taaagttacc gcgcgtaccg gtgacatcca gaacgcgtgg 1080
tggttcacct tcaaagacgg ttctgtttct aacgaactga ctctggtggt 1140
tctgaccacg ttttcacccta cccggacgaa atcctgtctt ctatcaaaat catgggtatc 1200
tctaactact acggttctgc ggactgcgcg gttttcggtt tcaaattcga ccgtgaatct 1260
accctgccgg cgcaggcggt tctgcagaaa atgtacgttt cttctccgtc tgcgctgaaa 1320
ccggaagaac tggcgggtta cgttggtttc aaaaactctg aagaagcgat cgaaaaaatc 1380
cgtatctgga tcaaagacta caactgggac gaaatccgtg aacgtcgttg ggcgaacatc 1440
cgtgaatctg ttatcgcgcg tcgtaccctg accaagagca ccaacctggg cagcggcacc 1500
agcgtggtga agggcccccg gcttcaccggc ggcgacatcc tgcgccgcac cagccccggc 1560
cagatcagca ccctgcgcgt gaacatcacc gcccccctga ccagcgcta ccgcgtccgc 1620
atccgctacg ccagcaccac caacctgcag ttccacacca gcatcgacgg ccgcccatc 1680
aaccagggca acttcagcgc caccatgagc agcggcacga acctgcagag cggcagcttc 1740
cgcaccgtgg gcttcaccac ccccttcaac ttcagcaacg gcagcagcgt gttcaccctg 1800
agcgcccacg tgttcaacag cggcaacgag gtgtacatcg accgcatcga gttcgtgccc 1860
gccgaggtga ccttcgaggc cgagtacgac ctggagaggg ctcagaaggc cgtgaacgag 1920
ctgttcacca gcagcaacca gatcggcctg aagaccgacg tgaccgacta ccacatcgat 1980
caggtgtaa                                                          1989
```

-continued

```
SEQ ID NO: 27          moltype = DNA  length = 1464
FEATURE                Location/Qualifiers
misc_feature           1..1464
                       note = Synthetic polynucleotide
source                 1..1464
                       mol_type = other DNA
                       organism = synthetic construct
SEQUENCE: 27
atgtccgata accaggtcat ggctcgtgtt cgcgttaccg aagacggcct ggaacacgtt   60
gtctatagcg ctcaggtgga ctacgagttc gactacaata acgccgcgaa ggtcgttatt  120
tctgcatccc tgggtaaaat cccggtcgtt ggttttgctc tctctgctct ggtgggtatc  180
ttctggccgg catcccatgt agacgtgtgg gcggaggtta aagaaaaagt ggaagcgctg  240
gtggatcgta aaatttctga tctggtttac caacaggtcc aagaagatct caaaggtctc  300
cagaataaca tgaacgaata tctgtgggct gcacgtacca gcaaagtgaa aacctacatc  360
tccgaaaaat acaacatcgt tctgggcgat ttcctgcagc aactgccaca cttccaaagc  420
aaaggctacg aactgccgct cctgccgctg tttgcgcagt ttgcgaacat gcatctgtct  480
ctcctgcgtg acggtatcct gcatggtgca gactggggct ggaccgaaga gattcaacag  540
cacacccgtg aacagatcgt tgacgcggta tcctcttata tcaaatatgc agaaaaagta  600
tactctgacg gcctggaaga tacccgcaaa aaggccccgt ctaacaaaca ttacacggaa  660
ccgtttaaca ccgttaaccg ttatgttcgt gagatgaccc tgaccgtact ggatttcaaa  720
gatatgtggc agtacttcga cccagttaaa taccgacctc cagcggaagt ttacctgtct  780
cgtgaaatct actctgacgc ggttggtacc gcggacaact ctggtgcgat caaactgccg  840
tctgcgccga aacagccgat ctctaaagtt gaagtttggg cgtgggaccg tatcgacgcg  900
tgccgtgtta cctacccgaa cggtggtggt ccgggtggtg ttacccagac cgcgcgtatg  960
ggtgacaaat ctggtggttc ttctaacccg ccgcacggtg gtgttttcaa cctgtctggt 1020
gaaaacccga tcgttaaagt taccgcgcgt accggtgaca tccagaacgc gtggtggttc 1080
accttcaaag acgttctgt tctaacgaa ctgggtggta actactctgg tggttctgac 1140
cacgttttca cctacccgga cgaaatcctg tcttctatca aaatcatggg tatctctaac 1200
tactacggtt ctgcggactg cgcggttttc ggtttcaaat tcgaccgtga atctaccctg 1260
ccggcgcagg cggttctgca gaaaatgtac gtttcttctc cgtctgcgct gaaaccggaa 1320
gaactggcgg gttacgttgg tttcaaaaac tctgaagaag cgatcgaaaa aatccgtatc 1380
tggatcaaag actacaactg ggacgaaatc cgtgaacgtc gttgggcgaa catccgtgaa 1440
tctgttatcg cgcgtcgtac ctaa                                        1464

SEQ ID NO: 28          moltype = DNA  length = 1470
FEATURE                Location/Qualifiers
misc_feature           1..1470
                       note = Synthetic polynucleotide
source                 1..1470
                       mol_type = other DNA
                       organism = synthetic construct
SEQUENCE: 28
atgatcgtta ccgaaaacca ggttgttctg gaaaccctgg ttcgtaaaga cgcgccggaa   60
tacaccctgt actctgcgca ggcggactac gaactggact acaacaacgc ggcgcgtgtt  120
gttatctcta ccgcgctggg tgaaatcccg ggtgttggt tcgcgctgtc tgcgctggtt  180
gaaatcttct ggccggactc tcaggaagac gtttggtctg aaatcaaaga ccaggttgaa  240
gcgctgatcg acgaaaaaat ctctgacctg gtttaccagc aggttcagga agacctggaa  300
ggtctgaaaa acaacctgga cgaatacctg tgggcggttc agaactctca gacccagacc  360
tacatctctg aaaaatacaa cgttgcgctg ggtgacttcc tgcagcagct gccgcacttc  420
cagtctaaag gttacgaact gctgctgctg ccgctgttcg ccgcgttcgc gaacatgcat  480
ctgaccctgc tgcgtgacgg tgcgctgtac ggtacctctt ggggttggac cgaagaaatc  540
cagcagcaca cccgtcagca gatcgttgac accatcggtt cttacatcga atacaccgaa  600
accatctaca accagggtct gcaggacacc cagaaaaacg cgccgtctaa caaacactac  660
accgaaccgt tcaacaccgt taaccgttac atccgtgaaa tgaccctgga cgttctggac  720
ttcaaaaaca tgtggcagta cttcgacccg gttaaatacc gacccccggt taaagtttat  780
ctgtccgtg agatttattc tgatgcagtt ggtaccgctg atgactctgg tggcatcaaa  840
atcccgtccc caccgggtca gccgatctct gcggtggagg tttgggggttg ggatcgtatt  900
gacgcgtgcc gtgttactta cccggaaggt ggcggtccgg gtggcgttac tcgtaccgaa  960
cgtatgggta acgaaacgg cggttctagc aacctccgc acggcggtgt tttcgacctg 1020
agcggtagcg gcccgattgt gaaagtgacc gcccgctcta cggacattct gaatgcatgg 1080
tggtttacct tcaaagacgg cagctccagc aacaaactcg gtggcaatta ccgggcggt 1140
gccgactacg tgttcaccta cccaggtgaa gtcctgtcta gcattaagat catgggcgtc 1200
tcttactatt accgctccgc ggattgcgcg gttttggtt tcaaattcga aaagaaggc 1260
gctctgcctg acccgactgt gctcctgatg atgtacgcgg cctccccgtc tgccatcgaa 1320
ccggaggaac tggcagctta cgttggcctg caggatagcg aggaagcttc cgagaaaatt 1380
cgtgcttgga tcaaagatta ccactgggac gatatccgtg aacgccgttg ggctagcatt 1440
caggaatcca tcgaagctcg caaaatctaa                                  1470

SEQ ID NO: 29          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 29
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
```

-continued

```
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWAYFDP VKYPTPAEVY LSREIYSDAV GTADNSGAIK LPSAPKQPIS KVEVAWDRI   300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 30          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 30
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQAFDP VKYPTPAEVY LSREIYSDAV GTADNSGAIK LPSAPKQPIS KVEVAWDRI   300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 31          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 31
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYADP VKYPTPAEVY LSREIYSDAV GTADNSGAIK LPSAPKQPIS KVEVAWDRI   300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 32          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 32
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFAP VKYPTPAEVY LSREIYSDAV GTADNSGAIK LPSAPKQPIS KVEVAWDRI   300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 33          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 33
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDA VKYPTPAEVY LSREIYSDAV GTADNSGAIK LPSAPKQPIS KVEVAWDRI   300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489
```

-continued

```
SEQ ID NO: 34          moltype = AA   length = 489
FEATURE                Location/Qualifiers
REGION                 1..489
                       note = Synthetic polypeptide
source                 1..489
                       mol_type = protein
                       organism = synthetic construct
SEQUENCE: 34
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP AKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 35          moltype = AA   length = 489
FEATURE                Location/Qualifiers
REGION                 1..489
                       note = Synthetic polypeptide
source                 1..489
                       mol_type = protein
                       organism = synthetic construct
SEQUENCE: 35
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VAYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 36          moltype = AA   length = 489
FEATURE                Location/Qualifiers
REGION                 1..489
                       note = Synthetic polypeptide
source                 1..489
                       mol_type = protein
                       organism = synthetic construct
SEQUENCE: 36
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKAPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 37          moltype = AA   length = 489
FEATURE                Location/Qualifiers
REGION                 1..489
                       note = Synthetic polypeptide
source                 1..489
                       mol_type = protein
                       organism = synthetic construct
SEQUENCE: 37
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYATPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 38          moltype = AA   length = 489
FEATURE                Location/Qualifiers
REGION                 1..489
                       note = Synthetic polypeptide
source                 1..489
                       mol_type = protein
```

-continued

```
                              organism = synthetic construct
SEQUENCE: 38
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPAPAEVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 39           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 39
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTAAEVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 40           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 40
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPGEVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 41           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 41
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAAVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 42           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 42
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEAY LSREIYSDAV GTADNSGAIK LPSAPKQPIS KVEVWAWDRI  300
```

-continued

```
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 43              moltype = AA   length = 489
FEATURE                    Location/Qualifiers
REGION                     1..489
                           note = Synthetic polypeptide
source                     1..489
                           mol_type = protein
                           organism = synthetic construct
SEQUENCE: 43
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVA LSREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 44              moltype = AA   length = 489
FEATURE                    Location/Qualifiers
REGION                     1..489
                           note = Synthetic polypeptide
source                     1..489
                           mol_type = protein
                           organism = synthetic construct
SEQUENCE: 44
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY ASREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 45              moltype = AA   length = 489
FEATURE                    Location/Qualifiers
REGION                     1..489
                           note = Synthetic polypeptide
source                     1..489
                           mol_type = protein
                           organism = synthetic construct
SEQUENCE: 45
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LAREIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 46              moltype = AA   length = 489
FEATURE                    Location/Qualifiers
REGION                     1..489
                           note = Synthetic polypeptide
source                     1..489
                           mol_type = protein
                           organism = synthetic construct
SEQUENCE: 46
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSAEIYSDAV GTADNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 47              moltype = AA   length = 489
FEATURE                    Location/Qualifiers
```

```
REGION                    1..489
                          note = Synthetic polypeptide
source                    1..489
                          mol_type = protein
                          organism = synthetic construct
SEQUENCE: 47
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSRAIYSDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 48            moltype = AA   length = 489
FEATURE                  Location/Qualifiers
REGION                   1..489
                         note = Synthetic polypeptide
source                   1..489
                         mol_type = protein
                         organism = synthetic construct
SEQUENCE: 48
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREAYSDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 49            moltype = AA   length = 489
FEATURE                  Location/Qualifiers
REGION                   1..489
                         note = Synthetic polypeptide
source                   1..489
                         mol_type = protein
                         organism = synthetic construct
SEQUENCE: 49
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIASDAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 50            moltype = AA   length = 489
FEATURE                  Location/Qualifiers
REGION                   1..489
                         note = Synthetic polypeptide
source                   1..489
                         mol_type = protein
                         organism = synthetic construct
SEQUENCE: 50
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYADAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 51            moltype = AA   length = 489
FEATURE                  Location/Qualifiers
REGION                   1..489
                         note = Synthetic polypeptide
source                   1..489
                         mol_type = protein
                         organism = synthetic construct
SEQUENCE: 51
MIVTENQVVL ETLVRKDAPE YTLYSAQADY ELDYNNAARV VISTALGEIP GVGFALSALV    60
```

-continued

```
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSAAV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 52              moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 52
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDGV GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 53              moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 53
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAA GTADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 54              moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 54
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV ATADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 55              moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 55
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GAADNSGAIK LPSAPKQPIS KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
```

```
RESVIARRT                                                               489

SEQ ID NO: 56           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 56
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTGDNSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                              489

SEQ ID NO: 57           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 57
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTAANSGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                              489

SEQ ID NO: 58           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 58
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADASGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                              489

SEQ ID NO: 59           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 59
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNAGAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                              489

SEQ ID NO: 60           moltype = AA  length = 489
FEATURE                 Location/Qualifiers
REGION                  1..489
                        note = Synthetic polypeptide
source                  1..489
```

```
                            mol_type = protein
                            organism = synthetic construct
SEQUENCE: 60
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSAAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 61          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 61
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSAAIK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 62          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 62
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAAK LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 63          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 63
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIA LPSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 64          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 64
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
```

-continued

```
FKNMWQYFDP VKYPTPAEVY LSREIYSDAV GTADNSGAIK APSAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 65          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 65
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LASAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 66          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 66
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPAAPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 67          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 67
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSGPKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 68          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 68
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAAKQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                          489

SEQ ID NO: 69          moltype = AA  length = 489
```

```
FEATURE              Location/Qualifiers
REGION               1..489
                     note = Synthetic polypeptide
source               1..489
                     mol_type = protein
                     organism = synthetic construct
SEQUENCE: 69
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPAQPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 70          moltype = AA  length = 489
FEATURE              Location/Qualifiers
REGION               1..489
                     note = Synthetic polypeptide
source               1..489
                     mol_type = protein
                     organism = synthetic construct
SEQUENCE: 70
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKAPIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 71          moltype = AA  length = 489
FEATURE              Location/Qualifiers
REGION               1..489
                     note = Synthetic polypeptide
source               1..489
                     mol_type = protein
                     organism = synthetic construct
SEQUENCE: 71
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQAIS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 72          moltype = AA  length = 489
FEATURE              Location/Qualifiers
REGION               1..489
                     note = Synthetic polypeptide
source               1..489
                     mol_type = protein
                     organism = synthetic construct
SEQUENCE: 72
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPAS KVEVWAWDRI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 73          moltype = AA  length = 489
FEATURE              Location/Qualifiers
REGION               1..489
                     note = Synthetic polypeptide
source               1..489
                     mol_type = protein
                     organism = synthetic construct
SEQUENCE: 73
```

-continued

```
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIA KVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 74          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 74
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS AVEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 75          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 75
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KAEVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 76          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 76
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVAVWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 77          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 77
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEAWAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
```

-continued

```
TLPAQAVLQK MYVSSPSALK PEELAGYVGF KNSEEAIEKI RIWIKDYNWD EIRERRWANI   480
RESVIARRT                                                            489

SEQ ID NO: 78            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 78
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVAAWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                            489

SEQ ID NO: 79            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 79
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWGWDRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                            489

SEQ ID NO: 80            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 80
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAADRI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                            489

SEQ ID NO: 81            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 81
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWARI   300
DACRVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                            489

SEQ ID NO: 82            moltype = AA  length = 489
FEATURE                  Location/Qualifiers
REGION                   1..489
                         note = Synthetic polypeptide
```

-continued

```
source                  1..489
                        mol_type = protein
                        organism = synthetic construct
SEQUENCE: 82
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDAI  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 83          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 83
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRA  300
DACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 84          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 84
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
AACRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 85          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 85
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DGCRVTYPNG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 86          moltype = AA  length = 489
FEATURE                Location/Qualifiers
REGION                 1..489
                       note = Synthetic polypeptide
source                 1..489
                       mol_type = protein
                       organism = synthetic construct
SEQUENCE: 86
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
```

-continued

```
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DAARVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 87            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 87
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACAVTYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 88            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 88
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRATYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 89            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 89
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVAYPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 90            moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 90
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTAPNG GGPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489
```

```
SEQ ID NO: 91            moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 91
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYANG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 92            moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 92
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPAG GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 93            moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 93
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNA GGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 94            moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 94
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG AGPGGVTQTA RMGDKSGGSS NPPHGGVFNL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 95            moltype = AA  length = 489
FEATURE                 Location/Qualifiers
REGION                  1..489
                        note = Synthetic polypeptide
source                  1..489
                        mol_type = protein
                        organism = synthetic construct
```

-continued

```
SEQUENCE: 95
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GAPGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 96           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 96
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGAGGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 97           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 97
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPAGVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 98           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 98
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGAVTQTA RMGDKSGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 99           moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 99
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGATQTA RMGDKSGGSS NPPHGGVFNL SGENPIVKVT ARTGDIQNAW   360
```

-continued

```
WFTFKDGSVS NELGGNYSGG SDHVFTYPDE ILSSIKIMGI SNYYGSADCA VFGFKFDRES    420
TLPAQAVLQK MYVSSPSALK PEELAGYVGF KNSEEAIEKI RIWIKDYNWD EIRERRWANI    480
RESVIARRT                                                            489

SEQ ID NO: 100           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 100
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT    120
YISEKYNVAL GDFLQQLPHF QSKGYELLLL PLFAQFANMH LTLLRDGALY GTSWGWTEEI    180
QQHTRQQIVD TIGSYIEYTE TIYNQGLQDT QKNAPSNKHY TEPFNTVNRY IREMTLDVLD    240
FKNMWQYFDP VKYPTPAEVY LSREIYSDAV GTADNSGAIK LPSAPKQPIS KVEVVAWDRI    300
DACRVTYPNG GGPGGVAQTA RMGDKSGGSS NPPHGGVFNL SGENPIVKVT ARTGDIQNAW    360
WFTFKDGSVS NELGGNYSGG SDHVFTYPDE ILSSIKIMGI SNYYGSADCA VFGFKFDRES    420
TLPAQAVLQK MYVSSPSALK PEELAGYVGF KNSEEAIEKI RIWIKDYNWD EIRERRWANI    480
RESVIARRT                                                            489

SEQ ID NO: 101           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 101
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT    120
YISEKYNVAL GDFLQQLPHF QSKGYELLLL PLFAQFANMH LTLLRDGALY GTSWGWTEEI    180
QQHTRQQIVD TIGSYIEYTE TIYNQGLQDT QKNAPSNKHY TEPFNTVNRY IREMTLDVLD    240
FKNMWQYFDP VKYPTPAEVY LSREIYSDAV GTADNSGAIK LPSAPKQPIS KVEVVAWDRI    300
DACRVTYPNG GGPGGVTATA RMGDKSGGSS NPPHGGVFNL SGENPIVKVT ARTGDIQNAW    360
WFTFKDGSVS NELGGNYSGG SDHVFTYPDE ILSSIKIMGI SNYYGSADCA VFGFKFDRES    420
TLPAQAVLQK MYVSSPSALK PEELAGYVGF KNSEEAIEKI RIWIKDYNWD EIRERRWANI    480
RESVIARRT                                                            489

SEQ ID NO: 102           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 102
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT    120
YISEKYNVAL GDFLQQLPHF QSKGYELLLL PLFAQFANMH LTLLRDGALY GTSWGWTEEI    180
QQHTRQQIVD TIGSYIEYTE TIYNQGLQDT QKNAPSNKHY TEPFNTVNRY IREMTLDVLD    240
FKNMWQYFDP VKYPTPAEVY LSREIYSDAV GTADNSGAIK LPSAPKQPIS KVEVVAWDRI    300
DACRVTYPNG GGPGGVTQAA RMGDKSGGSS NPPHGGVFNL SGENPIVKVT ARTGDIQNAW    360
WFTFKDGSVS NELGGNYSGG SDHVFTYPDE ILSSIKIMGI SNYYGSADCA VFGFKFDRES    420
TLPAQAVLQK MYVSSPSALK PEELAGYVGF KNSEEAIEKI RIWIKDYNWD EIRERRWANI    480
RESVIARRT                                                            489

SEQ ID NO: 103           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 103
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT    120
YISEKYNVAL GDFLQQLPHF QSKGYELLLL PLFAQFANMH LTLLRDGALY GTSWGWTEEI    180
QQHTRQQIVD TIGSYIEYTE TIYNQGLQDT QKNAPSNKHY TEPFNTVNRY IREMTLDVLD    240
FKNMWQYFDP VKYPTPAEVY LSREIYSDAV GTADNSGAIK LPSAPKQPIS KVEVVAWDRI    300
DACRVTYPNG GGPGGVTQTG RMGDKSGGSS NPPHGGVFNL SGENPIVKVT ARTGDIQNAW    360
WFTFKDGSVS NELGGNYSGG SDHVFTYPDE ILSSIKIMGI SNYYGSADCA VFGFKFDRES    420
TLPAQAVLQK MYVSSPSALK PEELAGYVGF KNSEEAIEKI RIWIKDYNWD EIRERRWANI    480
RESVIARRT                                                            489

SEQ ID NO: 104           moltype = AA  length = 489
FEATURE                  Location/Qualifiers
REGION                   1..489
```

```
                          note = Synthetic polypeptide
source                    1..489
                          mol_type = protein
                          organism = synthetic construct
SEQUENCE: 104
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA AMGDKSGGSS NPPHGGVFNL SGENPIVKVT ARTGDIQNAW   360
WFTFKDGSVS NELGGNYSGG SDHVPTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 105            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 105
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RAGDKSGGSS NPPHGGVFNL SGENPIVKVT ARTGDIQNAW   360
WFTFKDGSVS NELGGNYSGG SDHVPTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 106            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 106
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMADKSGGSS NPPHGGVFNL SGENPIVKVT ARTGDIQNAW   360
WFTFKDGSVS NELGGNYSGG SDHVPTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 107            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 107
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGAKSGGSS NPPHGGVFNL SGENPIVKVT ARTGDIQNAW   360
WFTFKDGSVS NELGGNYSGG SDHVPTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 108            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 108
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
```

-continued

```
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDASGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 109             moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 109
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKAGGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 110             moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 110
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSAGSS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 111             moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 111
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGASS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 112             moltype = AA  length = 489
FEATURE                    Location/Qualifiers
REGION                     1..489
                           note = Synthetic polypeptide
source                     1..489
                           mol_type = protein
                           organism = synthetic construct
SEQUENCE: 112
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGAS NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489
```

-continued

```
SEQ ID NO: 113          moltype = AA   length = 489
FEATURE                 Location/Qualifiers
REGION                  1..489
                        note = Synthetic polypeptide
source                  1..489
                        mol_type = protein
                        organism = synthetic construct
SEQUENCE: 113
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSA NPPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 114          moltype = AA   length = 489
FEATURE                 Location/Qualifiers
REGION                  1..489
                        note = Synthetic polypeptide
source                  1..489
                        mol_type = protein
                        organism = synthetic construct
SEQUENCE: 114
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS APPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 115          moltype = AA   length = 489
FEATURE                 Location/Qualifiers
REGION                  1..489
                        note = Synthetic poylpeptide
source                  1..489
                        mol_type = protein
                        organism = synthetic construct
SEQUENCE: 115
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NAPHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 116          moltype = AA   length = 489
FEATURE                 Location/Qualifiers
REGION                  1..489
                        note = Synthetic polypeptide
source                  1..489
                        mol_type = protein
                        organism = synthetic construct
SEQUENCE: 116
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPAHGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 117          moltype = AA   length = 489
FEATURE                 Location/Qualifiers
REGION                  1..489
                        note = Synthetic polypeptide
source                  1..489
                        mol_type = protein
```

-continued

```
                          organism = synthetic construct
SEQUENCE: 117
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPAGGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 118          moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 118
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHAGVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 119          moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 119
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGAVFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 120          moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 120
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGAFNL SGENPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 121          moltype = AA  length = 489
FEATURE                 Location/Qualifiers
REGION                  1..489
                        note = Synthetic polypeptide
source                  1..489
                        mol_type = protein
                        organism = synthetic construct
SEQUENCE: 121
MIVTENQVVL ETLVRKDAPE YTLYSAQADY ELDYNNAARV VISTALGEIP GVGFALSALV    60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
```

```
DACRVTYPNG GGPGGVTQTA RMGDKSGGSS NPPHGGVANL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 122           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 122
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFAL SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 123           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 123
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFNA SGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 124           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 124
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFNL AGENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 125           moltype = AA  length = 489
FEATURE                  Location/Qualifiers
REGION                   1..489
                         note = Synthetic polypeptide
source                   1..489
                         mol_type = protein
                         organism = synthetic construct
SEQUENCE: 125
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFNL SAENPIVKVT ARTGDIQNAW  360
WFTFKDGSVS NELGGNYSGG SDHVFTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                         489

SEQ ID NO: 126           moltype = AA  length = 489
FEATURE                  Location/Qualifiers
```

-continued

```
REGION                    1..489
                          note = Synthetic polypeptide
source                    1..489
                          mol_type = protein
                          organism = synthetic construct
SEQUENCE: 126
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGANPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 127            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 127
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGEAPIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 128            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 128
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENAIVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 129            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 129
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPAVKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                          489

SEQ ID NO: 130            moltype = AA  length = 489
FEATURE                   Location/Qualifiers
REGION                    1..489
                          note = Synthetic polypeptide
source                    1..489
                          mol_type = protein
                          organism = synthetic construct
SEQUENCE: 130
MIVTENQVVL ETLVRKDAPE YTLYSAQADY ELDYNNAARV VISTALGEIP GVGFALSALV   60
```

-continued

```
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIAKVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                           489

SEQ ID NO: 131          moltype = AA   length = 489
FEATURE                 Location/Qualifiers
REGION                  1..489
                        note = Synthetic polylpeptide
source                  1..489
                        mol_type = protein
                        organism = synthetic construct
SEQUENCE: 131
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVAVT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                           489

SEQ ID NO: 132          moltype = AA   length = 489
FEATURE                 Location/Qualifiers
REGION                  1..489
                        note = Synthetic polypeptide
source                  1..489
                        mol_type = protein
                        organism = synthetic construct
SEQUENCE: 132
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKAT ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                           489

SEQ ID NO: 133          moltype = AA   length = 489
FEATURE                 Location/Qualifiers
REGION                  1..489
                        note = Synthetic polypeptide
source                  1..489
                        mol_type = protein
                        organism = synthetic construct
SEQUENCE: 133
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKVA ARTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
RESVIARRT                                                           489

SEQ ID NO: 134          moltype = AA   length = 489
FEATURE                 Location/Qualifiers
REGION                  1..489
                        note = Synthetic polypeptide
source                  1..489
                        mol_type = protein
                        organism = synthetic construct
SEQUENCE: 134
MIVTENQVVL ETLVRKDAPE YTLYSAQADY ELDYNNAARV VISTALGEIP GVGFALSALV   60
EIFWPDSQED VWSEIKDQVE ALIDEKISDL VYQQVQEDLE GLKNNLDEYL WAVQNSQTQT   120
YISEKYNVAL GDFLQQLPHF QSKGYELLLL PLFAQFANMH LTLLRDGALY GTSWGWTEEI   180
QQHTRQQIVD TIGSYIEYTE TIYNQGLQDT QKNAPSNKHY TEPFNTVNRY IREMTLDVLD   240
FKNMWQYFDP VKYPTPAEVY LSREIYSDAV GTADNSGAIK LPSAPKQPIS KVEVWAWDRI   300
DACRVTYPNG GGPGGVTQTA RMGDKSGGSS NPPHGGVFNL SGENPIVKVT GRTGDIQNAW   360
WFTFKDGSVS NELGGNYSGG SDHVFTYPDE ILSSIKIMGI SNYYGSADCA VFGFKFDRES   420
TLPAQAVLQK MYVSSPSALK PEELAGYVGF KNSEEAIEKI RIWIKDYNWD EIRERRWANI   480
```

-continued

```
RESVIARRT                                                                           489

SEQ ID NO: 135            moltype = AA   length = 489
FEATURE                   Location/Qualifiers
REGION                    1..489
                          note = Synthetic polypeptide
source                    1..489
                          mol_type = protein
                          organism = synthetic construct
SEQUENCE: 135
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LTLLRDGALY GTSWGWTEEI  180
QQHTRQQIVD TIGSYIEYTE TIYNQGLQDT QKNAPSNKHY TEPFNTVNRY IREMTLDVLD  240
FKNMWQYFDP VKYPTPAEVY LSREIYSDAV GTADNSGAIK LPSAPKQPIS KVEVWAWDRI  300
DACRVTYPNG GGPGGVTQTA RMGDKSGGSS NPPHGGVFNL SGENPIVKVT AATGDIQNAW  360
WFTFKDGSVS NELGGNYSGG SDHVPTYPDE ILSSIKIMGI SNYYGSADCA VFGFKFDRES  420
TLPAQAVLQK MYVSSPSALK PEELAGYVGF KNSEEAIEKI RIWIKDYNWD EIRERRWANI  480
RESVIARRT                                                                           489

SEQ ID NO: 136            moltype = AA   length = 489
FEATURE                   Location/Qualifiers
REGION                    1..489
                          note = Synthetic polypeptide
source                    1..489
                          mol_type = protein
                          organism = synthetic construct
SEQUENCE: 136
MIVTENQVVL ETLVRKDAPE YTLYSAQADY ELDYNNAARV VISTALGEIP GVGFALSALV  60
EIFWPDSQED VWSEIKDQVE ALIDEKISDL VYQQVQEDLE GLKNNLDEYL WAVQNSQTQT  120
YISEKYNVAL GDFLQQLPHF QSKGYELLLL PLFAQFANMH LSLLRDGALY GNSWGWTEEI  180
QQHTRQQIAD TISSYIAYTE KIYNDGLQAT QKNAPSNKHY TEPFNTVNRY IREMTINVLD  240
FKNMWQYFDP VKYSTPAEVY LSREIYSDAV GTADNSGTIR LPSAPEQPIS KVEVWAWDRI  300
DACQVTYPNG GGPGGVTQTS RMGDKSGGSS NPPHGGVFNL SRENQIVKVT ARTGDILNAW  360
WFTFKDGSVS NELGGNYPGG SDNVFTYPDE ILSSIKIMGV SSYYGSADCA VFGFKFDRES  420
TLPDQAVLQK MYIASPSALK PEELTSYVGF KNSEEASERI RTWIKDNNWD EIRERRWANI  480
RESIIARRT                                                                           489

SEQ ID NO: 137            moltype = DNA   length = 1470
FEATURE                   Location/Qualifiers
misc_feature              1..1470
                          note = Synthetic polypeptide
source                    1..1470
                          mol_type = other DNA
                          organism = synthetic construct
SEQUENCE: 137
atgatcgtta ccgaaaacca ggttgttctg gaaaccctgg ttcgtaaaga cgcgccggaa  60
tacaccctgt actctgcgca ggcggactac gaactggact acaacaacgc ggcgcgtgtt  120
gttatctcta ccgcgctggg tgaaatcccg ggtgttggtt tcgcgctgtc tgcgctggtt  180
gaaatcttct ggccggactc tcaggaagac gtttggtctg aaatcaaaga ccaggttgaa  240
gcgctgatcg acgaaaaaat ctctgacctg gtttaccagc aggttcagga gacctggaa  300
ggtctgaaaa acaacctgga cgaatacctg tgggcggttc agaactctca gacccagacc  360
tacatctctg aaaaatacaa cgttgcgctg ggtgacttcc tccagcagct gccgcacttc  420
cagtctaaag gttacgaact gctgctgctg ccgctgttcg cgcagttcgc gaacatgcac  480
ctgtctctcc tgcgtgacgg tgctctctat ggtaactcct gggggttggac tgaagagatt  540
caacagcaca cccgtcaaca gatcgccgat accatctcta gctacatcgc ctacacggaa  600
aagatctata cgatggtct gcaggctacc cagaagaacg caccttctaa caaacactac  660
actgagcctt tcaacaccgt caaccgttat atccgtgaaa tgaccattaa cgtgctcgat  720
ttcaaaaaca tgtggcagta tttcgacccg gttaaatact ccacgccggc agaagtgtac  780
ctgtctcgcg aaatctatag cgatgctgtt ggtactgcgg acaactctgg tacgatccgt  840
ctgccgtctg ctccagaaca gccgatctcc aaagttgaag tgtgggcttg ggaccgcatt  900
gacgcgtgcc aagtaaccta cccgaacggt ggcggtccgg gcggtgttac tcagacttcc  960
cgtatgggcg acaaaagcgg cggttcctct aatcctccac atggcggtgt gttcaacctg  1020
tctcgtgaaa accagatcgt gaaagtgacc gcgcgtaccg gtgatatcct gaacgcttgg  1080
tggttcacct tcaaagatgg tagcgtcagc aacgaactgg gcggtaacta cccgggcggt  1140
tccgataacg tgttcaccta cccagacgag attctgtcct ctatcaaaat tatgggtgta  1200
tcctcttatt acggctctgc cgattgcgct gtcttcggtt tcaagttcga ccgtgaatcc  1260
accctgccgg atcaagcggt actgcaaaaa atgtacatcg cgtcccctc cgcgctcaaa  1320
ccagaggaac tcactagcta cgtgggcttc aaaaacagcg aggaagctag cgaacgcatc  1380
cgcacctgga ttaaggataa taactgggac gaaatccgcg agcgccgttg ggctaacatc  1440
cgtgaatcta ttatcgcccg ccgtacctaa                                    1470
```